United States Patent
Matsubara et al.

(10) Patent No.: US 9,234,826 B2
(45) Date of Patent: Jan. 12, 2016

(54) ASSESSMENT OF SHEAR FATIGUE PROPERTY OF ROLLING CONTACT METAL MATERIAL AND ESTIMATION OF FATIGUE LIMIT MAXIMUM CONTACT PRESSURE USING SAME ASSESSMENT

(75) Inventors: Yukio Matsubara, Kuwana (JP); Noriaki Sakanaka, Kuwana (JP); Hitoshi Ishii, Hamamatsu (JP)

(73) Assignee: NTN CORPORATION, Osaka (JP)

( * ) Notice: Subject to any disclaimer, the term of this patent is extended or adjusted under 35 U.S.C. 154(b) by 620 days.

(21) Appl. No.: 13/634,412

(22) PCT Filed: Mar. 15, 2011

(86) PCT No.: PCT/JP2011/056037
§ 371 (c)(1),
(2), (4) Date: Sep. 12, 2012

(87) PCT Pub. No.: WO2011/115101
PCT Pub. Date: Sep. 22, 2011

(65) Prior Publication Data
US 2013/0006542 A1 Jan. 3, 2013

(30) Foreign Application Priority Data

| Mar. 16, 2010 | (JP) | 2010-059357 |
| Mar. 16, 2010 | (JP) | 2010-059358 |
| Mar. 16, 2010 | (JP) | 2010-059359 |
| Mar. 11, 2011 | (JP) | 2011-054484 |
| Mar. 11, 2011 | (JP) | 2011-054485 |
| Mar. 11, 2011 | (JP) | 2011-054486 |
| Mar. 11, 2011 | (JP) | 2011-054487 |
| Mar. 11, 2011 | (JP) | 2011-054488 |
| Mar. 11, 2011 | (JP) | 2011-054489 |
| Mar. 11, 2011 | (JP) | 2011-054490 |
| Mar. 11, 2011 | (JP) | 2011-054491 |

(51) Int. Cl.
*G01N 3/34* (2006.01)

(52) U.S. Cl.
CPC .......... *G01N 3/34* (2013.01); *G01N 2203/0005* (2013.01); *G01N 2203/0021* (2013.01); *G01N 2203/0025* (2013.01); *G01N 2203/0658* (2013.01)

(58) Field of Classification Search
CPC ...................................................... G01M 13/04
USPC .......................................................... 702/34
See application file for complete search history.

(56) References Cited

U.S. PATENT DOCUMENTS

| 5,837,882 A | 11/1998 | Bacigalupo et al. |
| 6,912,913 B2 | 7/2005 | Murakami |

(Continued)

FOREIGN PATENT DOCUMENTS

| CN | 1500207 | 5/2004 |
| JP | 62-153731 | 7/1987 |

(Continued)

OTHER PUBLICATIONS

Bayraktar et al., Torsional Fatigue Bahavior and Damage Mechanisms in the Very High Cycle Regime, Jun. 2010, Archives of Materials Science and Engineering, vol. 43, Issue 2, pp. 77-86.*

(Continued)

*Primary Examiner* — John Breene
*Assistant Examiner* — Raymond Nimox

(57) ABSTRACT

A method of assessing the shear fatigue property of a metallic material that undergoes a rolling contact includes a testing step for determining the relation between the shear stress amplitude of a rolling contact metallic material and the number of loading by means of an ultrasonic torsional fatigue test, and a shear fatigue strength determining step for determining the shear fatigue strength τlim within the ultra long life regime from the relation between the shear stress amplitude and the number of loadings, which relation has been determined during the test step, in accordance with a predetermined standard. It is a completely reversed torsional fatigue test, in which torsional vibrations, respective torsions in the positive rotational direction and reversed rotational direction of which are symmetrical relative to each other, are applied to a test piece.

25 Claims, 33 Drawing Sheets

(56) References Cited

U.S. PATENT DOCUMENTS

| | | | |
|---|---|---|---|
| 7,577,555 | B2 | 8/2009 | Umeda et al. |
| 8,290,753 | B2* | 10/2012 | Tryon et al. ............... 703/2 |
| 2003/0024323 | A1* | 2/2003 | Wang et al. ............... 73/847 |
| 2004/0112141 | A1 | 6/2004 | Murakami |
| 2007/0044543 | A1 | 3/2007 | Umeda et al. |
| 2007/0163687 | A1* | 7/2007 | Kurosawa et al. ......... 148/566 |
| 2010/0235110 | A1* | 9/2010 | Wang et al. ............... 702/35 |
| 2010/0299085 | A1* | 11/2010 | Slycke et al. ............. 702/42 |
| 2010/0332153 | A1* | 12/2010 | Vegter et al. ............. 702/42 |
| 2011/0288790 | A1* | 11/2011 | Dong et al. ............... 702/34 |

FOREIGN PATENT DOCUMENTS

| | | |
|---|---|---|
| JP | 62-293140 | 12/1987 |
| JP | 11-51836 | 2/1999 |
| JP | 2002-243604 | 8/2002 |
| JP | 2002-286031 | 10/2002 |
| JP | 2002-286607 | 10/2002 |
| JP | 2004-176156 | 6/2004 |
| JP | 2004-251898 | 9/2004 |
| JP | 2005-105363 | 4/2005 |
| JP | 2005-133768 | 5/2005 |
| JP | 2006-138376 | 6/2006 |
| JP | 2006-138865 | 6/2006 |
| JP | 2006-308019 | 11/2006 |
| JP | 2006-349698 | 12/2006 |
| JP | 2007-17288 | 1/2007 |
| JP | 2007-32662 | 2/2007 |
| JP | 2008-8419 | 1/2008 |
| JP | 2009-281738 | 12/2009 |

OTHER PUBLICATIONS

Chinese Office Action issued May 30, 2014 in corresponding Chinese Patent Application No. 201180013980.3.

Japanese Office Action issued Jul. 15, 2014 in corresponding Japanese Patent Application No. 2011-054484.

"Investigation on gigacycle fatigue behavior and damage mechanism of cast aluminum 2-AS5U3G-Y35 in tension and torsion loading", Xue et al., The Chinese Society of Theoretical and Applied Mechanics 2009 Studies Convention Symposium, Dec. 2009, 7pp.

"Investigation on Fatigue Behavior of Materials in Very High Cycle Regime under Vibratory Loading", Xue, Chinese Doctoral Dissertations Full-Text Database, Dec. 2006, 4pp.

"Development of a new device to perform torsional ultrasonic fatigue testing", Marines-Garcia et al., International Journal of Fatigue, vol. 29, Apr. 2007, pp. 2094-2101.

Japanese Office Action issued Jul. 22, 2014 in corresponding Japanese Patent Application No. 2011-054486.

Japanese Office Action issued Jul. 22, 2014 in corresponding Japanese Patent Application No. 2011-054487.

Japanese Office Action issued Jul. 22, 2014 in corresponding Japanese Patent Application No. 2011-054489.

Japanese Office Action issued Jul. 22, 2014 in corresponding Japanese Patent Application No. 2011-054490.

International Search Report of Corresponding PCT Application PCT/JP2011/056037 mailed May 24, 2011.

Yoshinobu Shimamura et al, "Choonpa Nejiri Hiro Shiken Sochi no Kokyodo (Ultrasonic Torsion Fatigue Testing of High Strength Steel)", The Society of Materials Science, Japan Dai 58 Ki Gakujutsu Koenkai Koen Ronbunshu, May 22, 2009, pp. 97-98.

Jun Iijima et al, "High cycle torsion fatigue characteristic by ultrasonic fatigue testing method", The Japan Society of Mechanical Engineers Tokai Shibu Sokai Koenkai Koen Ronbunshu, Mar. 1, 2005, No. 053-1, $54^{th}$, pp. 131-132.

Noriaki Sakanaka et al., "Choonpa Nejiri Hiro Shikenki ni yoru Jikuuke Hagane JIS-SUJ2 no Hyoka (Evaluation of Rolling Bearing Steel JIS-SUJ2 by Ultrasonic Torsional Fatigue Tester)", Japanese Society of Tribologists Tribology Kaigi Yokoshu, Sep. 1, 2010, 2010-9, pp. 253-254.

Noriaki Sakanaka et al., "Korogari Jikuuke Hagane o Hyoka suru Tameno Choonpa Nejiri Hiro Shikenki no Kaihatsu (Development of Ultrasonic Torsional Fatigue Tester to Evaluate Rolling Bearting Steel)", Ultrasonic Technology, Apr. 1, 2011, vol. 23, No. 2, pp. 63-67.

Yukio Fujii et al., "A New Test Method for Mode II Fatigue Crack Growth in Hard Steels", NTN technical Review, No. 69, 2001, pp. 53-60.

Y. Murakami et al, "Mechanism of rolling contact fatigue and measurement of $\Delta K_{IIth}$ (Engineering Against Fatigue)", Chapter 52, Univ, of Sheffield, UK, 1997, pp. 473-485.

T.A. Harris, "Contact Stress and Deformation (Rolling Bearing Analysis)", Chapter 5, $3^{rd}$ Edition, Willey Interscience, New York, 1991, pp. 147-190.

Nippon Zairyo Gakkai et al., "Japan Society of Material, Revised Studies on Material Strength", Kyoto, 2006, pp. 94-105.

Nippon Zairyo Gakkai et al., "Japan Society of Material, Revised Studies on Material Strength", Kyoto, 2006, pp. 205-215.

Yukio Matsubara et al., "A Novel Method to Evaluate the Influence of Hydrogen on Fatigue Properties of High Strength Steels (Bearing Steel Technology)", ASTM STP 1465, J.M. Beswick Ed., 2007, pp. 1-15.

M.A. V. Devanathan et al, "The absorption and diffusion of electrolytic hydrogen in palladium", Proc. Royal Soc., A270, 1962, pp. 90-102.

English Translation of the International Preliminary Report on Patentability mailed Nov. 1, 2012 in corresponding Japanese Patent Application No. PCT/JP2011/056037.

Yoshinobu Shimamura et al, "Choonpa Nejiri Hiro Shiken Sochi no Kokyodo Hagane eno Tekiyo (Ultrasonic Torsion Fatigue Testing of High Strength Steel)", The Society of Materials Science, Japan Dai 58 Ki Gakujutsu Koenkai Koen Ronbunshu, May 22, 2009, pp. 97-98.

Noriaki Sakanaka et al., "Choonpa Nejiri Hiro Shikenki ni yoru Jikuuke Hagane JIS-SUJ2 no Hyoka (Evaluation of Rolling Bearing Steel JIS-SUJ2 by Ultrasonic Torsional Fatigue Tester)", Japanese Society of Tribologists Tribology Kaigi Yokoshu, Sep. 1, 2010, 2010-9, pp. 253-254.

Noriaki Sakanaka et al., "Korogari Jikuuke Hagane o Hyoka suru Tameno Choonpa Nejiri Hiro Shikenki no Kaihatsu (Development of Ultrasonic Torsional Fatigue Tester to Evaluate Rolling Bearing Steel)", Ultrasonic Technology, Apr. 1, 2011, vol. 23, No. 2, pp. 63-67.

Y. Murakami et al, "Mechanism of rolling contact fatigue and measurement of $\Delta K_{IIth}$ for steels (Engineering Against Fatigue)", Chapter 52, Univ, of Sheffield, UK, 1997, pp. 473-485.

* cited by examiner

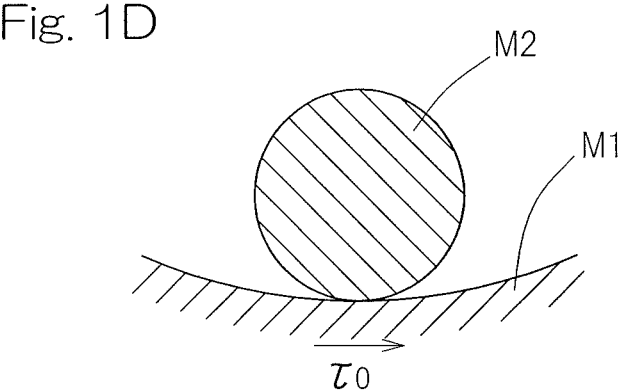

Fig. 2
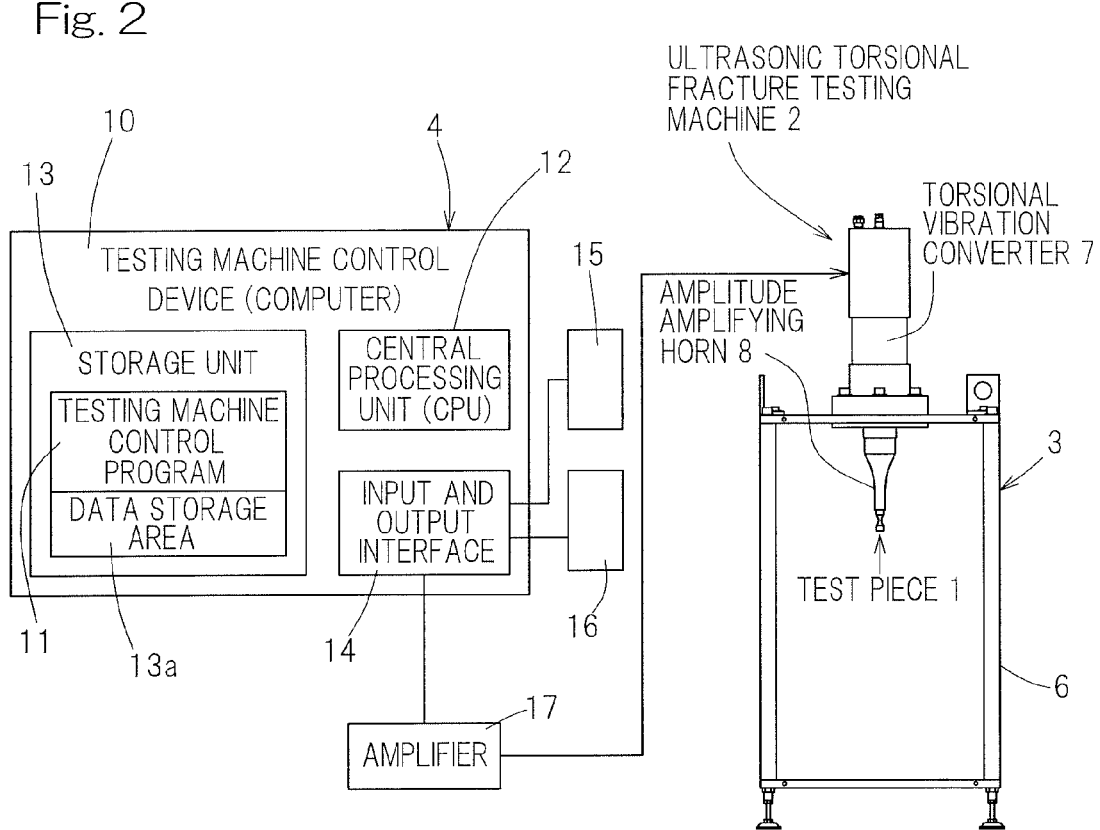
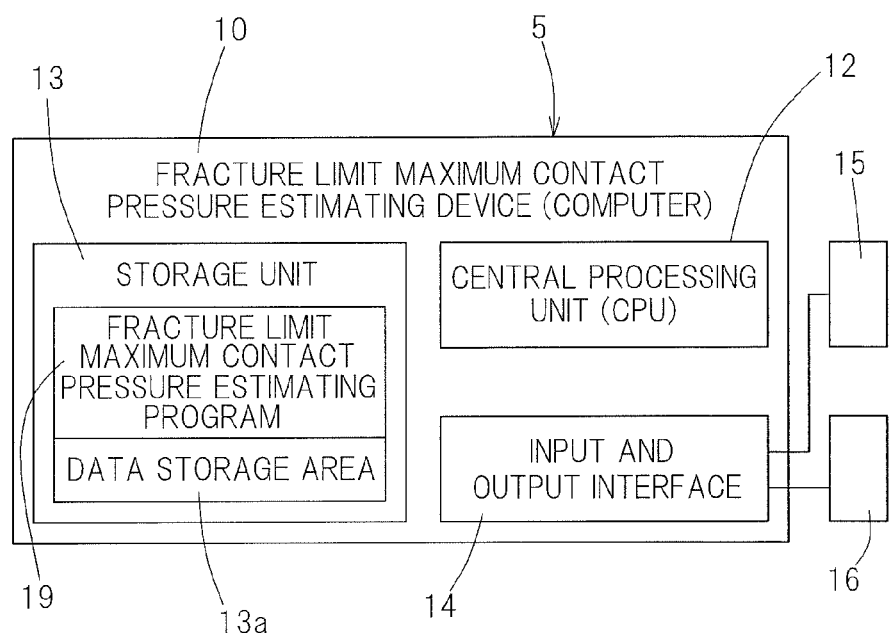

SCHEMATIC DIAGRAM OF TEST PIECE

DIAGRAM OF TEST PIECE SUBJECT TO TEST
(mm IN UNIT)

TORSIONAL ANGLE $\theta$ AND SURFACE SHEAR STRESS $\tau$
(WHEN END FACE TORSIONAL ANGLE $\theta_{end}$ IS 0.01 rad)

TEST PIECE SHOULDER PORTION CYLINDRICAL
SURFACE LOWER END WHEN HALTED

TEST PIECE SHOULDER PORTION CYLINDRICAL
SURFACE LOWER END WHEN OSCILLATED

RELATION BETWEEN RANGE 2a IN Fig. 10 AND
END FACE TORSIONAL ANGLE $\theta_{end}$ RELATION BETWEEN AMPLIFIER OUTPUT P AND
END FACE TORSIONAL ANGLE $\theta_{end}$

EXAMPLE OF TEST PIECE UNDERGOING
SHEAR FATIGUE FRACTURE

RELATION BETWEEN SHEAR STRESS AMPLITUDE AND
NUMBER OF LOADINGS, OBTAINED FROM ULTRASONIC TORSIONAL
FRACTURE TEST, AND S-N DIAGRAM (SOLID LINE)

P-S-N DIAGRAM AT 10% FRACTURE PROBABILITY
DETERMINED FROM RELATION BETWEEN SHEAR STRESS
AMPLITUDE AND NUMBER OF LOADINGS (BROKEN LINE)

Fig. 17

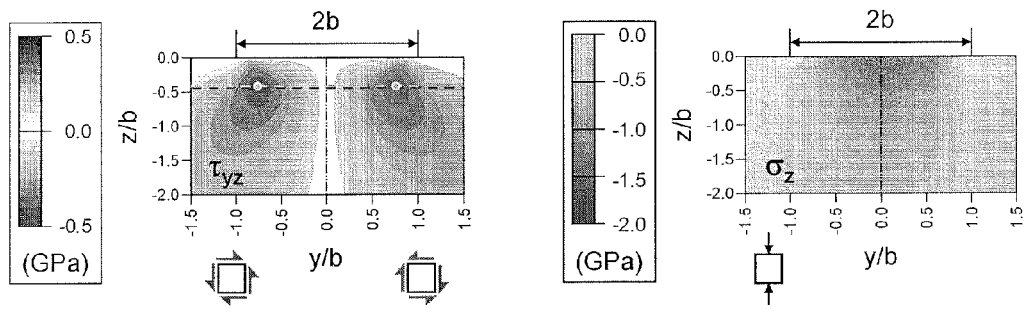

DISTRIBUTION OF ORTHOGONAL SHEAR STRESS $\tau_{yz}$ IN CONTACT SURFACE LOWER PERIPHERAL SECTION AND DISTRIBUTION OF NORMAL STRESS $\sigma_z$ IN DEPTHWISE DIRECTION WHEN $P_{max}$ = 1,500 MPa ACTS UNDER LINE CONTACT CONDITION (y: CIRCUMFERENTIAL DIRECTION, z: DEPTHWISE DIRECTION)

Fig. 18

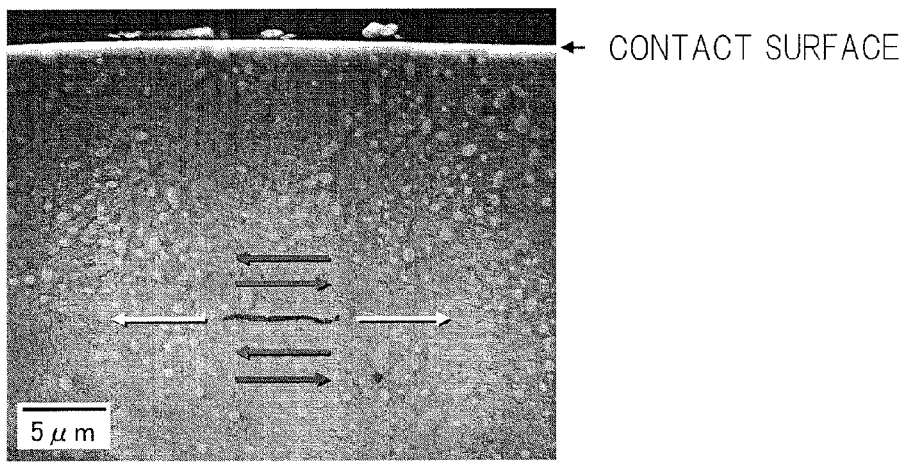

MINUTE CRACKS PARALLEL APPEARING ON SURFACE ABOUT AT DEPTH AT WHICH ABSOLUTE VALUE OF ORTHOGONAL SHEAR STRESS IS MAXIMIZED. (SECTION IN CIRCUMFERENTIAL DIRECTION)

Fig. 19

ULTRASONIC FRACTURE TEST PROCESSING SYSTEM

TESTING CONDITIONS | TEST INFORMATION | INITIAL SETTING

TEST PIECE MATERIAL
MATERIAL IDENTIFICATION: SUJ2 STANDARD
COMMENT

DATA COLLECTING CONDITIONS
INITIAL NUMBER OF LOADING: 100000
TERMINATING NUMBER OF LOADING: 1E+10
COLLECTING INTERVAL: 1000000
FILE NAME

MEASURING CONDITIONS
OUTPUT (10%~100%): 50.00
MAXIMUM SHEAR STRESS AMPLITUDE (MPa): 538.54
INTERMITTENT RUN CONDITIONS OSCILLATION (msec): 110
OSCILLATION (msec): 1,100
◉ INTERMITTENT RUN CONDITIONS
○ CONTINUOUS RUN CONDITIONS
TEST TERMINATING CONDITION COUNTER: 1E+10
FREQUENCY FLUCTUATION BAND: 50.00

MEASUREMENT ARRANGEMENT
OUTPUT (10%): 
RESONANCE FREQUENCY: 19.97
START TRANSMISSION (S)

2009/10/29  12:45

SHEAR FATIGUE PROPERTY
OF THROUGH HARDENED SUJ2

SHEAR FATIGUE PROPERTY OF CARBONITRIDED SUJ2

SHEAR FATIGUE PROPERTY OF CARBURIZED SCr420

SHEAR FATIGUE PROPERTY OF THROUGH HARDENED M50

SHEAR FATIGUE PROPERTY OF CARBURIZED M50NiL

SHEAR FATIGUE PROPERTY OF CARBURIZED SNCM420

SHEAR FATIGUE PROPERTY OF THROUGH HARDENED SUJ3

SHEAR FATIGUE PROPERTY OF INDUCTION HARDENED S53C

TIME-DEPENDENT CHANGE OF RELATIVE HYDROGEN
CONCENTRATION AT TEST PIECE MINIMUM DIAMETER PORTION

RELATION BETWEEN SHEAR STRESS AMPLITUDE AND NUMBER OF LOADING WITH AND WITHOUT HYDROGEN CHARGING (SOLID LINE), OBTAINED AS A RESULT OF ULTRASONIC TORSIONAL FRACTURE TEST

P-S-N DIAGRAM (BROKEN LINE) OF FRACTURE PROBABILITY
DETERMINED FROM RELATION BETWEEN SHEAR STRESS AMPLITUDE AND
NUMBER OF LOADINGS OF Fig. 42 AT 10% FRACTURE PROBABILITY

SHEAR FRACTURE PROPERTY OF
INDUCTION HARDENED TEST PIECES X AND Y

ASSESSMENT OF SHEAR FATIGUE PROPERTY OF ROLLING CONTACT METAL MATERIAL AND ESTIMATION OF FATIGUE LIMIT MAXIMUM CONTACT PRESSURE USING SAME ASSESSMENT

CROSS REFERENCE TO THE RELATED APPLICATIONS

This application is a U.S. national stage application of PCT/JP2011/056037 filed Mar. 15, 2011 and claims the foreign priority benefit of Japanese Applications No. 2010-059357, No. 2010-059358, No. 2010-59359, all filed Mar. 16, 2010; Japanese Applications No. 2011-054484, No. 2011-054485, No. 2011-054486, No. 2011-054487, No. 2011-054488, No. 2011-054489, No. 2011-054490, No. 2011-054491, all filed Mar. 11, 2011 in the Japanese Intellectual Property Office, the contents of all of which are incorporated herein by reference.

BACKGROUND OF THE INVENTION

1. Field of the Invention

The present invention relates to a method of assessing the shear fatigue property of a rolling contact metal material and a method of and an apparatus for estimating the fatigue limit maximum contact pressure and, more specifically, to a method of and an apparatus for quickly assessing the shear fatigue property of a high strength metal material for rolling bearings such as, for example, a bearing steel.

2. Description of Related Art

For the assessment of the shear fatigue property, such testing machines as hydraulic servo type torsional fatigue testing machine and Schenk type torsional fatigue testing machine have been utilized, but the load frequency is limited to about 10 Hz at maximum in the case of the hydraulic servo type torsional fatigue testing machine and about 30 Hz at maximum in the case of the Schenk type torsional fatigue testing machine. Accordingly, where the fatigue limit is desired to be determined, assessment of the shear fatigue property to the ultra long life regime requires a substantial amount of time. High carbon chromium bearing steel, identified by JIS-SUJ2 according to the Japanese Industrial Standards, is currently most often used for a high strength metal material for rolling bearings and it is of a kind which is, after having been heated under the reducing atmosphere at a temperature (about 850° C.) higher than the AI transformation point, quenched and is then tempered at a relatively low temperature (about 180° C.) with its hardness being about 750 HV.

In the case of the rolling bearing, the subsurface-originating flaking failure that occur, when the lifetime is expired, under a favorable lubricating condition is considered attributable to the occurrence of and subsequent extension cracking resulting from repetition of orthogonal shear stresses (completely reversed stress) that exhibits the highest amplitude within the subsurface. In the case of the tension and compression fatigue test (axial load fatigue test, rotating bending fatigue test), it is institutive to deem the fatigue strength of $10^7$ times as a fatigue limit. In contrast thereto, in the case of the rolling bearing, no subsurface-originating flaking failure occurs under the number of loadings of about $10^7$ times even though a fairly high load is applied, if such rolling bearing is used under a good lubricating condition. While the torsional fatigue test is available as a test for inducing a fatigue fracture with shear stresses, the load frequency employed in the hydraulic servo type torsional fatigue test is 10 Hz at most and at least three years is required to reach the number of, for example, $10^9$ loadings. For this reason, it is really impossible to determine the shear fatigue property up until the ultra long life regime.

Instead thereof, in view of the notion that the non-metallic inclusion, which appears to constitute a source of stress concentration as it is necessarily contained in steel and is structurally discontinuous, tends to constitute source of the subsurface-originating flaking failure, a technique of estimating the maximum size of the non-metallic inclusion, contained in an arbitrary volume, by means of an extreme value statistic analysis has been devised, and the method, in which the maximum size of the non-metallic inclusion is used as the quality index of the steel. In this respect, see the patent documents 1 to 4 listed below.

PRIOR ART LITERATURE

Patent Documents

[Patent Document 1] JP Laid-open Patent Publication No. 2004-251898
[Patent Document 2] JP Laid-open Patent Publication No. 2005-105363
[Patent Document 3] JP Laid-open Patent Publication No. 2006-138865
[Patent Document 4] JP Laid-open Patent Publication No. 2006-349698
[Patent Document 5] JP Laid-open Patent Publication No. 2004-176156
[Patent Document 6] JP Laid-open Patent Publication No. 2005-133768
[Patent Document 7] JP Laid-open Patent Publication No. 2006-308019
[Patent Document 8] JP Laid-open Patent Publication No. 2008-008419
[Patent Document 9] JP Laid-open Patent Publication No. 2006-138376

Non-Patent Documents

[Non-patent Document 1]
Yukio Fujii, Kikuo Maeda and Akio Ohtsuka, "A New Test Method for Mode II Fatigue Crack Growth in Hard Steels" NTN Technical Review, No. 69 (2001) pp. 53-60
[Non-patent Document 2]
Y. Murakami, C. Sakae and S. Hamada, "Engineering Against Fatigue", Univ. of Sheffield, UK, (1997), pp. 473
[Non-patent Document 3]
T. A. Harris, "Rolling Bearing Analysis", 3rd edition, Willey Interscience, New York, (1991), pp. 147
[Non-patent Document 4]
"Nippon Zairyo Gakkai, Kaitei Zairyo Kyodo-Gaku", Nippon Zairyo Gakkai, Kyoto, ("Japan Society of Material, Revised Studies on Material Strength", Society of Material Engineering), Kyoto, (2006), pp. 94
[Non-patent Document 5]
"Nippon Zairyo Gakkai, Kaitei Zairyo Kyodo-Gaku", Nippon Zairyo Gakkai, Kyoto, ("Japan Society of Material, Revised Studies on Material Strength", Society of Material Engineering), Kyoto, (2006), pp. 211
[Non-patent Document 6]
Y. Matsubara and H. Hamada, "Bearing Steel Technology", ASTM STP 1465, J. M. Beswick Ed., (2007), pp. 153-166
[Non-patent Document 7]
M. A. Devanathan and Z. Stachurski, "The adsorption and diffusion of electrolytic hydrogen in palladium", Proc. Royal Soc., A270 (1962) pp. 90-102

The extension of the fatigue cracking in a rolling contact subsurface prior to the occurrence of the subsurface-originating flaking failure is generally considered Mode II. The non-patent document 1, listed above, discloses the concept of a method of estimating the fatigue limit maximum contact pressure, which is the maximum contact pressure and at which no subsurface-originating flaking failure occurs, from the maximum size of the previously discussed non-metallic inclusion. Specifically, as disclosed in FIG. 13 of the non-patent document 1 listed above and referred to above, where the Hertzian contact pressure migrates, it is speculated that a disc-shaped cracking of a diameter 2a exists at a depth b/2 (in which b represents the radius of the minor axis of the contact eclipse) at which the amplitude of the orthogonal shear stresses is maximized. This disc-shaped cracking is used as resembling the diameter of the largest intervening element.

According to the non-patent document 1 referred to above, the threshold stress intensity factor range, at which the fatigue cracking does no longer extend, is determined $\Delta K_{IIth}$=3 MPa$\sqrt{m}$ by conducting the unique experiment on the extension of Mode II fatigue cracking. In FIG. 14 of the non-patent document 1, in the case of $\Delta K_{IIth}$=3 MPa$\sqrt{m}$, the coefficient of friction between the cracking surfaces is assumed to be 0.5, and the relation between the maximum contact pressure and the critical cracking diameter 2a indicative of whether or not the fatigue cracking will extend is shown. For example, if 2a=50 μm, the fatigue limit maximum contact pressure is estimated $P_{max\ lim}$=2.5 GPa. However, according to the method discussed above, the coefficient of friction between the cracking surfaces is left unknown and a certain value must be assumed therefor. Also, even the non-patent document 2 listed above discusses the determination of $\Delta K_{IIth}$=13 MPa$\sqrt{m}$ for the threshold stress intensity factor range, at which the fatigue cracking does no longer extend, by conducting the unique experiment on the extension of Mode II fatigue cracking, which value is considerably different from $\Delta K_{IIth}$ addressed in the non-patent document 1 first referred to above.

It is eventually pointed out that when the rolling bearing is used under generally occurring conditions in which water tends to mix in, slide tends to result in and/or energization tends to generate, water or a lubricating agent is often decomposed to develop hydrogen. Such a hydrogen, when penetrates into steel, leads to an early flaking failure. Since hydrogen notably reduce the fatigue strength of steel, cracking tends to be induced and extended within the subsurface, at which the orthogonal shear stresses increase, even under a good condition in which contact elements are separated by an oil film, resulting in the early flaking failure.

In view of the foregoing, as a method of evaluating the hydrogen proofing of the rolling bearing, various methods have been contemplated, including a testing method in which the rolling bearing is rapidly accelerated and decelerated (as disclosed in the patent document 5 listed above); a testing method in which the rolling bearing is operated while saline water is sprayed onto such bearing (as disclosed in the patent document 6 listed above); a method in which the bearing assembly is operated within a bath of a lubricant oil mixed with water (as disclosed in the patent document 7 listed above); a method in which the rolling bearing is operated while an electric current is constantly supplied therethrough (as disclosed in the patent document 8 listed above); and a hydrogen resistance evaluating method in which following an ultrasonic axial load fatigue test (under completely reversed stress) in which an extremely high speed vertical load can be loaded after hydrogen has been charged, fatigue is induced before hydrogen gets scattered and lost (as disclosed in the patent document 9 listed above).

Also, the non-patent document 6 listed above reports that as a result of an ultrasonic axial load fatigue test conducted after a test piece of a bearing steel, identified by SUJ2 according to the Japanese Industrial Standards, has been charged with a catholyte hydrogen for a certain time while the current density is varied, the fatigue strength at $10^7$ times decreases with increase of the amount of diffusible hydrogen, indicating a linear relation found therebetween. This suggests that the amount of diffusible hydrogen is a governing factor that leads to the decrease of the fatigue strength, indicating that the original hydrogen resistance evaluation by controlling the amount of hydrogen penetration is required as the first step.

SUMMARY OF THE INVENTION

In view of the foregoing, the present invention has for its essential object to provide a method of and an apparatus for quickly and accurately assessing the shear fatigue property of a metallic material that is liable to a rolling contact.

A method of assessing the shear fatigue property of a rolling contact metallic material, designed in accordance with the present invention, includes a testing step of determining a relation between a shear stress amplitude of the metallic material and the number of loadings by means of an ultrasonic torsional fatigue test; and a shear fatigue strength determining step of determining a shear fatigue strength $\tau_{lim}$ within an ultra long life regime from the determined relation between the shear stress amplitude and the number of loadings in accordance with a predetermined standard.

It is to be noted that the wording "shear fatigue strength within the ultra long life regime" referred to hereinabove and hereinbelow is analogous to the "shear fatigue limit", but in describing the present invention in the specification herein set forth, the wording in question is employed rather than the latter term.

Also, the "predetermined standard" referred to above and employed in the practice of the shear fatigue strength determining step is rendered to be a process of determining a curve by applying the relation of the test result between the shear stress amplitude and the number of loadings to an established theoretical curve descriptive of the shear fatigue strength and then determining the shear fatigue strength from such curve. More specifically, the S-N diagram (the fatigue strength diagram at 50% of the fracture probability), which is determined by applying to a fatigue limit type line chart of the metallic material fatigue reliability evaluating standards JSMS-SD-6-02 stipulated by the Society of Materials Science, Japan (JSMS) can be used. However, this is not necessarily limited to the fatigue limit type line chart model and the S-N diagram may be determined by applying to a continuously decreasing type line mode. It is, however, to be noted that in such case, the parameter $\tau_{lim}$ need be defined as the "value on the S-N diagram at $10^{10}$ times".

According to the above described method, since the fatigue test is carried out by means of the ultrasonic torsional fatigue test in which an excitation frequency or an oscillating frequency reaches an ultrasonic range, in assessing the shear fatigue property of the rolling contact metallic material the required number of loading is attained in a matter of minutes and the shear fatigue property can be quickly assessed. By way of example, if continuously oscillated at 20,000 Hz, the number of loadings of $10^9$ attains only in half a day. Also, since the test is conducted in which the shear fatigue fracture is actually caused, as compared with the conventional method in which the maximum size of a non-metallic inclusion is used as a standard for the quality of steel, the shear fatigue property can be accurately determined.

The stress governing the fatigue fracture of the material is, when you get to the core of it, either the normal stress or the shear stress. In order to evaluate the fatigue property, brought about by the normal stress, at a high speed, some years have already passed since the ultrasonic axial load fatigue testing machine (under completely reversed stress) was made available in the commercial market. In contrast thereto, little studies on the ultrasonic torsional fatigue test for assessing the shear fatigue property at a high speed have been conducted and material hitherto evaluated is a mild steel and an aluminum alloy, in which the maximum shear stress amplitude (completely reversed stress) is equal to or lower than 250 MPa. The present invention has now make it possible to realize the quick assessment of the shear fatigue property under such a technical standard by causing a shear fatigue fracture of a metallic material, which will become a bearing ring and/or a rolling element of the rolling bearing assembly, by applying torsional vibrations which will become the oscillating frequency within the ultrasonic wave region.

The ultrasonic torsional fatigue test may be chosen to be a completely reversed torsional fatigue test, in which torsions in respective directions of positive and reversed rotations relative to the test piece are symmetrical to each other. The metallic material referred to above may be a rolling bearing steel, which will become a bearing ring and/or a rolling element of the rolling bearing assembly.

In the practice of the above described assessing method, during the test step referred to above a plurality of the ultrasonic torsional fatigue tests may be carried out to determine a plurality of relations between the shear stress amplitude of the metallic material and the number of loadings and, during the shear fatigue strength determining step referred to above, a P-S-N diagram of an arbitrarily chosen fracture probability may be determined from the relation between the shear stress amplitude and the number of loadings, determined during the plurality of the test steps, and from this P-S-N diagram the shear fatigue strength $\tau_{lim}$ within the ultra long life regime may be determined. The dimensional effect that appears during the fatigue test having the above described stress gradient is brought about by a mechanical factor of the stress gradient and a statistical factor that the volume (control volume) tending to receive a large load increases and decreases. In terms of the statistical factor, it is recommended to obtain the P-S-N diagram by conducting a plurality of evaluation at a plurality of stress standards.

In this case, during the shear fatigue strength determining step referred to above, the value of 85% relative to the shear fatigue strength within the ultra long life regime determined from the P-S-N diagram may be rendered to be a value of the shear fatigue strength $\tau_{lim}$ that is used during the fatigue limit maximum contact pressure calculating step. For the purpose of the safest estimation, in a manner described above, a value, which is 80% of the value of 85% of the shear fatigue strength within the ultra long life regime determined from the P-S-N diagram, may be rendered to be a value of the shear fatigue strength $\tau_{lim}$ that is used during the fatigue limit maximum contact pressure calculating step.

In the practice of the assessing method referred to above, in order to safely estimate the absolute value of the shear fatigue strength, the absolute fatigue strength $\tau_{lim}$, that is determined by combining two or more of a fracture probability correction (a), an excessive evaluation correction (b) and a dimensional effect correction (c). The fracture probability correction (a) obtains an arbitrary chosen P-S-N diagram descriptive of an arbitrary fracture probability, which diagram is determined from the relation between the shear stress amplitude and the number of loadings, obtained through the test, and renders the shear fatigue strength within the ultra long life regime to be the shear fatigue strength $\tau_{lim}$ within the ultra long life regime for use in evaluating the shear fatigue strength. The excessive evaluation correction (b) is a correction to render the value of 85% relative to the shear fatigue strength within the ultra long life regime, that is determined from the relation between the shear stress amplitude and the number of loadings, obtained through the test, to be the shear fatigue strength $\tau_{lim}$ within the ultra long life regime for use in evaluating the shear fatigue strength. The dimensional effect correction (c) is a correction to render the value of 80% relative to the shear fatigue strength within the ultra long life regime, that is determined from the relation between the shear stress amplitude and the number of loadings, obtained through the test, to be the shear fatigue strength $\tau_{lim}$ within the ultra long life regime for use in evaluating the shear fatigue strength, may be regarded as the absolute value. As described above, by combining the two or more corrections, the shear fatigue strength is safely estimated to ensure a further safe estimation of the fatigue limit maximum contact pressure.

According to the present invention, the use is made of the ultrasonic torsional fatigue test capable of being loaded at a high speed and specifically the ultrasonic torsional fatigue test is carried at an extremely high speed of, for example 20,000 Hz in oscillating frequency. Accordingly, if continuously oscillated, the number of loadings of $10^9$ is attained only in half a day. However, the test piece tends to emit heat, when continuously oscillated at a little high shear stress amplitude, and it is hence impossible to determine the relation between the shear stress amplitude and the number of loadings that is somewhat accurate. For this reason, it is preferred that the test piece be forcibly cooled with air. In the event that only the forced air cooling is insufficient to suppress the heat emission from the test piece, oscillation and break are preferably alternately repeated. Although the break results in reduction of the substantial load frequency, the use of the ultrasonic torsional fatigue testing machine of 20,000 Hz in oscillating frequency can achieve, if the interval between the break and the oscillation that is about 10 times is chosen, still high speed of 2000 Hz, and as a result, the number of loadings of $10^9$ can be attained if one week is made available.

In the practice of the above described assessing method, the ultrasonic torsional fatigue test is carried out by the use of, for example, a torsional vibration converter for generating torsional vibrations, which will become positive and reversed rotations about the axis of rotation when an electric alternating power is applied, and an amplitude amplifying horn having a tip end, provided with a mounting portion to which the test piece is fitted coaxially and also having a base end that is fixed to the torsional vibration converter, and operable to amplify the amplitude of the torsional vibration of the vibration converter applied to the base end, in which the shape and the dimensions of the amplitude amplifying horn are chosen to be the shape and the dimensions enough to resonate with the torsional vibrations resulting from the drive of the torsional vibration converter and the vibration converter is driven at a frequency within the ultrasonic wave region to resonate the test piece with the vibration of the amplitude amplifying horn to thereby accomplish the shear fatigue fracture. The amplifier referred to above may be such that the magnitude of an output thereof and the ON or OFF state thereof can be controllable in response to an input from the outside. It is to be noted that the term "frequency within the ultrasonic wave region or ultrasonic range" used hereinbefore and hereinafter in this specification is intended to broadly mean the frequency region or frequency range of sound waves of 16,000 Hz or higher.

The lowermost limit value of the frequency, at which the torsional vibration converter is driven, may be chosen to be (20,000−500+α) Hz and the uppermost limit value thereof is chosen to be (20,000+500) Hz, noting that α represents a spare value relative to a change in property of the test piece during the test and not higher than 200 Hz. When the lowermost limit value of the frequency is chosen to be (20,000−500+α) Hz and the uppermost limit value thereof is chosen to be (20,000+500) Hz and the test is carried out with the torsional vibration converter being operated at the maximum executable output, it is possible to avoid the occurrence of the instable resonance.

Where the lowermost and uppermost limit values of the frequency referred to above are such frequencies as described above, the spare value referred to above may be 200 Hz. Also, when the test to induce the shear fatigue fracture is carried out by causing the test piece to resonate with the vibration of the amplitude amplifying horn, it is preferred that the amplitude amplifying horn is caused to resonate with the vibrations of the torsional vibration converter. In such case, the amplitude amplifying horn may be of a transverse sectional shape that is round and the longitudinal sectional shape thereof excluding the base end portion is preferred to be of a tapered shape. By so choosing such shape, the amplitude amplification can effectively takes place.

In the practice of the assessing method of the present invention, the test piece is preferably of a dumbbell shape including cylindrical shoulder portions at opposite ends thereof and a narrowed intermediate portion continued from the shoulder portions at the opposite end thereof and having an axial sectional shape depicted by an arcuate curve. If the test piece is of the dumbbell shape, it is easy to induce the shear fatigue fracture at the narrowed intermediate portion. The test piece is needed to resonate and, for this purpose, it is necessary to properly design the shapes and dimensions of various ports.

In order to design and make the test piece of the shape and dimensions proper to induce the resonance, the following method is desirable:

Let it be assumed that the length of each of the shoulder portions is expressed by $L_1$ (m in unit), the half chord length, which is half the length of the narrowed intermediate portion, is expressed by $L_2$ (m in unit), the radius of each of the shoulder portions is expressed by $R_2$ (m in unit), the minimum radius of the narrowed intermediate portion is expressed by $R_1$ (m in unit), the radius of the arcuate curve is expressed by R (m in unit and determined from $R_1$, $R_2$ and $L_2$), the resonance frequency is expressed by f (Hz in unit), the Young modulus is expressed by E (Pa in unit), the Poisson's ratio is expressed by ν (dimensionless), the density is expressed by ρ (kg/m³ in unit); and the parameters $L_2$, $R_1$ and $R_2$ are arbitrarily chosen values, and the frequency f is an arbitrarily chosen value within the frequency range of 20,000±500 Hz at which the torsional vibration converter can be driven; a plurality of test piece shape models having different values of the parameters $L_2$, $R_1$, $R_2$ and R as well as the shoulder portion length slightly shortened than $L_1$ determined as a theoretical solution are prepared by determining the shoulder portion length $L_1$, for which the test piece resonates at the resonance frequency f, from the following equations (1) to (6) as the theoretical solution; and an analytic solution $L_{1N}$, in which the torsional resonance occurs at the resonance frequency f, is determined by means of an eigen value analysis of a free torsional resonance by means of a finite element analysis, using, for each of those shaped models, an actually measured physical value of a metallic material with the Young modulus E, the Poisson's ratio ν and the density ρ taken as respective physical values and test pieces having the dimensions of $L_2$, $R_1$, $R_2$, R and $L_{1N}$ are prepared and used in a test:

$$E = \frac{G}{2(1+v)} \quad (1)$$

$$\omega = 2\pi f \quad (2)$$

$$\alpha = \frac{1}{L_2}\text{Arccosh}\left(\frac{R_2^2}{R_1^2}\right) \quad (3)$$

$$k = \omega\sqrt{\frac{\rho}{G}} \quad (4)$$

$$\beta = \sqrt{\alpha^2 - k^2} \quad (5)$$

$$L_1 = \frac{1}{k}\text{Arctan}\left[\frac{1}{k}\{\beta\coth(\beta L_2) - \alpha\tanh(\alpha L_2)\}\right] \quad (6)$$

Although the test piece having the shoulder portion length $L_1$, determined as the theoretical solution, and also having the dimensions $L_2$, $R_1$, $R_2$ and R may be prepared and tested, it may occur that no resonance occurs. In such case, a plurality of test piece shape models having different values of the parameters $L_2$, $R_1$, $R_2$ and R as well as the shoulder portion length slightly shortened than $L_1$ determined as a theoretical solution are prepared and, with respect to those shape models, using the parameters E, ν and ρ as the actually measured physical values of the metallic material used as the test piece, the analytic solution $L_{1N}$ that resonates at the resonance frequency f is determined by means of an eigen value analysis of the free torsional resonance by means of the finite element analysis and, then, the test piece having the dimensions of $L_2$, $R_1$, $R_2$, R and $L_{1N}$ referred to above is prepared and used in the test. With the test piece having the shape and the dimensions as described above, resonance of the test piece occurs.

The torsional vibration converter may have a rated output of 300 W, in which case the capacity of the test piece, excluding a male screw portion of the test piece through which the latter is fitted to an amplitude amplifying horn tip end and a center hole portion at a counter mounting portion end face required for processing the test piece, is chosen to be 1.2× $10^{-6}$ m³ or smaller. In such case, where the end face torsional angle of the test piece is 0.01 rad, with respect to the test piece shaped model excluding the male screw portion, through which it is fitted to a tip end of the amplitude amplifying horn, and the center hole portion at the counter mounting portion end face required for processing it, when the physical value is chosen that E=2.04×$10^{11}$ Pa, ν=0.29 and ρ=7,800 kg/m³, the maximum shear stress, which acts on a surface of a test piece minimum reduced diameter portion and which is determined by the eigen value analysis of the free torsional resonance by means of the finite element analysis is 520 Mpa or higher.

In practice of the assessing method of the present invention, where the test is conducted with the use of the test piece having the dimensions $L_1$, $L_2$, $R_2$, $R_1$ and R of the various portions thereof determined by means of the eigen value analysis of the free torsional resonance by means of the finite element analysis as hereinabove described, when the resonance frequency f is chosen to be within the range of 20,000±500 Hz and the maximum output of the torsional vibration converter is chosen to be 300 W, the weight of the test piece excluding the mounting projection in the form of a mounting male screw portion for securement to the amplitude amplifying horn is preferably chosen to be 9.36 gram or smaller. Even when the test piece has the shape and the dimensions capable of resulting in resonance, it may occur that a resonance instability may result in. As a result of studies, it has been found that the resonance instability is greatly affected by the weight of the test piece. Also, where the test piece has the above described shape and dimensions, the resonance frequency is within the range of 20,000±500 Hz and the test is conducted with the maximum output of the torsional vibration converter being 300 W, if the test piece weight is 9.36 gram or smaller, it has been revealed that no resonance instability occur.

Also, in the case where the test piece weight is chosen to be 9.36 gram or smaller, it is preferred that the actually measured value of the end face torsional angle of the test piece, when at 90% of the output of the amplifier, attains a value of 0.018 rad or higher, and the maximum shear stress acting on the surface of the test piece smallest diameter portion attains 951 MPa or higher, when an end face torsional angle is 0.018 rad, determined by the eigen value analysis of the free torsional resonance by menas of the finite element analysis.

In the practice of the assessing method of the present invention, the shear fatigue property of the metallic material under the hydrogen penetration can be evaluated by means of the ultrasonic torsional fatigue test to the test piece after the hydrogen charging has been applied to the test piece.

According to the shear fatigue property assessing method under the hydrogen penetration, since the torsional fatigue test, in which the ultrasonic torsional vibration, which the oscillating frequency will become within the ultrasonic wave region, is applied to the test piece, the torsional fatigue test can be carried out in which extremely high speed loading is repeatedly applied. For this reason, before the charged hydrogen is scattered and lost, the shear fatigue is applied to the test piece of the metallic material that is subject to evaluation and the shear fatigue property under the hydrogen penetration can be reasonably and quickly evaluated. By way of example, if continuously oscillated at the frequency of 20,000 Hz, the number of loadings of $10^7$ can be attained in about 9 minutes.

The hydrogen charging referred to above may be carried out by means of a catholyte charging. For the catholyte charging, an aqueous solution of dilute sulfuric acid may be employed. In such case, in order to increase the hydrogen charging efficiency, thiourea may be added as a catalyst poison to the aqueous solution of dilute sulfuric acid. The amount of the thiourea to be added is preferably up to 1.4 gr/L.

Where the hydrogen charging is carried out by means of the catholyte charging, an aqueous solution of sodium chloride may be employed for the catholyte charging. In such case, in order to increase the hydrogen charging, ammonium thiocyanate may be added as a catalyst poison to the aqueous solution of sodium chloride. The amount of the ammonium thiocyanate to be added is preferably up to 3 gr/L.

Also, where the hydrogen charging is carried by means of the catholyte charging, an aqueous solution of sodium hydrate may be employed for the catholyte charging. In such case, in order to increase the hydrogen charging efficiency, sodium sulfide nonahydrate may be added as a catalyst poison to the aqueous solution of sodium hydrate. The amount of the sodium sulfide nonahydrate to be added is preferably up to 1 gr/L.

Yet, the hydrogen referred to above may be charged by immersing it in an aqueous solution. In this case, hydrogen may be charged by immersing it in an aqueous solution of ammonium thiocyanate. The concentration of the ammonium thiocyanate is preferably up to 20 mass %.

An apparatus for assessing the shear fatigue property of the metallic material that undergoes a rolling contact, which apparatus is designed in accordance with the present invention, includes an input unit for storing a relation between the shear stress amplitude of the metallic material and the number of loadings, determined by means of an ultrasonic torsional fatigue test, in a predetermined storage area, and a shear fatigue strength determining unit for determining the shear fatigue strength within the ultra long life regime from the stored relation between the shear stress amplitude and the number of loadings in accordance with a predetermined standard. When this shear fatigue property assessing apparatus is used, the previously described shear fatigue property assessing method can be enforced.

In the assessing apparatus, the metallic material referred to above may be a rolling bearing steel for bearing rings and/or rolling elements of a rolling bearing assembly. The input unit referred to previously is operable to store, for example, a file, in which the relation between the shear stress amplitude of the metallic material and the number of loadings is summarized, in a predetermined storage area or in a manner readily to specify a storage site, for subsequent calculation by the use of the manual input device such as, for example, a keyboard, a read-out device for a recording medium and/or a communication network.

In this assessing apparatus, the use is made of a torsional vibration converter for generating torsional vibrations, which will become positive and reversed rotations about the axis of rotation when an electric alternating power is applied, an amplitude amplifying horn having a tip end, provided with a mounting portion to which the test piece is fitted coaxially and also having a base end that is fixed to the torsional vibration converter, and operable to amplify the amplitude of the torsional vibration of the vibration converter applied to the base end, an oscillator, an amplifier for amplifying an output of the oscillator and then applying it to the torsional vibration converter, and a control and data collecting unit for applying an input of the control to the amplifier and collecting data including an excitation frequency, state of the amplifier and the number of loadings, in which the shape and the dimensions of the amplitude amplifying horn are chosen to be the shape and the dimensions enough to resonate with the torsional vibrations resulting from the drive of the torsional vibration converter, the shape and the dimensions of the test piece are chosen to be the shape and the dimensions enough to resonate with the torsional vibrations of the amplitude amplifying horn, and a test is preferably conducted to cause a shear fatigue fracture in the test piece by driving the vibration converter at a frequency region within the ultrasonic wave region and causing the amplitude amplifying horn and the test pieces to resonate.

The lowermost limit value of the frequency, at which the torsional vibration converter is driven, may be chosen to be $(20,000-500+\alpha)$ Hz, in which case the uppermost limit value thereof is $(20,000+500+\alpha)$ Hz, noting that $\alpha$ represents a spare value relative to a change in property of the test piece during the test and not higher than 200 Hz.

The torsional vibration converter preferably generates torsional vibrations that are completely reversed, in which the direction of the positive rotation and the direction of the reversed rotation are symmetrical to each other. Also, the amplitude amplifying horn is preferably of a type capable of resonating with the vibrations caused by the oscillation frequency of the torsional vibration converter during the test. In such case, the amplitude amplifying horn is of a design in which the transverse sectional shape thereof is round and the longitudinal sectional shape excluding the base end portion thereof is of a tapered shape expressed by an exponential function. With such shape so chosen, the amplitude amplification, takes place effectively.

The method of estimating the fatigue limit maximum contact pressure of the rolling contact metallic material is a method of estimating the fatigue limit maximum contact pressure with the use of the assessing method of the present invention and further includes a fatigue limit maximum contact pressure calculating step of obtaining the maximum orthogonal shear stress amplitude $\tau_0$, which acts inside a subsurface of an object of the previously described metallic material and which is determined by the shape and the dimensions of contact surfaces of the object made of the metallic material and of another object rollingly contacting the object as well as a load for applying a contact pressure, and then determining the maximum contact pressure $P_{max}$, at which the load equal to the shear fatigue strength $\tau_{lim}$ acts, according to a predetermined equation, to render this maximum contact pressure $P_{max}$ to be an estimated value of the fatigue limit maximum contact pressure $P_{max\ lim}$.

The "predetermined equation" used during the execution of the fatigue limit maximum contact pressure calculating step referred to above is disclosed in the non-patent document 3 listed above. FIG. 5.13 of the non-patent document 3 shows a circumferential distribution of the orthogonal shear stresses acting on the contact surface in a line contact condition at the depth, at which such orthogonal shear stresses is maximized, indicating that the value, which is four times the maximum orthogonal shear stresses $\tau_0$ is equal to the maximum contact pressure $P_{max}$. Accordingly, in the case of the metallic material in the line contact condition, the following equation establishes:

(Fatigue limit maximum contact pressure $P_{max\ lim}$)= 4×(Shear fatigue strength $\tau_{lim}$)

In the rolling bearing assembly, if the fatigue limit maximum contact pressure can be estimated by conducting the torsional fatigue test of the material to be used for each of, for example, sellers and/or each of production lots, it is effective in increasing the reliability. However, with the conventional technique, the torsional fatigue test requires a substantial length of time as hereinabove described and it has been substantially impossible to estimate the fatigue limit maximum contact pressure of the material to be used. Accordingly, there has not been an idea that the fatigue limit maximum contact pressure is used as one of test items of the bearing material.

However, according to the estimating method, since the fatigue test is carried out by means of the ultrasonic torsional fatigue test, an extremely high speed loading is possible and the relation between the shear stress amplitude of the metallic material and the number of loadings can be determined in a matter of minutes. Since the shear fatigue strength $\tau_{lim}$ within the ultra long life regime is determined from the relation so determined and the maximum contact pressure $P_{max}$ is determined from the contact dimensions and specification of the metallic material at the time the load acts, in which the maximum orthogonal shear stress amplitude $\tau_0$ then acting within a subsurface becomes equal to the shear fatigue strength $\tau_{lim}$. Since the maximum contact pressure $P_{max}$ so determined is estimated as the fatigue limit maximum contact pressure $P_{max\ lim}$ the fatigue limit maximum contact pressure $P_{max\ lim}$ can be accurately estimated from the result of the torsional fatigue test. For this reason, when the fatigue limit maximum contact pressure $P_{max\ lim}$ of the rolling bearing steel, which is a material having a high shear fatigue strength $\tau_{lim}$, is to be estimated, an effect that the test can be performed in a matter of minutes can be further effectively exhibited.

Also, as hereinabove described, the ultrasonic torsional fatigue testing machine capable of evaluating at the large maximum shear stress amplitude has not been made available in the past, but the present invention has been devised on the basis of the development of the ultrasonic torsional testing machine, the finding that the maximum contact pressure $P_{max}$ at the time the load acts in which the maximum orthogonal shear stress amplitude $\tau_o$ acting within the subsurface becomes equal to the shear fatigue strength $\tau_{lim}$ can be estimated as the fatigue limit maximum contact pressure $P_{max\ lim}$, and the comprehensive and accurate efforts.

The apparatus for estimating a fatigue limit maximum contact pressure of the rolling contact metallic material designed in accordance with the present invention is an apparatus for estimating the fatigue limit maximum contact pressure with the use of the assessing apparatus of the present invention, which further includes a fatigue limit maximum contact pressure calculating unit for obtaining the maximum orthogonal shear stress amplitude $\tau_0$ which acts within a subsurface of an object of the previously described metallic material and which is determined by the shape and the dimensions of contact surfaces of the object made of the metallic material and of another object rollingly contacting the object as well as a load for applying a contact pressure, and then determining the maximum contact pressure $P_{max}$, at the time the load acts in which the maximum orthogonal shear stress amplitude $\tau_0$ is equal to the shear fatigue strength $\tau_{lim}$, according to a predetermined equation, to render this maximum contact pressure $P_{max}$ to be an estimated value of the fatigue limit maximum contact pressure $P_{max\ lim}$.

According to this estimating apparatus, in a manner similar to what has been explained in connection with the method of estimating the fatigue limit maximum contact pressure, the ultrasonic torsional fatigue test capable of loading, which is extremely high speed, can be used and the relation between the shear stress amplitude of the rolling bearing steel and the number of loadings is determined in a short period of time and the fatigue limit maximum contact pressure $P_{max\ lim}$ can be accurately calculated.

Where it can be deemed to be a linear contact, the predetermined equation used by the fatigue limit maximum contact pressure calculating unit is as follows:

(Fatigue limit maximum contact pressure $P_{max\ lim}$)= 4×(Shear fatigue strength $\tau_{lim}$)

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

FIG. 1D is a sectional view showing an object, which is made of a metallic material forming a test piece to be examined, and another object contacting such first mentioned object;

FIG. 2 is a block diagram showing the system for estimating the shear fatigue property;

FIG. 17 is an explanatory diagram used to explain the distribution of the orthogonal shear stress $\tau_{yz}$ in a circumferential section within a subsurface and the normal stress $\sigma_z$ in the direction of depth, when $P_{max}$=1,500 MPa acts under a line contact condition;

FIG. 18 is a micrograph showing the section, taken in a circumferential direction, indicating the presence of parallel minute cracks appearing in the surface about at a depth at which the absolute value of the orthogonal shear stress is maximal;

FIG. 19 is an explanatory diagram showing a display of a control device used in the ultrasonic torsional fatigue testing machine, illustrating an example of testing condition input screen;

DETAILED DESCRIPTION OF THE PREFERRED EMBODIMENTS

Figure 1A:
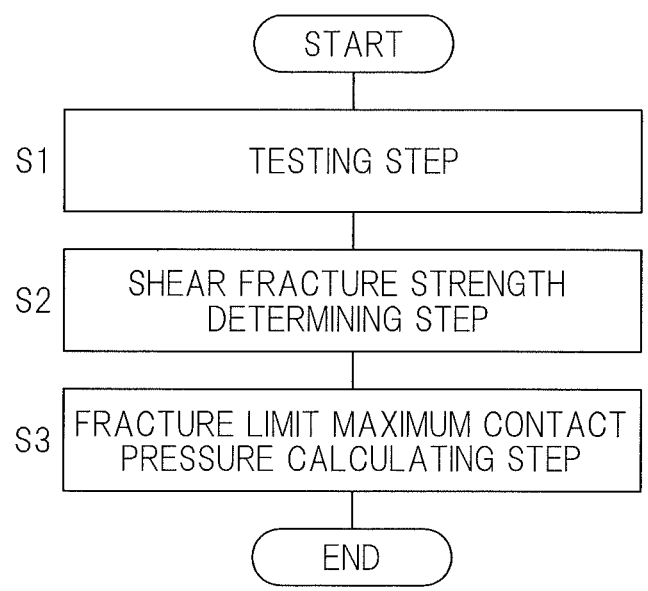
FIG. 1A is a flowchart showing a method of assessing the shear fatigue property according to a first preferred embodiment of the present invention.

The present invention will now be described in detail in connection with a first preferred embodiment thereof. It is to be noted that the description that follows is to be understood as including that on a method of selecting a rolling contact metal material. A method of assessing the shear fatigue property of the rolling contact metal material is a method of estimating the shear fatigue strength $\tau_{lim}$ of a metallic material of a kind that undergoes a rolling contact, and includes, as shown in FIG. 1A, a testing step S1 and a shear fatigue strength determining step S2. In the first embodiment, the description is made as a method of estimating the fatigue limit maximum contact pressure, in which a fatigue limit maximum contact pressure calculating step S3 of estimating the fatigue limit maximum contact pressure $P_{max\,lim}$ of the rolling contact metal material from the shear fatigue strength $\tau_{lim}$ determined by the method of assessing the shear fatigue property of the rolling contact metal material. The term "rolling contact metal material" referred to hereinbefore and hereinafter is intended to mean a metallic material which will be used to form, for example, bearing rings and/or rolling elements used in a rolling bearing assembly. Examples of this metallic material includes, inter alia, SUJ2, SCr420, M50, M50NiL, SNCM420, SUJ3, SCr420, S53C, SUS440C and so on, all of which are defined in the Japanese Industrial Standards, JIS for short. It is eventually to be noted that SUJ2 material corresponds to SAE52100 as defined in the American Iron and Steel Institute (AISI) standards.

Figure 1B:
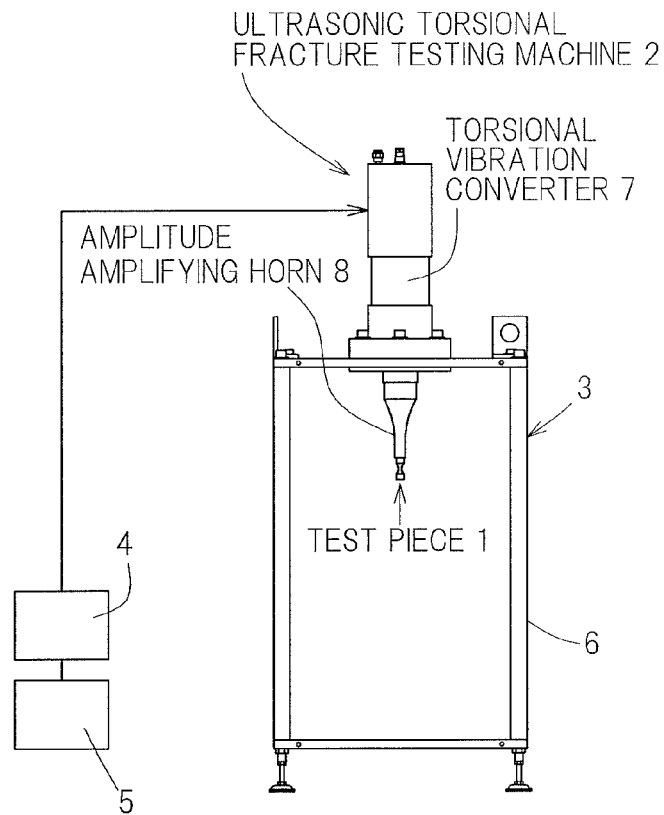
FIG. 1B is a schematic diagram showing a system for estimating the shear fatigue property.

The testing step S1 is a step of determining the relation between the shear stress amplitude of the metallic material and the number of loadings through an ultrasonic torsional fatigue test under completely reversed torsion. This test makes use of a ultrasonic torsional fatigue testing machine 2 capable of applying ultrasonic torsional vibrations under completely symmetrical reversed torsion in positive and reversed directions to a test piece 1 of the metallic material shown in FIG. 1B. The ultrasonic torsional fatigue testing machine 2 conducts the ultrasonic torsional fatigue test (under completely reversed torsion) with an extremely high oscillating frequency of 20,000 Hz. This ultrasonic torsional fatigue testing machine 2 is of a type improvements have been made on this occasion since any ultrasonic torsional fatigue testing machine currently available in the commercial market cannot be used for the purpose of the present invention.

Figure 1C:
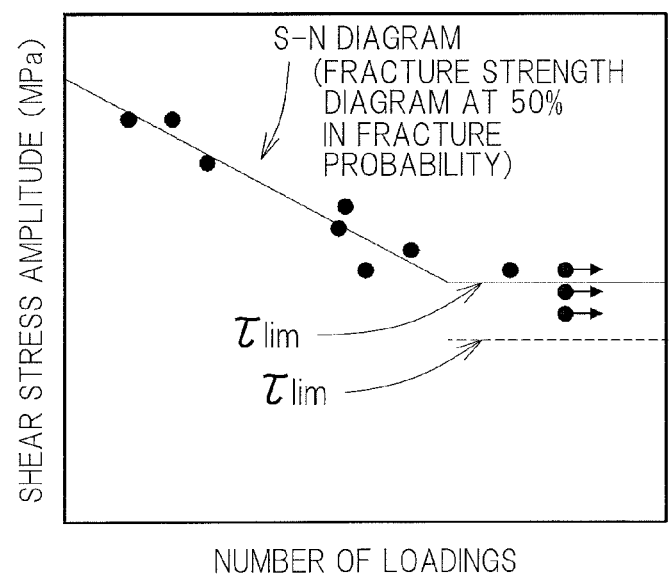
FIG. 1C is an explanatory diagram showing fatigue strength diagram and shear fatigue strength $\tau_{lim}$.

The shear fatigue strength determining step S2 determines the shear fatigue strength $\tau_{lim}$ in the ultra long life regime, according to a prescribed rule, from the relation between the shear stress amplitude and the number of loadings that is determined at the testing step S1. It is to be noted that the term "shear fatigue strength in the ultra long life regime" means the shear fatigue limit, but in the specification hereby presented, the shear fatigue limit in question is expressed by the term "shear fatigue strength in the ultra long life regime". The term "prescribed rule" referred to hereinbefore is rendered to be, for example, a process of determining a curve by applying the relation between the shear stress amplitude and the number of loadings forming the result of test to the established theoretical curve indicative of the shear fatigue strength, and then determining the shear fatigue strength from such curve. More specifically, the S-N diagram (the fatigue strength curve at 50% of fracture probability), as shown in FIG. 1C, can be used, which has been obtained by applying to a model of the fatigue limit type line chart stipulated in Kinnzoku-zairyo Hiro Shinraisei Hyoka Hyojun (Fatigue Reliability Evaluating Standards of Metallic Materials) JSMS-SD-6-02 of Nippon Zairyo Gakkai (Japan Society of Materials). It is however to be noted that the curve may be determined by applying not only the fatigue limit type line chart, but also a continuously decreasing curve model to determine the S-N diagram. In such case, it is necessary to be defined as, for example, "$\tau_{lim}$ is a value found in the S-N diagram when the number of loadings is $10^{10}$ times."

Figure 21:
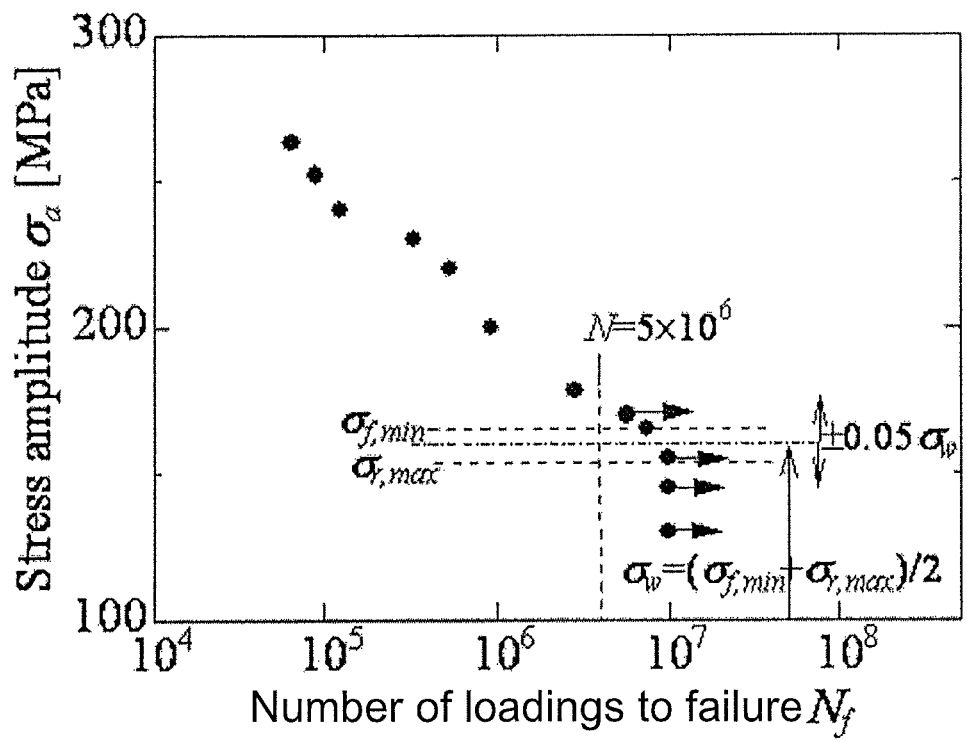
FIG. 21 is a chart showing results of the fatigue test conducted to determine the fatigue limit.

The model of the fatigue limit type line chart stipulated in Kinnzoku-zairyo Hiro Shinraisei Hyoka Hyojun (Fatigue Reliability Evaluating Standards of Metallic Materials) JSMS-SD-6-02 of Nippon Zairyo Gakkai (Japan Society of Materials), when applied to the following equations, recurs.

$$\sigma = -A\,\log_{10} N + B\,(N < N_w)$$

$$\alpha = E\,(N \geq N_w)$$

in which A, B, E, $N_w$ represent constants. The fatigue limit (E in the above equation) is estimated as follows particularly where 1 point or more of cut-off data at the number of loadings of $10^6$ or more exist. The average value of the failure data stress minimum value $\sigma_{f\,min}$ and the cut-out data stress maximum value $\sigma_{f\,max}$ of a lower stress than $\alpha_{f\,min}$ is defined as the fatigue limit. In this respect, see FIG. 21. It is to be noted that where there are the cut-off data of the same stress level as $\sigma_{f\,min}$ and no cur-off data exist at the stress level lower than $\sigma_{f\,min}$, $\sigma_{f\,min}$ is defined as the fatigue limit. After the fatigue limit is defined this way, this value is fixed and the other parameters in the above equations are then estimated from the failure data. The continuously decreasing curve model is recurred by applying it to the following Stromeyer's fundamental equation:

$$\sigma = 10^{-A\,log_{10}N+B} + D$$

wherein A, B and D represents constants.

Figure 22:
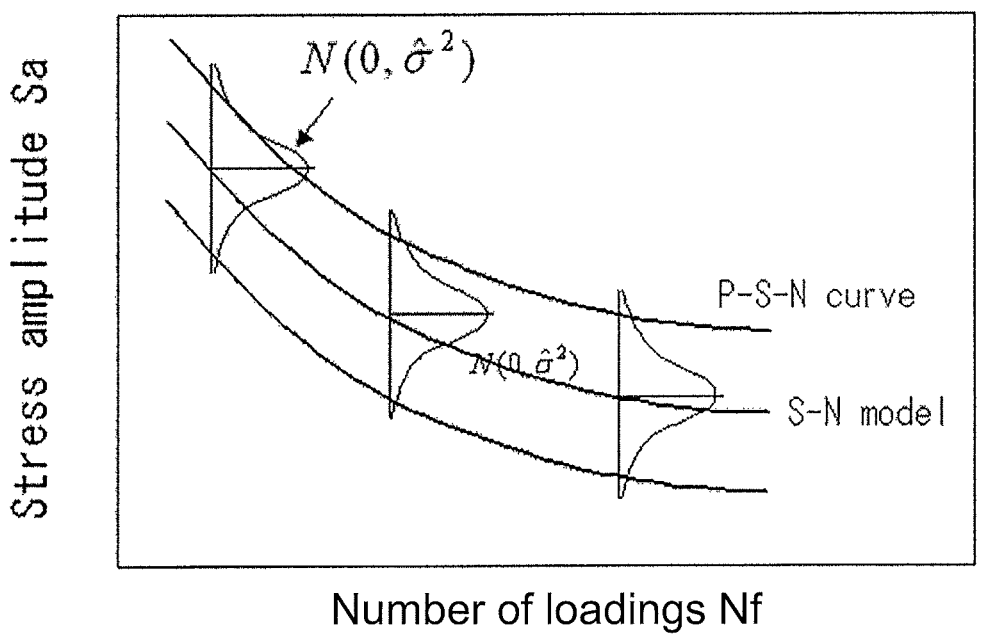
FIG. 22 is a chart indicating that in accordance with a normal distribution of strengths at an arbitrary number of loadings matches with the standard deviation.

The fatigue strength and the fatigue life have variations. The stochastic fatigue property is originally assessed by a plurality of test pieces at a plurality of stress amplitudes or is assessed by determining the P-S-N diagram at the fracture probability. In this respect, see the non-patent document 5 listed above. However, determination of the P-S-N diagram requires a substantial number of process steps and a substantial amount of time. The metallic material fatigue reliability evaluating standards JSMS-SD-6-04 recommends the method of determining the P-S-N diagram in the arbitrary fracture probability. According to it, the standard deviation a of the strength distribution is assumed to be constant according to the normal probability distribution of the strength distribution in the arbitrary chosen fatigue life as shown in FIG. 22.

Figure 23:
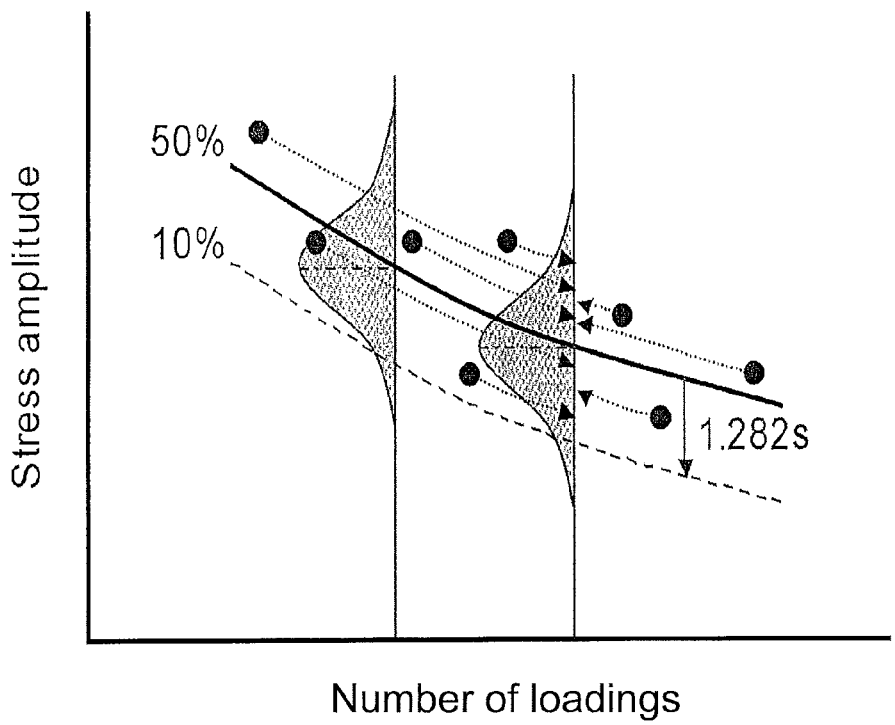
FIG. 23 is a chart showing how to determine the P-S-N diagram (the fracture probability is 50% in the case of a curve line model of a continuously lowering type)

The S-N diagram so obtained is defined as a fatigue strength curve of 50% in fracture probability. The fatigue limit line model aims at the failure data on fatigue strength at finite life curves (inclined linear line) and the continuously lowering curve model aims at the entire range of failure data. FIG. 23 illustrates an example of the continuously lowering curve mode. The standard deviation is determined by translating the individual failure data to the arbitrary fatigue life along a linear line or a curve to exhibit the normal probability distribution. For example, assuming that the standard deviation so obtained is expressed by s, the fatigue strength curve of 50% in fracture probability, which has been translated only 1.282s downwardly, becomes the P-S-N diagram of 10% fracture probability.

During the fatigue limit maximum contact pressure calculating step S3 referred to previously, the maximum contact pressure $P_{max}$ is defined as an estimated value of the fatigue limit maximum contact pressure $P_{max\,lim}$. The maximum contact pressure $P_{max}$ is determined according to a predetermined equation, at the time the load acts in which the maximum orthogonal shear stress amplitude $\tau_0$ is equal to the shear fatigue strength $\tau_{lim}$. The maximum orthogonal shear stress amplitude $\tau_0$ acts within the subsurface of an object M1 of the metallic material and is determined by the contact surface dimension and specification (shape and dimensions) between the object M1 (as shown in FIG. 1D) and an object M2 rollingly contacting the object M1 as well as the load to apply a contact pressure. The object M1 manufactured with the use of the metallic material referred to previously is bearing rings and/or rolling elements of the rolling bearing assembly where the metallic material is a rolling bearing steel. The rolling bearing assembly may be either a ball bearing assembly or a roller bearing assembly.

Figure 5:
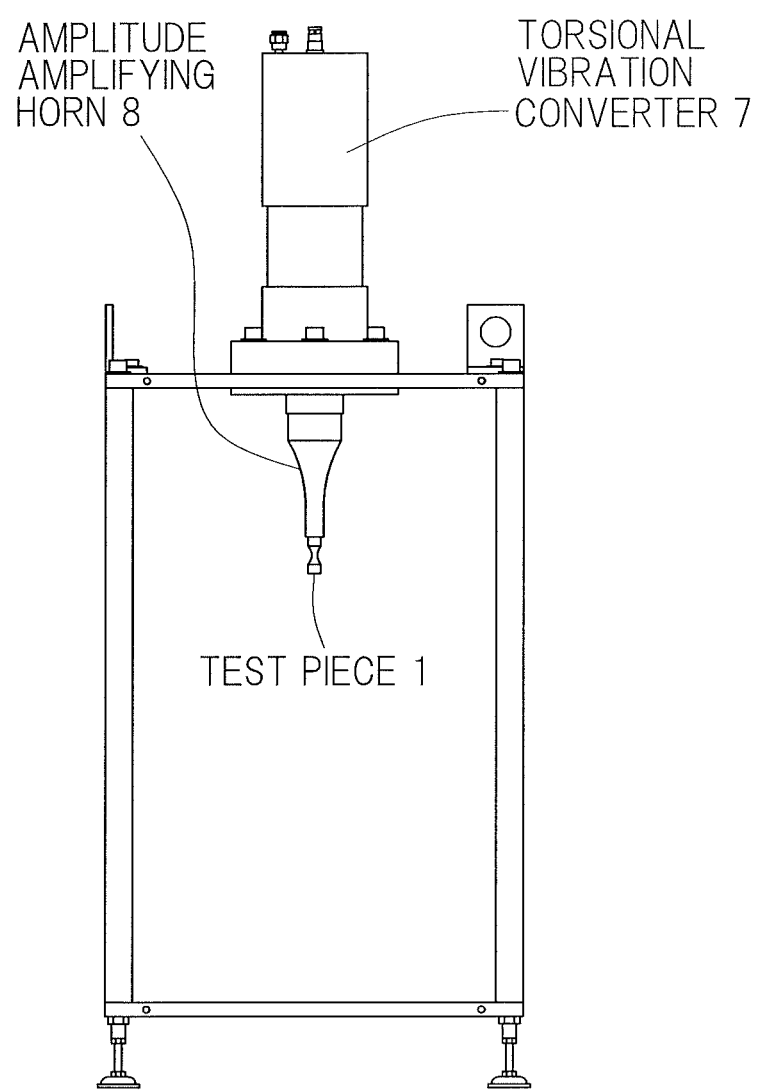
FIG. 5 is a front elevational view showing a body of an ultrasonic torsional fatigue testing machine.

The term "predetermined equation" referred to above and used during the execution of the fatigue limit maximum contact pressure calculating step S3 is disclosed in the previously described non-patent document 3 listed above. FIG. 5.13 of the non-patent document 3 shows a circumferential distribution of the orthogonal shear stresses acting within the subsurface in a line contact condition at the depth, at which such orthogonal shear stresses is maximized, indicating that the value, which is four times the maximum orthogonal shear stresses $\tau_0$ is equal to the maximum contact pressure $P_{max}$. Accordingly, in the case of the line contact condition, the following equation establishes:

(Fatigue limit maximum contact pressure $P_{max\ lim}$)= 4×(Shear fatigue strength $\tau_{lim}$)

When the major axis radius of the contact eclipse is expressed by a and the minor axis radius is expressed by b, in the line contact condition b/a=0, and, in such case, four times the maximum orthogonal shear stress $\tau_o$ equals to $P_{max}$. The proportionality constant of the maximum contact pressure $P_{max}$ and the maximum orthogonal shear stress $\tau_o$ in the case of b/a not equal to 0 is shown in FIG. 5.14 of the non-patent document 3 referred to previously.

With the estimating method according to the preferred embodiment, since the fatigue test is carried out by means of a ultrasonic torsional fatigue test, an extremely high speed loading is possible and the relation between the shear stress amplitude of the metallic material and the number of loading can be determined in a matter of minutes. Since the shear fatigue strength $\tau_{lim}$ in the ultra long life regime is determined from the relation so determined and the maximum contact pressure $P_{max}$ exhibited at the time the load acts, which renders the maximum orthogonal shear stress amplitude $\tau_o$ acting within the subsurface to become equal to the shear fatigue strength $\tau_{lim}$, is estimated as the fatigue limit maximum contact pressure $P_{max\ lim}$ from the contact dimension and specification, the fatigue limit maximum contact pressure $P_{max\ lim}$ can be accurately estimated from the result of the torsional fatigue test. For this reason, where estimation of the fatigue limit maximum contact pressure $P_{max\ lim}$ of the rolling bearing steel, which is a material of a high shear fatigue strength $\tau_{lim}$, is carried out, such an effect that the test can be performed in a matter of minutes as described above can be further effectively enhanced.

In the practice of this preferred embodiment, as hereinabove discussed, by means of the ultrasonic torsional fatigue test under completely reversed torsion of an extremely high speed, say, 20,000 Hz in oscillating frequency, the relation between the number of loading and the shear stress amplitude of the rolling bearing steel is determined in a matter of minutes, the shear fatigue strength (or the shear fatigue limit) $\tau_{lim}$ within the ultra long life regime is determined, and the maximum contact pressure $P_{max}$ at the time the load acts, at which the maximum orthogonal shear stress amplitude $\tau_o$ acting within the subsurface becomes equal to the shear fatigue strength $\tau_{lim}$, is estimated as the fatigue limit maximum contact pressure $P_{max\ lim}$ from the contact dimension and specification of the rolling bearing assembly. By way of example, if it is continuously oscillated at the frequency of 20,000 Hz, $10^9$ loadings are attained only in about half a day. However, since if it is continuously oscillated at a few high shear stress amplitude and the test piece 1 comes to generate heat, the test piece 1 need be cooled and, therefore, a forced air cooling is performed. Where only with the forced air cooling it is insufficient to suppress the heat generation from the test piece 1, oscillation and intermission are to be alternately repeated. Although the intermission reduces the substantial loading frequency, with the testing machine 2 having the oscillating frequency of 20,000 Hz, the oscillating frequency is still high of 2,000 Hz even if the interval of intermission is assumed to be about 10 times the oscillating time and, accordingly, the number of loadings, which is $10^9$, can be attained in one week.

The stress that governs the fatigue fracture is in essence either the normal stress or the shear stress. Some years have already passed since the ultrasonic axial loading fatigue testing machine (under completely reversed torsion) for evaluating at high speed the fatigue property brought about by the normal stress. In contrast thereto, studies on the ultrasonic torsional fatigue test for the purpose of evaluating at high speed the fatigue property brought about by the shear stress have little been conducted and materials that have hitherto been evaluated are only mild steel and aluminum alloy of a kind liable to the fatigue fracture that takes place at the maximum shear stress amplitude (under completely reversed torsion) of 250 MPa or lower.

In contrast thereto, the fatigue limit maximum contact pressure of the rolling bearing assembly defined in ISO-281: 2007, the standards on the kinetic rated load and the rated life of the rolling bearing assembly, is 1,500 MPa and, considering the linear contact condition, the maximum orthogonal shear stress amplitude $\tau_o$ that acts within the subsurface is 375 MPa. Accordingly, the ultrasonic torsional fatigue testing machine capable of evaluating at the maximum shear stress amplitude equal to or higher than 1,500 MPa is necessitated, but no ultrasonic fatigue torsional testing machine capable of evaluating at such a high maximum shear stress amplitude has not yet been available in the market. For this reason, the present invention has been devised on the basis of the development of the ultrasonic torsional testing machine, the finding that the maximum contact pressure $P_{max}$ at the time the load acts, at which the maximum orthogonal shear stress amplitude $\tau_o$ acting within the subsurface becomes equal to the shear fatigue strength $\tau_{lim}$, can be estimated as the fatigue limit maximum contact pressure $P_{max\ lim}$, and the comprehensive and accurate efforts.

FIG. 2 illustrates a conceptual construction of the estimating system for estimating the shear fatigue property that is used in the practice of the above described estimating method and the fatigue limit maximum contact pressure estimating system for estimating the fatigue limit maximum contact pressure, which includes it, and used in the practice of the fatigue limit maximum contact pressure estimating method referred to hereinbefore. In the instance as shown, reference will be made mainly to the estimating system for estimating the fatigue limit maximum contact pressure and, with respect to the estimating system for estimating the shear fatigue property, only portions thereof which differ from the estimating system for estimating the fatigue limit maximum contact pressure will be described. This estimating system is comprised of a ultrasonic torsional fatigue testing machine 2 and an estimating apparatus 5 for performing the respective processes that are done respectively during the shear fatigue strength determining step S2 and the fatigue limit maximum contact pressure calculating step S3.

Referring to FIG. 2, the ultrasonic torsional fatigue testing machine 2 is made up a testing machine main body 3 an a testing machine control device 4. The testing machine main body 3 is of a structure, in which a torsional vibration converter 7 mounted atop a frame 6 is fitted with a downwardly projecting amplitude amplifying horn 8. A test piece 1 is removably fitted to a tip of the amplitude amplifying horn 8 and an ultrasonic vibration generated by the torsional vibration converter 7 is applied to the test piece 1 after having been amplified as a vibration acting in directions of positive and reversed rotation about a shaft axis of the amplitude amplifying horn 8.

The testing machine control device 4 is made up of a computer 10 and a testing machine control program 11 that is executable by the computer 10. The computer 10 is employed in the form of a personal computer such as, for example, desk top type and includes a central processing unit 12, a storage unit 13 such as, for example, a memory, and input and output interface 14. The testing machine control program 11 referred to above is stored in the storage unit 13, and the remaining storage area of the storage unit 13 is used as a data storage area 13a and a work area. Other than them, a input device 15 such as, for example, a keyboard and/or mouse and an output device 16 such as, for example, a liquid crystal display device for displaying images and/or a printer are provided as respective part of the computer 10 or, alternatively, are connected with the computer 10.

The testing machine control device 4 is a device for controlling the torsional vibration converter 7 of the testing machine main body 3 and a control output is applied from the input and output interface 14 to the vibration converter 7 through an amplifier 17. This testing machine control device 4 performs the following process in accordance with the testing machine control program 11. At the outset, as shown in FIG. 19 showing an example of display on the screen, an image prompting the input of testing conditions (output, which one of an intermittent operation and a continuous operation is to be performed, test terminating conditions, data collecting conditions and so on) is outputted to the display device, which will become the output device 16, and when a testing start command is inputted with the above described testing conditions inputted from the input device 15, the testing machine main body 3 is driven and controlled in accordance with the inputted conditions. It is to be noted that the value of the maximum shear stress amplitude is displayed having been converted from a inputted output P in accordance with the equation (9) as will be discussed later.

Figure 3:
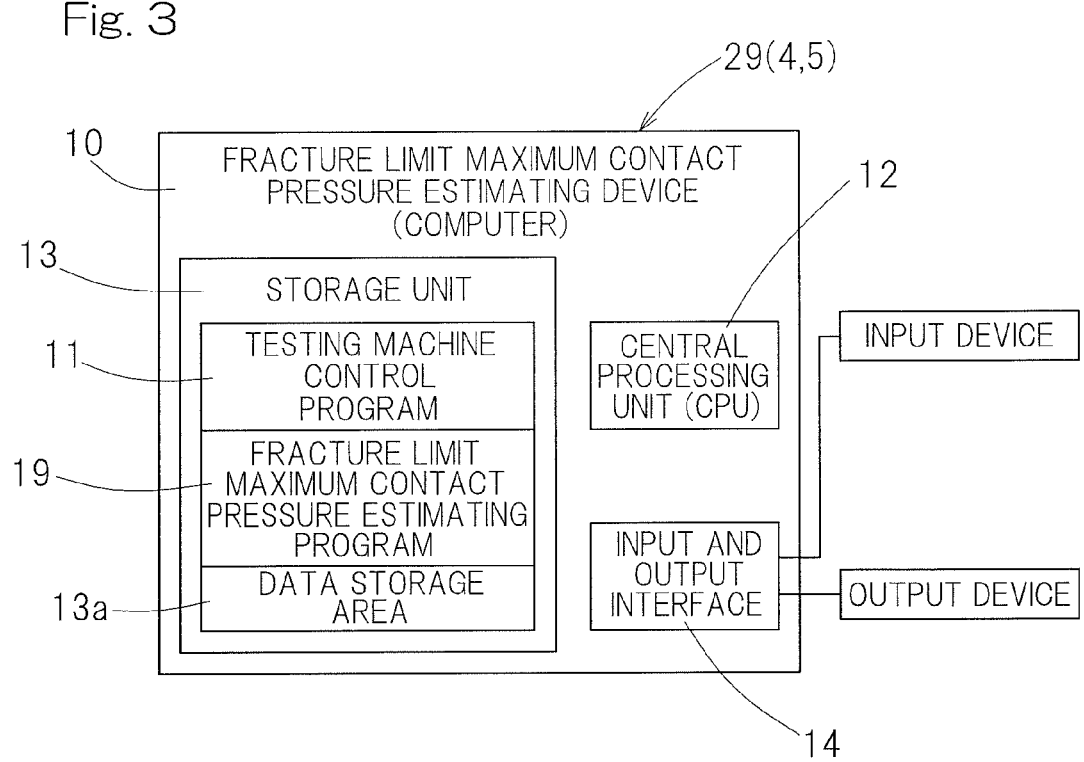
FIG. 3 is a conceptual diagram showing an apparatus which concurrently forms a testing machine control device and a device for estimating the fatigue limit maximum contact pressure in the shear fatigue property estimating system.

Referring to FIG. 2, the estimating device 5 for estimating the fatigue limit maximum contact pressure is made up of the computer 10 and a fatigue limit maximum contact pressure estimating program 19 that is executable by the computer 10. The computer 10 may be either identical with or separate from the computer 4, and includes a central processing unit 12, a storage unit 13 such as, for example, a memory, and an input and output interface 14. Also, the previously described input device 15 and output device 16 are connected with the computer 10 as parts of such computer. FIG. 3 illustrates an example, in which the testing machine control program 11 and the fatigue limit maximum contact pressure estimating program 19 are stored in the same computer 10 to form a combined device 29 for a testing machine control device and a fatigue limit maximum contact pressure estimating device.

Figure 4:
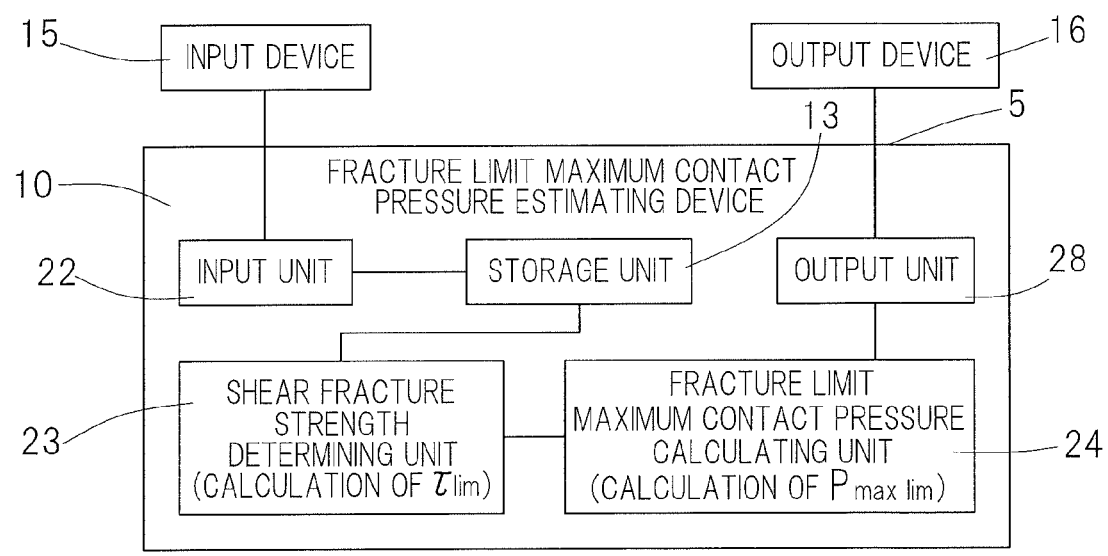
FIG. 4 is a block diagram showing a conceptual structure of the shear fatigue property estimating apparatus.

The fatigue limit maximum contact pressure estimating device 5 makes use of the computer 10 and the fatigue limit maximum contact pressure estimating program 11 to form various sections shown in FIG. 4 showing a conceptual construction thereof. This fatigue limit maximum contact pressure estimating device 5 is operable to estimate the fatigue limit maximum contact pressure $P_{max\,lim}$ of the metallic material that undergoes a rolling contact and includes an input unit 22, a shear fatigue strength determining unit 23 and a fatigue limit maximum contact pressure calculating unit 24, and further the storage unit 13 and the output unit 28 are constructed. In this instance, what the fatigue limit maximum contact pressure calculating unit 24 has been eliminated becomes the shear fatigue property estimating apparatus.

The input unit 22 is operable to store the relation between the shear stress amplitude of the metallic material and the number of loadings, which has been determined by means of the completely reversed ultrasonic torsional fatigue test, in a predetermined storage area of the storage unit 13. More specifically, this input unit 22 is operable to store a file putting together relations between the shear stress amplitude of the metallic material and the number of loadings in a predetermined storage area for later calculation or in such a manner as to enable the site of storage to be specified later by use of a manual input device such as, for example, a keyboard, a readout device for reading out a recording medium, a communication network and so on so.

The shear fatigue strength determining unit 23 is operable to determine the shear fatigue strength $\tau_{lim}$ at the ultra long life regime from the relation between the shear stress amplitude and the number of loading, which has been stored in the storage area, in accordance with a prescribed standard. Specific processing contents performed by the shear fatigue strength determining unit 23 are what have been described in connection with the shear fatigue strength determining step S2 shown in and described with particular reference to FIG. 1A.

The fatigue limit maximum contact pressure calculating unit 24 is operable to determine, according to a predetermined equation, the maximum contact pressure $P_{max}$, at the time the load acts in which the maximum orthogonal shear stress amplitude $\tau_0$ is equal to the shear fatigue strength $\tau_{lim}$, and then rendering this maximum contact pressure $P_{max}$ to be an estimated value of the fatigue limit maximum contact pressure $P_{max\,lim}$. The maximum orthogonal shear stress amplitude $\tau_0$ acts within the subsurface of the object M1 of the metallic material and is determined by the shape and the dimensions of the contact surfaces of the object M1 made of the metallic material and of another object M2 rollingly contacting the object M1 as well as the load to apply a contact pressure. Specific processing contents performed by the fatigue limit maximum contact pressure calculating unit 24 are what has been described in connection with the fatigue limit maximum contact pressure calculating step S3 shown in and described with particular reference to FIG. 1A.

In the next place, the details of the ultrasonic torsional fatigue testing machine 2 and the details of the estimating method of estimating this fatigue limit maximum contact pressure will now be discussed. The ultrasonic torsional fatigue testing machine 2 is designed as a completely reversed ultrasonic torsional fatigue testing machine capable of applying a shear fatigue to the rolling bearing steel at extremely high speed. The range of oscillating frequencies of the torsional vibration converter 7 is within the range of 20,000±500 Hz. It is to be noted that while the vertical vibration converter that can be used in the practice of the ultrasonic axial load fatigue test provides various outputs, the torsional vibration converter currently available in the commercial market is of a type capable of providing only a low output and it has been substantially impossible for one to make such torsional vibration converter by himself or herself. Accordingly, it has been necessitated to optimize the respective shape of the amplitude amplifying horn 8 and the test piece 1 so that the torsional fatigue can be induced in the high strength rolling bearing steel.

The amplitude amplifying horn 8 is of a exponential function type and has a large diameter end face, 38 mm in diameter, which is fixed to the torsional vibration converter 7, and also has a small diameter end face, 13 mm in diameter, to which the test piece 1 is fixed. The amplitude amplifying horn 8, as will be explained in detail later in connection with a second preferred embodiment of the present invention, is so designed and so adjusted to have an amplification factor (the ratio of the torsional angle on the small diameter side relative to the torsional angle on the large diameter side), which is as high as possible, and to resonate at a frequency in proximate to 20,000 Hz. The large diameter end face of the amplitude amplifying horn 8 is provided with a male screw portion protruding in an axial direction for securement of the torsional vibration converter 7 thereto and, also, the small diameter end face thereof is provided with a female screw to which the test piece is fixed. A raw material for this amplitude amplifying horn 8 is a titanium alloy. As a result of actual measurement of the Young's modulus E, the Poisson's ratio $\nu$ and the density $\rho$, the Young's modulus E, the Poisson's ratio $\nu$ and the density $\rho$ were found to be $1.16 \times 10^{11}$ Pa, 0.27, and 4,460 kg/m$^3$, respectively. Using the FEM analyzing software (Marc Mentat 2008 r1) (registered trademark), the eigen value analysis of a free torsional resonance was carried out with the Young's modulus E, Poisson's ratio $\nu$ and density $\rho$ taken as respective physical property values. The result thereof was that the amplification factor was 43.1.

Figure 6:
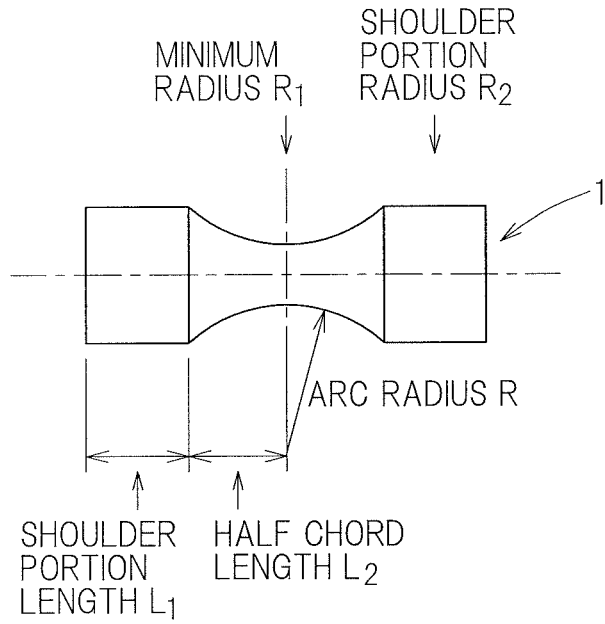
FIG. 6 is a schematic diagram showing a test piece.

The test piece is shown in FIG. 6 in a schematic diagram. In reality, however, the test piece 1 has one end provided with the male screw portion for securing it to a tip of the amplitude amplifying horn 8. As shown in FIG. 6, the test piece 1 is of a dumbbell shape having been made up of cylindrical shoulder portions 1a and 1a at its opposite ends and an axially narrowed intermediate portion 1b continued from and intermediate between the opposite shoulder portions 1a and 1a and having a cross sectional shape fixed by an arcuate curve 1ba. The shape and the dimensions of this test piece 1 are determined by the length $L_1$ of each of the shoulder portions 1a, the half chord length $L_2$, which is half the length of the narrowed intermediate portion 1b, the radius $R_2$ of each of the shoulder portions 1a, the minimum radius $R_1$ of the narrowed intermediate portion 1b and the radius R of the arcuate curve 1ba (all parameters being expressed in unit of millimeter).

In designing the test piece 1, the half chord length $L_2$, the shoulder portion radius $R_2$ and the minimum radius $R_1$ are suitably given and the shoulder portion length $L_1$ is determined when the frequency of oscillation f (=20,000 Hz), the Young's modulus E, the Poisson's ratio $\nu$, and the density $\rho$ ($E=2.04 \times 10^{11}$ Pa, $\nu=0.29$ and $\rho=7,800$ kg/m$^3$ according to the result of actual measurement on a standard heat treated bearing steel SUJ2) into the following equations (1) to (6). On the other hand, the arcuate radius R is determined from the radii $R_1$ and $R_2$ and the half chord length $L_2$.

$$E = \frac{G}{2(1+\nu)} \quad (1)$$

$$\omega = 2\pi f \quad (2)$$

$$\alpha = \frac{1}{L_2} \operatorname{Arccosh}\left(\frac{R_2^2}{R_1^2}\right) \quad (3)$$

$$k = \omega \sqrt{\frac{\rho}{G}} \quad (4)$$

$$\beta = \sqrt{\alpha^2 - k^2} \quad (5)$$

$$L_1 = \frac{1}{k}\operatorname{Arctan}\left[\frac{1}{k}\{\beta\coth(\beta L_2) - \alpha\tanh(\alpha L_2)\}\right] \quad (6)$$

In this instance, when the half chord length $L_2$, the shoulder portion radius $R_2$ and the minimum radius $R_1$ are chosen to be 0.0065 m, 0.0045 m and 0.002 m, respectively, which were previously studied so that the shear stress as large as possible might act on the surface of the smallest diameter portion of the test piece, are inserted in the above equations (1) to (6) together with the previously discussed specific values of the parameters f, E, $\nu$ and $\rho$, the half chord length $L_1$ becomes 0.00753 m. It has, however, been found that no resonance occurred when the test piece was made of the standard quenched and tempered bearing steel SUJ2 with the half chord length $L_1$ set to 0.00753 m. Accordingly, using the FEM analyzing software (Marc Mentat 2008 r1) (registered trademark), the eigen value analysis of the free torsional resonance was carried out with the parameters f, E, $\nu$ and $\rho$ taken as respective physical property values. As a result thereof, the frequency, at which the torsional resonance takes place when $L_1=0.00753$ m, was found to be 19,076 Hz, which departs from the frequency of 20,000±500 Hz, that is, the oscillating frequency of the torsional vibration converter. For this reason, as a result of determination of the eigen value analysis of the torsional resonance that takes place at 20,000 Hz, it has been found that $L_1=0.00677$ m. When the test piece of the standard quenched and hardened bearing steel SUJ2 having the half chord length $L_1$ set to 0.00677 m was prepared, it resonated at 20,000 Hz. The drawing of the test piece is shown in FIG. 7, in which the unit of measurement is millimeter.

Figure 7:
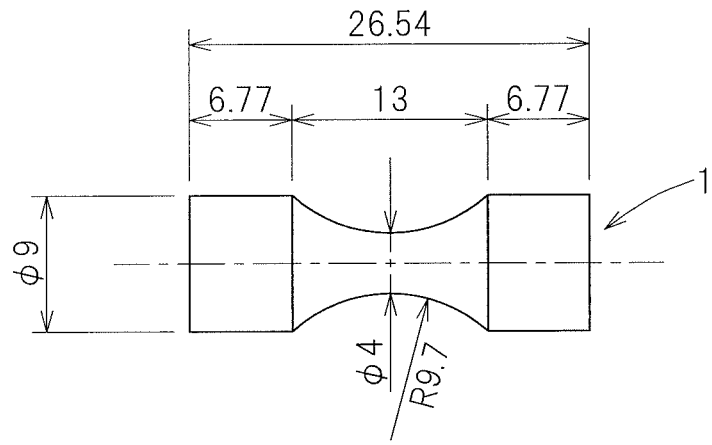
FIG. 7 is a schematic front elevational view showing the test piece.
Figure 8:
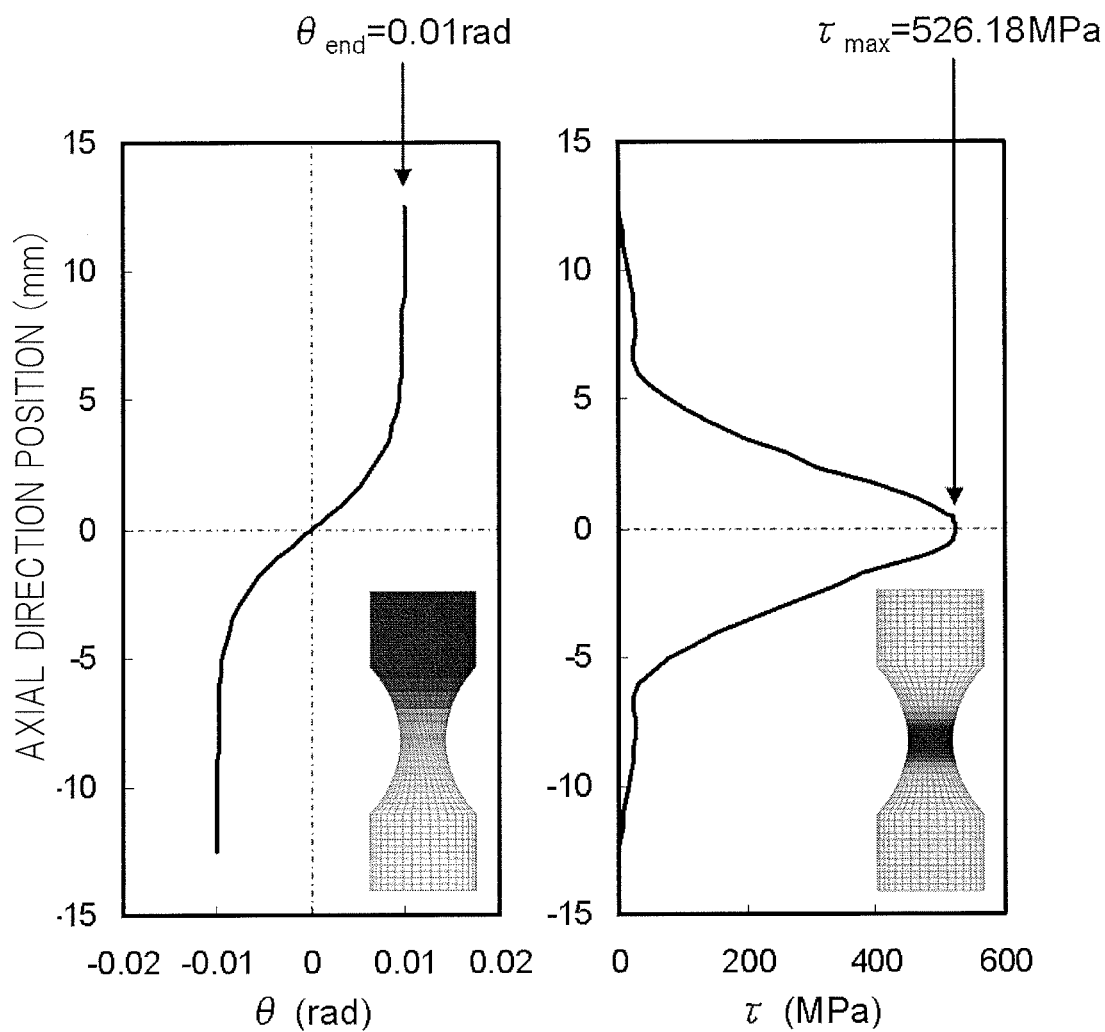
FIG. 8 is a chart showing a pattern of distribution of the torsional angle $\theta$ and the shear stress $\tau$ at a surface (when the torsional angle $\theta_{end}$ at an end face is 0.01 rad) in an axial direction.

FIG. 8 illustrates the torsional angle $\theta$ and the shear stress $\tau$ of the surface, which were obtained as a result of the eigen value analysis of the free torsional resonance with the use of a model of the test piece shown in FIG. 7.

FIG. 8 applies where the end face torsional angle $\theta_{end}$ is 0.01 rad, at which time the maximum shear stress $\tau_{max}$ acting on the surface of the smallest diameter portion of the test piece was found to be 562.18 MPa. In other words, according to the category of the linear elasticity, the relation between the end face torsional angle $\tau_{end}$ and the maximum shear stress $\tau_{max}$ is such as expressed by the equation (7) below. It is, however, to be noted that the unit of the maximum shear stress $\tau_{max}$ is MPa and the unit of the end face torsional angle $\theta_{end}$ is radian.

$$\tau_{max} = 52,618\theta_{end} \quad (7)$$

Using three test pieces 1 of the shape shown in FIG. 7, which were made of the standard quenched and tempered bearing steel SUJ2, the end face torsional angle $\theta_{end}$ was measured with the amplifier output P (%) changed. Alloying components of the raw material for each of the test pieces are shown in the following Table 1. The hardness was 722 HV.

TABLE 1

Alloying Components of Test Piece Raw Material
(expressed by wt %, except for Ti and O expressed by ppm)

| Steel Type | C | Si | Mn | P | S | Ni | Cr | Mo | Cu | Al | Ti | O |
|---|---|---|---|---|---|---|---|---|---|---|---|---|
| SUJ2 | 1.02 | 0.27 | 0.43 | 0.014 | 0.007 | 0.50 | 1.48 | 0.04 | 0.09 | 0.04 | 16 | 6 |

Figure 9:
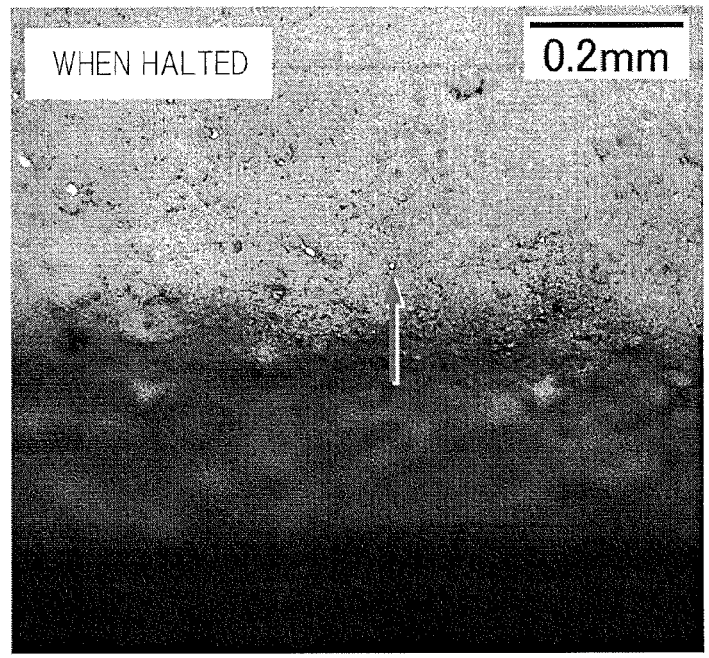
FIG. 9 is a micrograph showing a lower end of a cylindrical surface of a shoulder portion of the test piece in a stationary condition.
Figure 10:
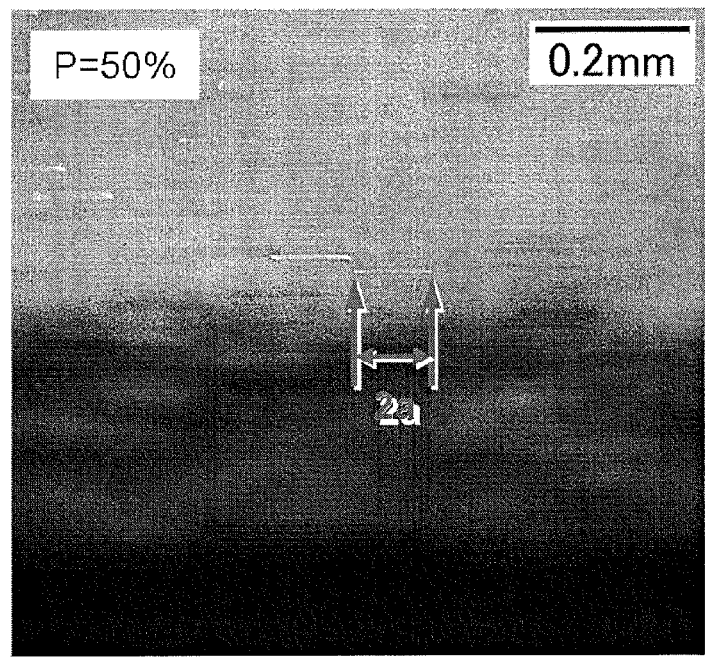
FIG. 10 is a micrograph showing the lower end of the cylindrical surface of the shoulder portion of the test piece in an oscillated condition.

Using a digital microscope (manufactured by and available from Keyence Co., Ltd. Model VHX-900), a micrograph of a shoulder lower end of each of the test pieces was taken at the magnification of 200. Prior to the photographing, a shoulder portion of each of the test pieces was applied an emery grinding (#500, #2000) and a diamond lapping (1 μm) to provide a mirror finish. After each of the test pieces had been fitted to the testing machine, a developing agent for color checking purpose was applied to the shoulder portion of each of the test pieces. FIG. 9 is a micrograph taken at the time of the stationary state and it will readily be seen that the developing agent was not applied at local places. The behavior of each of the local places with no developing agent applied, which had been exhibited when it was oscillated, was been subsequently observed. In the case of the microgram reproduced in FIG. 9, attention was centered on the sites indicated by the arrows. With the amplifier output P changed from 10% to 90% at incremental intervals of 5%, each of the test pieces was oscillated for 1 second and then the microgram of it was taken at the shutter speed of 1/15 second. FIG. 10 is a micrograph obtained during the oscillation with the amplifier output P being 50%, and a width indicated by 2a in FIG. 10 is the site of FIG. 9 on which the attention was centered.

Figure 11:
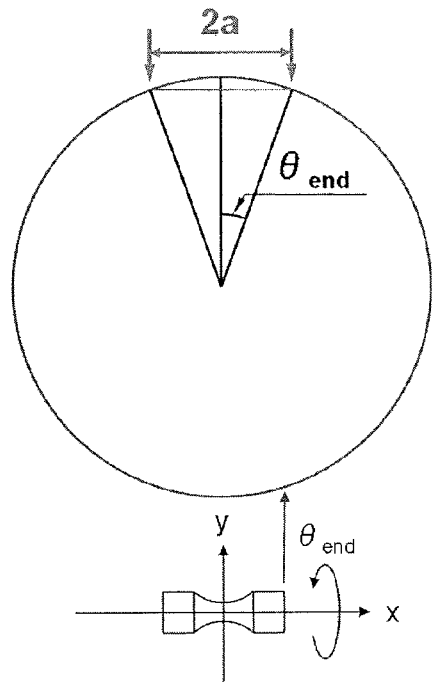
FIG. 11 is an explanatory diagram showing the relation between the range 2a, shown in FIG. 10, and the end face torsional angle $\theta_{end}$.
Figure 12:
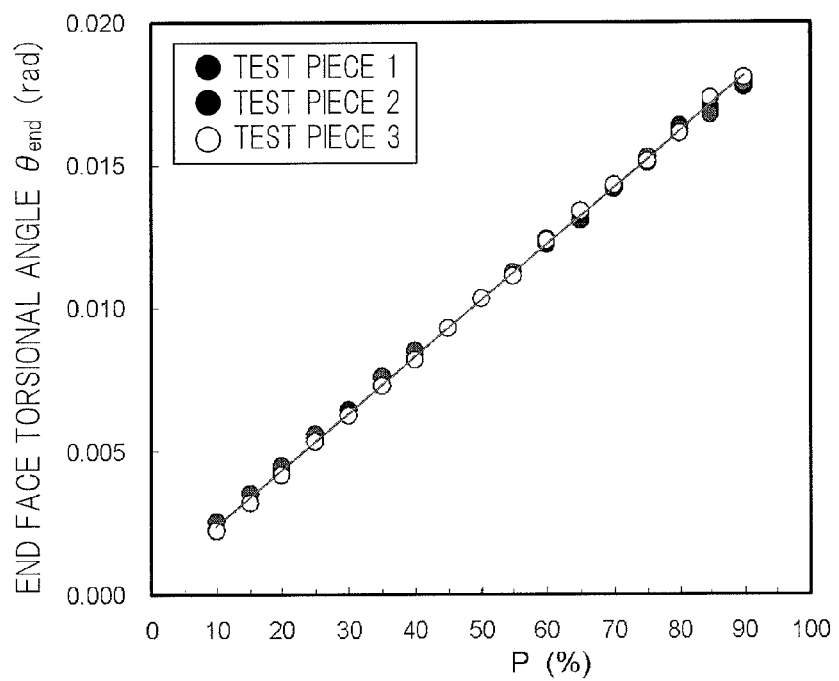
FIG. 12 is a chart showing the relation between an amplifier output P and the end face torsional angle $\theta_{end}$.

From the width 2a, which was measured with the amplifier output P (%) so changed, the end face torsional angle $\theta_{end}$ was determined as shown in FIG. 11. As a result, as shown in FIG. 12, all of the three test pieces 1 have exhibited the substantially same linear relation between the amplifier output P and the end face torsional angle $\theta_{end}$, and the following equation (8) could be obtained as a regression line.

From the equation (8) below, the end face torsional angle $\theta_{end}$ becomes 0.018 rad when the amplifier output P is 90%. From the equations (7) and (8) referred to below and above, respectively, the relation between the amplifier output P and the maximum shear stress amplitude $\tau_{max}$ of the surface in the smallest diameter portion of the test piece comes to be expressed by the following equation (9). From the equation (9) below, the maximum shear stress amplitude $\tau_{max}$ becomes 951 MPa when the amplifier output P is 90%, and it is sufficiently expected that a torsional fatigue can be given to the high strength rolling bearing steel.

$$\theta_{end} = (1.96 \times 10^{-4})P + 4.35 \times 10^{-4} \quad (8)$$

$$\tau_{max} = 52618\{(1.96 \times 10^{-4})P + 4.35 \times 10^{-4}\} \quad (9)$$

Figure 20:
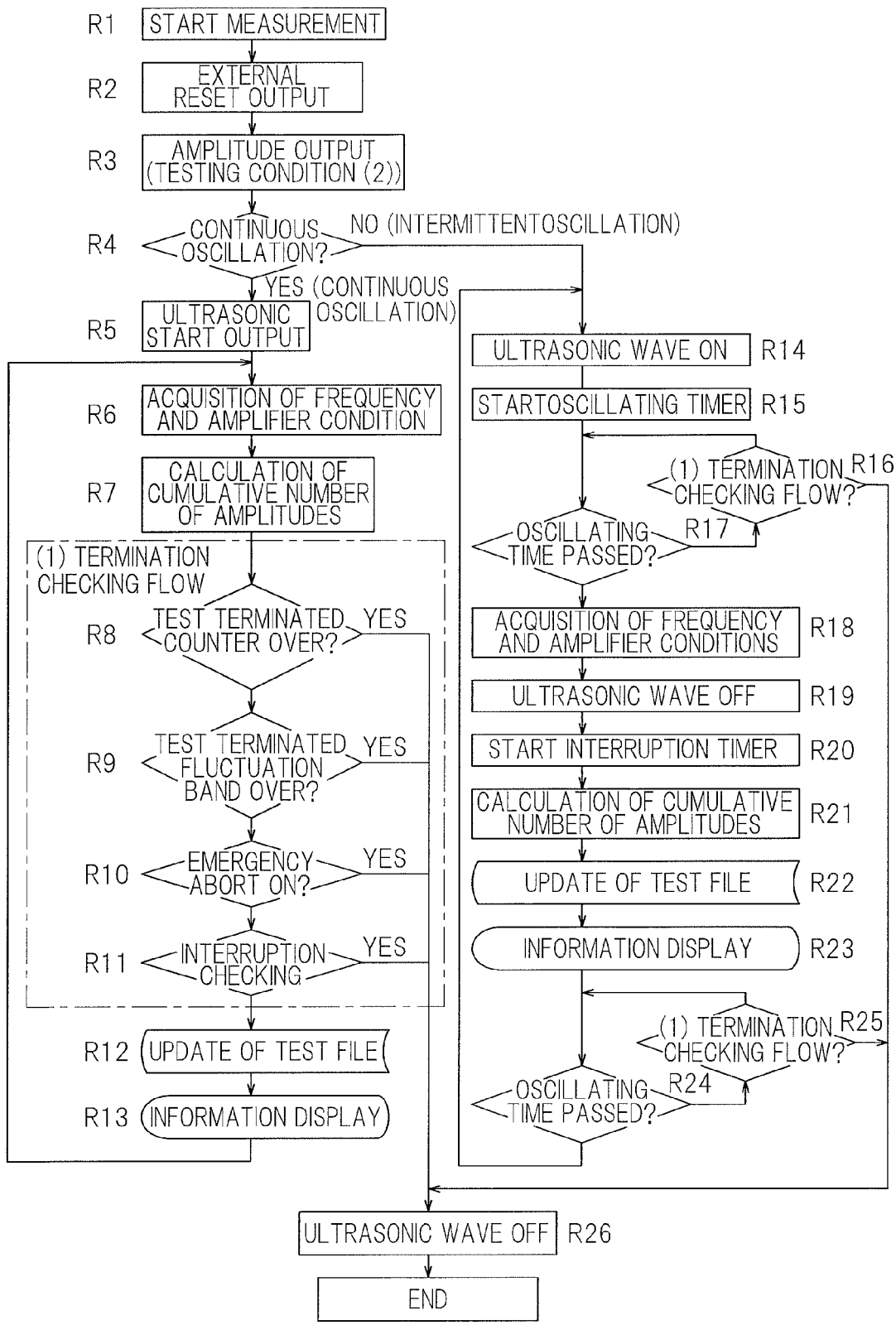
FIG. 20 is a detailed flowchart showing the sequence of testing.

The ultrasonic torsional fatigue testing machine 2 so prepared is so designed as to control the amplifier 17 with the testing machine control device 4 made up of the personal computer 10 and the testing machine control program 11 as hereinbefore described with particular reference to FIG. 2. In FIG. 19, there is shown the screen image through which the testing conditions for the ultrasonic torsional fatigue testing machine 2 can be inputted. FIG. 20 is a detailed flowchart showing the sequence of the testing process and, during the testing process, various control such as, for example, the control of the simplifier output, the control with either the continuous oscillation or the intermittent oscillation selected, information acquisition (acquisition of frequencies and amplifier conditions) and termination of the test are carried out in accordance with the testing conditions so inputted.

Referring to the example of the input screen image shown in FIG. 19, the display of the resonance frequency of 19.97 in the input window indicates that the test piece has resonated at 19.97 kHz when the output is 10%, which is substantially equal to the intended frequency of 20,000 Hz. According to this testing machine control device 4, when an amplifier output is inputted in the measuring condition window, it is converted into the maximum shear stress amplitude from the gradient and the segment of a linear line represented by the equation (9) above. In the same window, one of the continuous run, in which oscillation continues, and the intermitted run, in which oscillation and break are alternately repeated, is selected.

Figure 13:
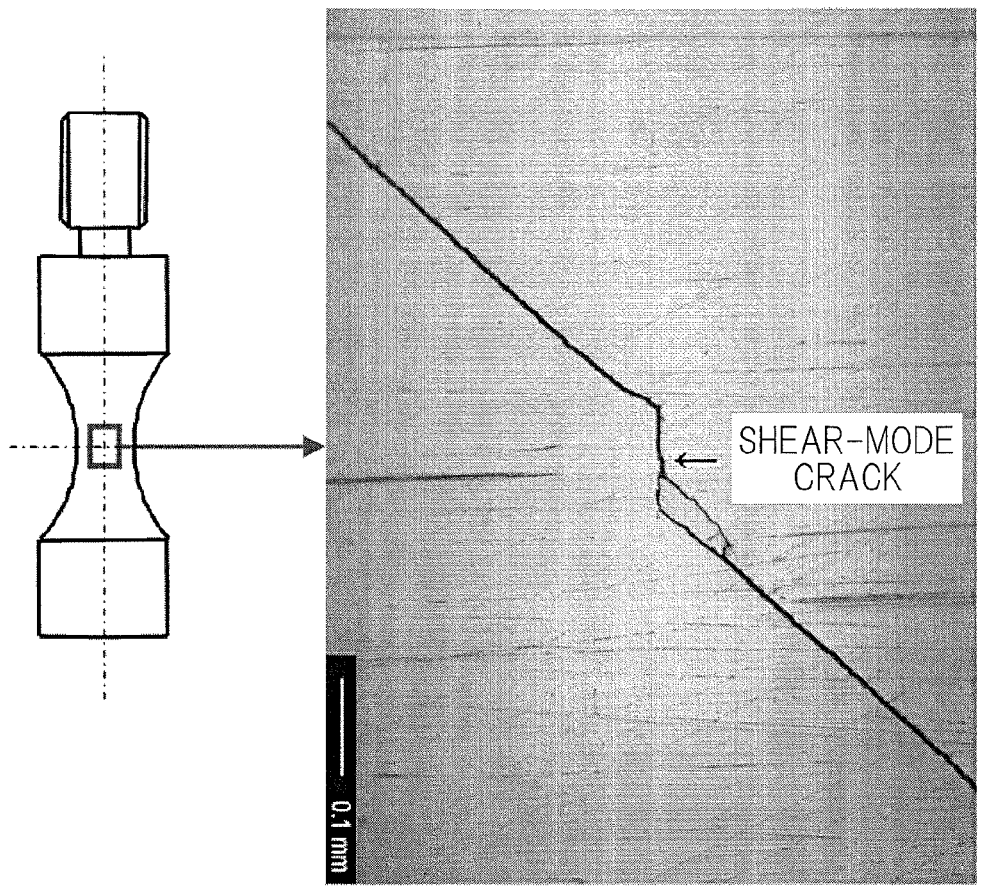
FIG. 13 is an explanatory diagram showing a micrograph of an example of the test piece, which has fractured as a result of the torsional fatigue, and the entire test piece.

When cracking occurs and grows to a certain dimension, the resonance frequency of the test piece 1 is lowered. That a numerical value of 50.00 as the frequency fluctuation band is inputted in the same window is for the purpose that the test has to be halted because of the fatigue fracture when the resonance frequency decreases by a value 50 Hz or higher below that during the test. This value is variable and a proper value should be inputted in dependence on the material used to form the test piece. FIG. 13 illustrates an example of the test piece which has suffered from the torsional fatigue fracture, showing that a shear-mode crack has initiated in an axial direction and, after it had grown to a certain length, it has transited to a tension-mode having been diverted in a slantwise direction.

The bearing steel SUJ2, which was subjected to the standard quenching and tempering at normal temperatures under the atmosphere was evaluated through the intermittent run, in which oscillation and break are alternately repeated. Regardless of the value of the maximum shear stress amplitude, the oscillating time and the break time were thoroughly chosen to be 110 msec and 1100 msec, respectively. The test piece is a member selected out from the same production lot as that used in the previously described end face torsional angle measurement. The test was aborted where no damage occurred until $10^{10}$ times.

Figure 15:
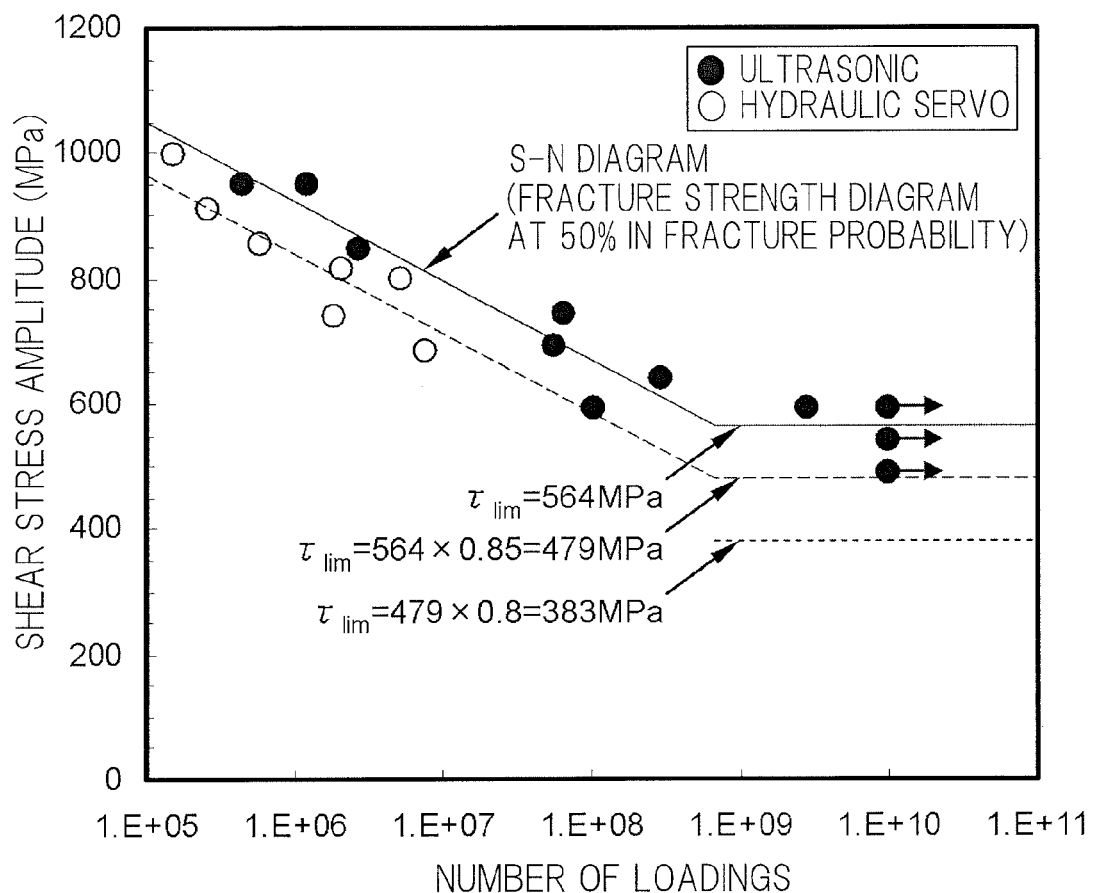
FIG. 15 is a chart showing relation between the amplitude of the shear stress and the number of loading, obtained with the ultrasonic torsional fatigue test, and an S-N diagram (solid line)

The relation between the shear stress amplitude and the number of loadings, which was obtained during the course of the ultrasonic torsional fatigue test, is shown in FIG. 15. The solid line in the chart of FIG. 15 represents the S-N diagram (the diagram representative of the fatigue strength at the fracture probability of 50%) determined by applying to the fatigue limit type line chart of the metallic material fatigue reliability evaluating standards JSMS-SD-6-02 stipulated by the Society of Materials Science, Japan (JSMS), and the shear fatigue strength $\tau_{lim}$ was found to be 564 MPa. Assuming that the shear fatigue strength $\tau_{lim}$ of 564 MPa is, when the line contact state is taken into considered, equal to the maximum orthogonal shear stress amplitude $\tau_o$, calculation is made in accordance with (Fatigue Limit Maximum Contact Pressure $P_{max\ lim}$)=4×(Shear Fatigue Strength $\tau_{lim}$), and as a result, the fatigue limit maximum contact pressure $P_{max\ lim}$ can be assumed to be equal to 2,256 MPa. It is to be noted that the S-N diagram may be determined by applying to the continuously lowering curve model, not the fatigue limit type line model. In such case, however, there is a need to define it as, for example, "the shear fatigue strength $\tau_{lim}$ represents a value on the S-N diagram at the time of $10^{10}$ times."

Figure 14:
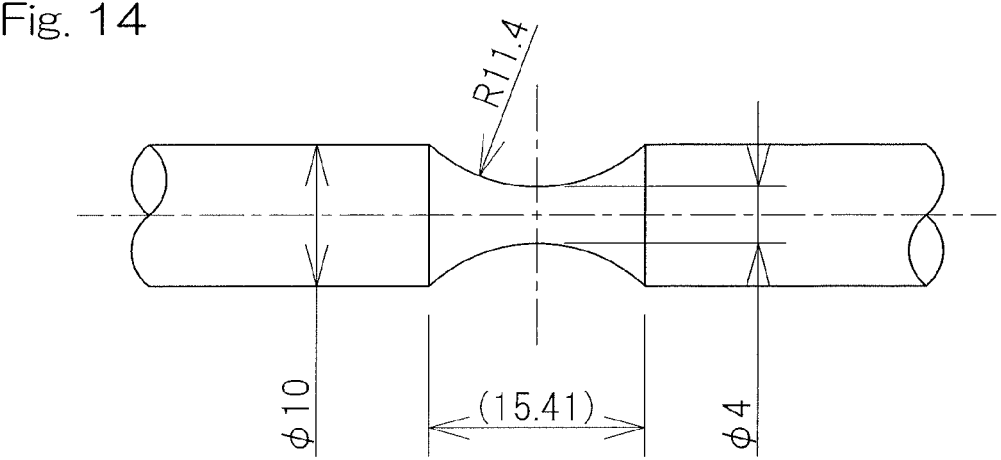
FIG. 14 is a front elevational view showing the test piece used to evaluate with a hydraulic servo torsional fatigue testing machine.

Using the bearing steel SUJ2, shown in Table 1 above, as a raw material, a torsional fatigue test piece (standard quenched and tempered) was prepared, which is provided at a parallel portion of 10 mm in diameter with a narrowed intermediate portion of 4 mm in smallest diameter the same as that in the ultrasonic torsional fatigue test piece, as shown in FIG. 14 (The unit of dimensions in FIG. 14 is expressed in terms of millimeter.). The provision of the narrowed intermediate portion is for the purpose of substantially equalizing the control volume. The torsional fatigue test piece shown in FIG. 14 has R=11.4 mm whereas the ultrasonic torsional fatigue test piece has R=9.7 mm. The reason that R was changed is because of equalizing the stress concentration factor. Prior to the torsional fatigue test, for the purpose of eliminating influences which would be brought about by the presence of surface irregularities, an emery grinding (#500, #2000) and a diamond lapping (1 µm in particle size) were applied to the narrowed intermediate portion.

The torsional fatigue test was carried out with the use of a hydraulic servo torsional fatigue testing machine under completely reversed torsion at a loading frequency of 10 Hz. The result thereof is such as shown by plots of white circle in the chart of FIG. 15 and the fatigue strength at finite life of the hydraulic servo torsional fatigue test result became reduced about 15% from the ultrasonic torsional fatigue test result. The ultrasonic torsional fatigue test tends to assess the shear fatigue strength higher than that in the conventional torsional fatigue test. Accordingly, the value of 479 MPa (shown by the broken line in the chart of FIG. 15), which is 85% of the shear fatigue strength of 564 MPa obtained as a result of the ultrasonic torsional fatigue test, is rendered to be the shear fatigue strength $\tau_{lim}$. In such case, if considering the line contact condition, the shear fatigue strength $\tau_{lim}$ of 479 MPa is equal to the maximum orthogonal shear stress amplitude $\tau_o$, the fatigue limit maximum contact pressure $P_{max\ lim}$ can be assumed to be 1,916 MPa.

In the practice of the torsional fatigue test, the shear stress is maximum at a test piece surface, but zero at the axis. In other words, it is a fatigue test having a stress gradient. In this instance, it is well known that of the tension and compression fatigue tests, the axial load fatigue test involves the uniform normal stress within the section of a smooth portion and, regardless of the diameter of the smooth portion, a certain fatigue limit is exhibited. In contrast thereto, in the rotational bending fatigue test having a stress gradient, it is well known that the fatigue limit decreases as the diameter of the smooth portion increases, and a dimensional effect is exhibited in which it approaches the fatigue limit exhibited in the axial load fatigue test. A report has been made (See the previously mentioned non-patent document 4.) that with respect to three kinds of steels, the axial load fatigue test and the rotational bending fatigue test with the varying diameters of the smooth portion were conducted to find the respective fatigue limits. According to such report, regardless of the kind of the steel, the fatigue limit given by the axial load fatigue test has shown about 80% of the fatigue limit, exhibited by the rotational bending fatigue test using the smooth portion of 4 mm in diameter.

Although according to the tension and compression fatigue test, the fatigue limit exhibited in the axial load fatigue having no stress gradient provides a criterion on a safe side, the torsional fatigue test has no any criterion because the torsional fatigue test has a stress gradient regardless of how large the diameter of the smooth portion is. Now that it has the stress gradient, the dimensional effect can not be discounted in the torsional fatigue test. It is assumed that the criterion of the tension and compression fatigue test is equally applicable even to the torsional fatigue test. In other words, since the minimum diameter of the ultrasonic torsional fatigue test piece is 4 mm, the shear fatigue strength of 383 MPa (shown by the broken line in the chart of FIG. 15), which is 80% of the shear fatigue strength of 479 MPa, which was excessively evaluated and corrected according to the above described ultrasonic torsional fatigue test is rendered to be the shear fatigue strength $\tau_{lim}$. In such case, assuming that considering the line contact condition, the shear fatigue strength $\tau_{lim}$ of 383 MPa is equal to the maximum orthogonal shear stress amplitude $\tau_o$, the fatigue limit maximum contact pressure $P_{max\ lim}$ can be estimated as 1,532 MPa.

The dimensional effect appearing in the fatigue test having the above described stress gradient is brought about by a mechanical factor referred to as the stress gradient and a statistical factor that the volume (control volume) subjected to a large load increases and decreases. In terms of the statistical factor, the P-S-N diagram is to be prepared by conducting a plurality of evaluations at a plurality of stress criterions. However, it may happen that because of the time based limitation, it would be difficult to conduct. In order to determine the shear fatigue strength $\tau_{lim}$ in the chart of FIG. 15, the metallic material fatigue reliability evaluating standard JSMS-SD-6-02 stipulated by the Society of Material Science, Japan, was used. It has a function of acquiring the P-S-N diagram with a small amount of data.

Figure 16:
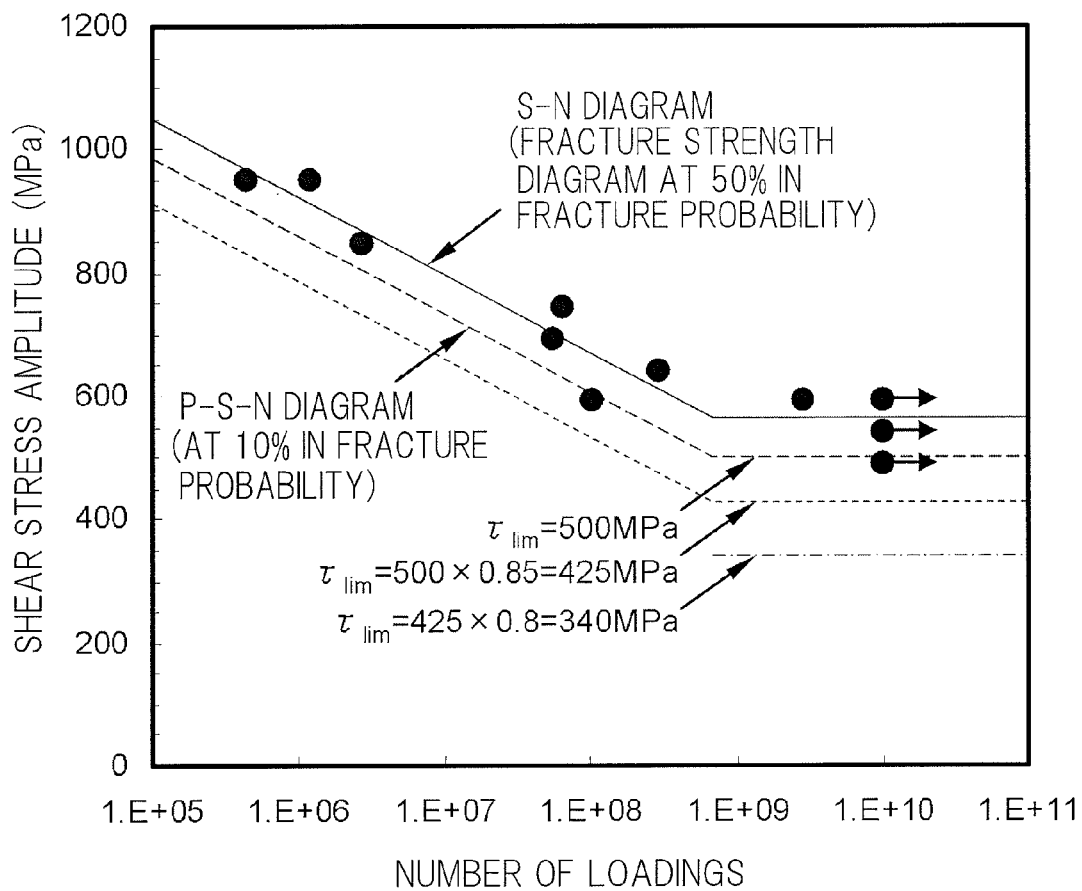
FIG. 16 is a chart showing a P-S-N diagram (broken line) of the 10% probability of fracture, determined from the relation shown in FIG. 15, and the original S-N diagram (solid line)

FIG. 16 shows the P-S-N diagram (shown by the broken line in the chart of FIG. 16) in which the fracture probability obtained thereby is 10%, and the shear fatigue strength of 10% results in 500 MPa. This value, if excessively evaluated and corrected according to the previously described ultrasonic torsional fatigue test, becomes 500×0.85=425 MPa (shown by the dotted line in the chart of FIG. 16). Further, when the above described dimensional effect correction is carried out, the result is that 425×0.80=340 MPa (shown by the single dotted line in the chart of FIG. 16). This value can be said to be the safest shear fatigue strength $\tau_{lim}$. If considering the line contact condition, the shear fatigue strength $\tau_{lim}$ is set to 340 MPa and it is made to be equal to the maximum orthogonal shear stress amplitude $\tau_o$, the fatigue limit maximum contact pressure $P_{max\ lim}$ can be estimated as equal to 1,360 MPa. Although in this instance 10% is chosen as the proper fracture probability, the justifiable fracture probability should be considered by comparing the control volume of the ultrasonic torsional fatigue test piece and the control volume of the actual rolling bearing assembly with each other.

As hereinabove discussed, the method has been shown, in which the relation between the shear stress amplitude of the rolling bearing steel and the number of loadings by means of the ultrasonic torsional fatigue test (under completely reversed torsion), then determining the shear fatigue strength (or the shear fatigue limit) $\tau_{lim}$ within the ultra long life regime therefrom, and estimating from the contact dimension and specification of the rolling bearing assembly as the fatigue limit maximum contact pressure $P_{max\ lim}$ the maximum contact pressure $P_{max}$ when the load acts in which the maximum orthogonal shear stress amplitude $\tau_o$ acting within the subsurface becomes equal to the shear fatigue strength $\tau_{lim}$.

In the meanwhile, FIG. 17 illustrates a distribution of the normal stress $\sigma_z$ in a depthwise direction and the orthogonal shear stress $\tau_{yz}$ in a circumferential section under the contact in the case where under the line contact condition the maximum contact pressure $P_{max}$ of 1,500 MPa acts (in which y represents the circumferential direction and z represents the depthwise direction). The coordinates are made dimensionless with the minor axis radius b of the contact eclipse. The orthogonal shear stress $\tau_{yz}$ exhibits its maximum absolute value at the depth of the dotted line. FIG. 18 illustrates the presence of a minute crack parallel to the contact surface appearing in the vicinity of the depth, at which the eigen value of the orthogonal shear stress is maximized, which were observed when the rolling fatigue test is aborted before the flaking failure occurs and observation is subsequently made of the circumferential section. Drive forces grown parallel to the contact surface appears to be the orthogonal shear stress. In other words, the crack growth mode is the Mode II (inplane shear mode). As shown in FIG. 17, since the normal stress $\sigma_z$ in a direction perpendicular to the cracks is a compression, the mode I(tensile mode) should not be within the realm of possibility and, since the normal stress $\sigma_z$ causes interference among the crack faces, it acts so as to disturb the mode II growth.

On the other hand, with respect to the mode II crack growth (shear mode crack shown in FIG. 13) initiated and grew during the ultrasonic torsional fatigue test, no compressive stress perpendicular to the crack faces acts. Accordingly, the fatigue limit maximum contact pressure $P_{max\ lim}$ estimated from the shear fatigue strength $\tau_{lim}$ within the ultra long life regime that is to be determined by means of the ultrasonic torsional fatigue test may be said to provide a value lower than the actual value, a value on the safe side.

A selecting method for selecting a rolling bearing material used in the practice of the embodiment of the present invention now under discussion is such that a metallic material of a kind, in which the shear fatigue property value assessed by the property assessing method of the rolling bearing material of the previously described construction is higher than a predetermined shear fatigue property value is used as a material for bearing rings and/or rolling elements of the rolling bearing assembly.

According to the property assessing method discussed hereinbefore in connection with the preferred embodiment, from the result of the fatigue test conducted for a brief period of time, the shear fatigue property of the metallic material for the rolling bearing assembly can be accurately estimated. For this reason, the shear fatigue property can be employed as one of test items of the material that is to be used for the bearing rings and/or rolling elements of the rolling bearing assembly. When only the material having the shear fatigue property value, determined by means of the fatigue test conducted actually, which is higher than the predetermined shear fatigue property value, is used as a bearing material, it contributes markedly to the increase of the reliability of the rolling bearing assembly. To use the shear fatigue property as one of the test items for the material to be used, a substantial amount of years are hitherto required to conduct the test and there has been no idea because of overly departure from the actual condition and situation, but according to this method, it can be placed in an actual application and the use thereof can make a contribution to the increase of the reliability of the bearing assembly. It is, however, to be noted that the "predetermined shear fatigue property value", which provides the basis for the determination, may be suitably determined in dependence on the purpose or the like. Also, the estimation of the shear fatigue property value is performed for, for example, each of the production lots, each time the material is purchased, each of sources from which the material has been purchased.

Also, in place thereof, in the practice of the selecting method of selecting the rolling bearing material according to this preferred embodiment, the metallic material of a kind, in which the fatigue limit maximum contact pressure estimated by the fatigue limit maximum contact pressure estimating method of any one of the constructions discussed hereinabove is higher than the predetermined fatigue limit maximum contact pressure can be used as a material for the bearing rings and/or rolling elements of the rolling bearing assembly.

Even in this case, it similarly contributes to the increase of the reliability of the rolling bearing assembly. Although to use the fatigue limit maximum contact pressure as one of the test items for the material to be used, a substantial amount of years are hitherto required to conduct the test and there has been no idea because of overly departure from the actual condition and situation, this selecting method of selecting the rolling bearing material makes it possible to place it in an actual application and the use thereof can make a contribution to the increase of the reliability of the bearing assembly. It is, however, to be noted that the "predetermined fatigue limit maximum contact pressure", which provides the basis for the determination, may be suitably determined in dependence on the purpose or the like, and the estimation of the fatigue limit maximum contact pressure is performed for, for example, each of the production lots, each time the material is purchased, each of sources from which the material has been purchased.

EXAMPLES

Example 1

The fatigue limit maximum contact pressure $P_{max\ lim}$ of a metallic material used to form bearing rings and/or rolling elements of a rolling bearing assembly that is used under a condition, in which only stresses within the elastic limit act is estimated.

The wording "under a condition in which only stresses within the elastic limit act" is intended to speak of the condition, in which when a load is imposed on the metallic material and, after the load has been diminished, the stress and the strain both acting on the metallic material return to "zero (0)".

As the metallic material, which can be used for the bearing rings and/or rolling elements of the rolling bearing assembly of a kind that is used under the condition in which only stresses within the elastic limit act, various bearing steels can be contemplated. As a representative bearing steel, SUJ2, SCr420 and other, which are defined in JIS, i.e., the Japanese Industrial Standards, can be enumerated. It is to be noted that SUJ2 corresponds to SAE52100 according to the American Iron and Steel Institute Standards. In this Example 1, the shear fatigue property of the test pieces made of (1) a "through hardened SUJ2 material" obtained by applying a heat treatment of quenching and tempering to a SUJ2 raw material, (2) a "carbonitrided SUJ2 material" obtained by applying a heat treatment of carbonitriding and tempering to a SUJ2 raw material, and (3) a "carburized SCr420 material" obtained by applying a heat treatment of carburizing and tempering to a SCr420 raw material, respectively, were determined by means of the ultrasonic torsional fatigue test (under completely reversed torsion), and the fatigue limit maximum contact pressure was then estimated from the respective shear fatigue property so determined. For each of the test pieces, such a test piece as shown in FIG. 7 was employed.

Alloying components of the SUJ2 raw material used in the test pieces are shown in the following Table 2.

TABLE 2

Alloying Components of SUJ2 Raw Material used as Test Piece
(expressed by wt %, except for Ti and O expressed by ppm)

| Steel Type | C | Si | Mn | P | S | Ni | Cr | Mo | Cu | Al | Ti | O |
|---|---|---|---|---|---|---|---|---|---|---|---|---|
| SUJ2 | 1.02 | 0.27 | 0.43 | 0.014 | 0.007 | 0.50 | 1.48 | 0.04 | 0.09 | 0.04 | 16 | 6 |

The SUJ2 raw material of the composition shown in Table 2 was subjected to a sequential process of Turning→Heat treatment→Grinding and Finishing to form each of the test pieces (1) and (2) above.

The heat treatment of the test piece (1) of the "through hardened SUJ2 material" was a quench hardening treatment subjected to the SUJ2 raw material in its entirety, in which the SUJ2 raw material in its entirety is quenched, and tempering (Heating: 830° C.×80 min., RX gas atmosphere→Oil quenching→Tempering: 180° C.×180 min.)

With respect to the test piece (2) of the "carbonitrided SUJ2 material", the SUJ2 raw material was carbonitrided and tempered (Heating: 850° C.×150 min. RX gas atmosphere, 6.5 L/min. of $NH_3$ gas added→Oil quenching→Tempering: 180° C.×120 min.)

The RX gas atmosphere referred to above is an atmosphere filled with a gaseous composition containing CO, $H_2$ and $N_2$ as principal component, which was prepared by mixing air into a gas of a carbon hydride system such as, for example, butane or methane and heating at an elevated temperature after a catalyst has been filled.

Alloying components of the SCr420 raw material used in each of the test pieces are shown in the following Table 3.

TABLE 3

Alloying Components of SCr420 Raw Material used as Test Piece
(expressed by wt %, except for O and N expressed by ppm)

| Steel Type | C | Si | Mn | P | S | Ni | Cr | Cu | O | N |
|---|---|---|---|---|---|---|---|---|---|---|
| SCr420 | 0.21 | 0.30 | 0.82 | 0.017 | 0.013 | 0.08 | 1.19 | 0.11 | 7 | 140 |

The SCr420 raw material of the composition shown in Table 3 above was subjected to a sequential process of Turning→Heat treatment→Grinding and Finishing to provide the test piece (3) above.

With respect to the test piece (3) of the carburized "SCr420 material", the SCr420 raw material was subjected to a sequential process of carburizing and quenching and tempering (Carbonizing: 920° C.×4 hr., RX gas atmosphere, Carbon potential maintained at 1.2→Diffusion: 920° C.×3 hr., RX gas atmosphere→Oil quenching→Tempering: 180° C.×120 min.).

Figure 24:
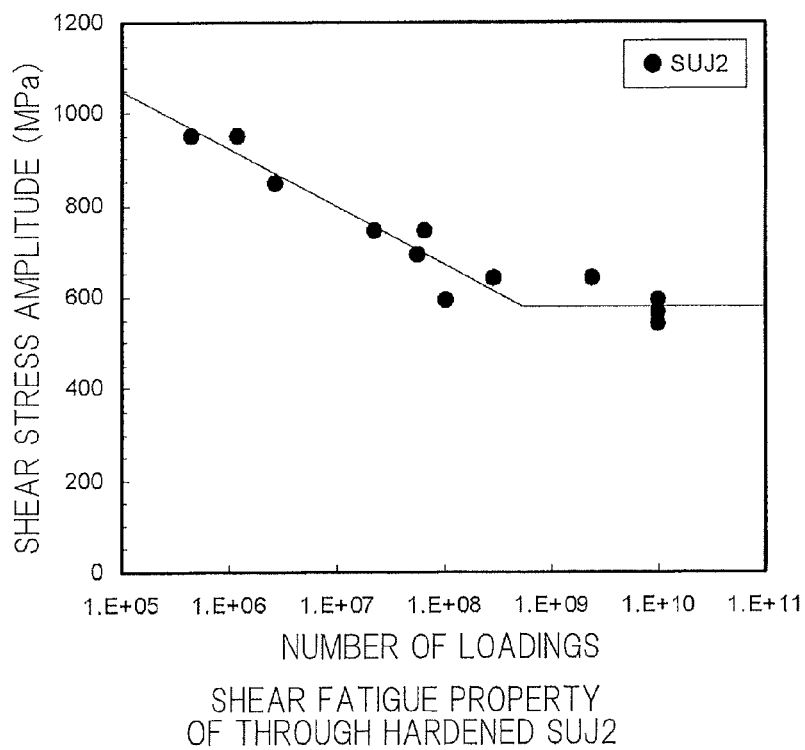
FIG. 24 is a chart showing the shear fatigue property of a test piece of through hardened SUJ2.

FIG. 24 illustrates a chart of the shear fatigue property of the test piece made of the "through hardened SUJ2 material". The solid line in the chart of FIG. 24 is a S-N diagram determined by applying to the fatigue limit type line model of the metallic material fatigue reliability evaluating standards JSMS-SD-6-02 stipulated by the Society of Materials Science, Japan (JSMS), and the shear fatigue strength $\tau_{w0}$ was found to be 577 MPa. To this shear fatigue strength $\tau_{w0}$, the fracture probability correction (Fracture probability: 10%), the dimensional effect correction and the excessive evaluation correction were applied to thereby determine the fatigue limit maximum contact pressure $P_{max\,lim}$ under the line contact condition. Results of estimation of this fatigue limit maximum contact pressure $P_{max\,lim}$ are shown in Table 4 below.

TABLE 4

Estimated Result of Fatigue Limit Maximum
Contact Pressure of Through Hardened SUJ2

| | Shear Fatigue Strength (MPa) | Fatigue Limit Maximum Contact Pressure 1) $P_{max\,lim}$ (MPa) | |
|---|---|---|---|
| (1) $\tau_{w0}$ | 577 | 2309 | Shear fatigue strength determined from the S-N diagram |
| (2) 10% $\tau_{w0}$ | 511 | 2044 | Fracture probability correction applied to (1) (Fracture probability: 10%) |
| (3) 10% $\tau_{w0}$ × 0.8 | 409 | 1636 | Dimensional effect correction applied to (2) |
| (4) 10% $\tau_{w0}$ × 0.8 × 0.85 | 348 | 1391 | Excessive evaluation correction applied to (3) |

1) Line contact condition: $P_{max\,lim}$ = 4 × (Shear fatigue strength)

Figure 25:
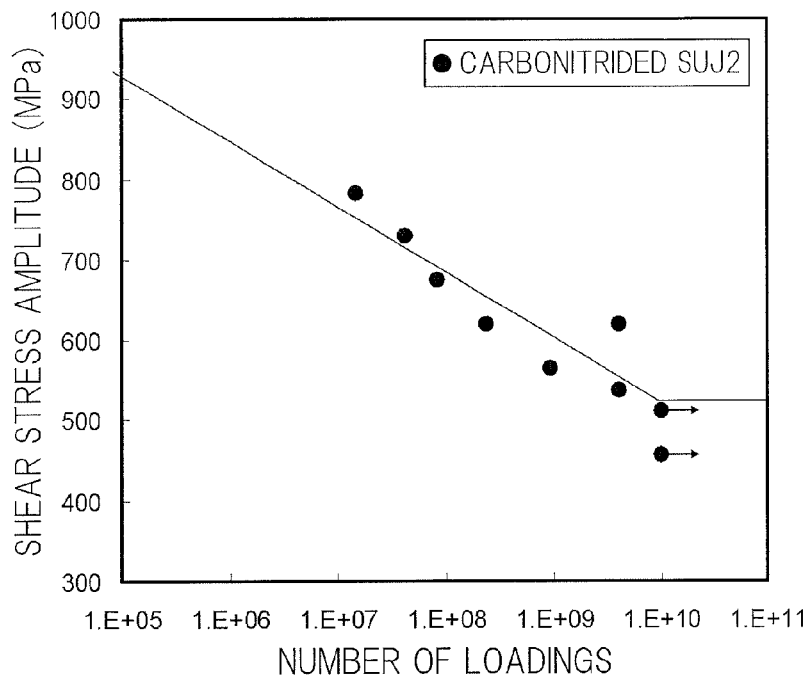
FIG. 25 is a chart showing the shear fatigue property of a test piece of carbonitrided SUJ2.

FIG. 25 illustrates a chart showing the shear fatigue property of the test piece made of the "carbonitrided SUJ2 material". The solid line in the chart of FIG. 24 is an S-N diagram similarly determined in the case of FIG. 24, and the shear fatigue strength $\tau_{w0}$ was found to be 524 MPa. To this shear fatigue strength $\tau_{w0}$, the fracture probability correction (Fracture probability: 10%), the dimensional effect correction and the excessive evaluation correction were applied to thereby determine the fatigue limit maximum contact pressure $P_{max\,lim}$ under the line contact condition. Results of estimation of this fatigue limit maximum contact pressure $P_{max\,lim}$ are shown in Table 5 below.

TABLE 5

Estimated Result of Fatigue Limit Maximum
Contact Pressure of Carbonitrided SUJ2

| | Shear Fatigue Strength (MPa) | Fatigue Limit Maximum Contact Pressure 1) $P_{max\,lim}$ (MPa) | |
|---|---|---|---|
| (1) $\tau_{w0}$ | 524 | 2096 | Shear fatigue strength determined from the S-N diagram |

TABLE 5-continued

Estimated Result of Fatigue Limit Maximum
Contact Pressure of Carbonitrided SUJ2

| Shear Fatigue Strength (MPa) | | Fatigue Limit Maximum Contact Pressure 1) $P_{max\ lim}$ (MPa) | |
|---|---|---|---|
| (2) | 10% $\tau_{w0}$ | 463 | 1853 | Fracture probability correction applied to (1) (Fracture probability: 10%) |
| (3) | 10% $\tau_{w0}$ × 0.8 | 371 | 1482 | Dimensional effect correction applied to (2) |
| (4) | 10% $\tau_{w0}$ × 0.8 × 0.85 | 315 | 1260 | Excessive evaluation correction applied to (3) |

1) Line contact condition: $P_{max\ lim}$ = 4 × (Shear fatigue strength)

Figure 26:
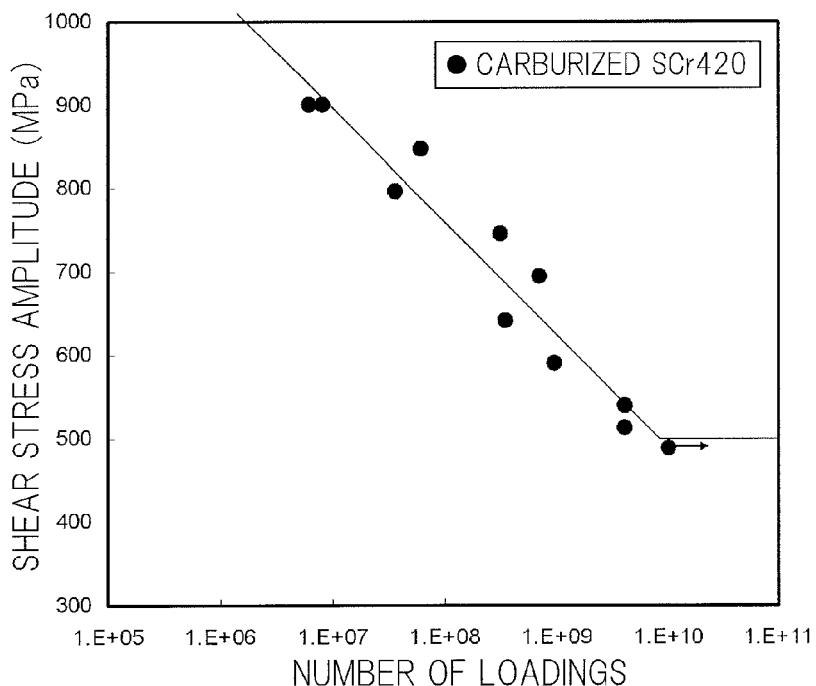
FIG. 26 is a chart showing the shear fatigue property of a test piece of carburized SCr420.

FIG. 26 illustrates a chart showing the shear fatigue property of the test piece made of the "carburized SCr420 material". The solid line in the chart of FIG. 26 is an S-N diagram similarly determined in the case of FIG. 24, and the shear fatigue strength $\tau_{w0}$ was found to be 500 MPa. To this shear fatigue strength $\tau_{w0}$, the fracture probability correction (Fracture probability: 10%), the dimensional effect correction and the excessive evaluation correction were applied to thereby determine the fatigue limit maximum contact pressure $P_{max\ lim}$ under the line contact condition. Results of estimation of this fatigue limit maximum contact pressure $P_{max\ lim}$ are shown in Table 6 below.

TABLE 6

Estimated Result of Fatigue Limit Maximum
Contact Pressure of Carburized SCr420

| Shear Fatigue Strength (MPa) | | Fatigue Limit Maximum Contact Pressure 1) $P_{max\ lim}$ (MPa) | |
|---|---|---|---|
| (1) | $\tau_{w0}$ | 500 | 2000 | Shear fatigue strength determined from the S-N diagram |
| (2) | 10% $\tau_{w0}$ | 443 | 1771 | Fracture probability correction applied to (1) (Fracture probability: 10%) |
| (3) | 10% $\tau_{w0}$ × 0.8 | 354 | 1417 | Dimensional effect correction applied to (2) |
| (4) | 10% $\tau_{w0}$ × 0.8 × 0.85 | 301 | 1205 | Excessive evaluation correction applied to (3) |

1) Line contact condition: $P_{max\ lim}$ = 4 × (Shear fatigue strength)

In the case of the rolling bearing assembly that is used under a condition, in which a light loaded load, in which only a macroscopic elastic stress acts, that is, under a condition in which only the stress within the elastic limit acts, the use of such rolling bearing assembly under such condition appears to have its bearing life that is semi-permanent. For this reason, the determination of the maximum contact pressure, at which no subsurface-originating flaking failure occur, by means of a test is important in selecting the material for the bearing rings and/or the rolling elements or in selecting conditions of use of the bearing assembly.

According to Example 1 discussed above, if in connection with the rolling bearing steel, that is used under the condition in which only the stress within the elastic limit acts, the ultrasonic torsional fatigue test is carried out for the fatigue test, an extremely high speed loading is possible and the relation between the number of loadings and the shear stress amplitude of each of the rolling bearing steels can be determined in a brief period of time (for example, half a day to 1 week). From this relation, the fatigue limit maximum contact pressure $P_{max\ lim}$ can be accurately estimated. For this reason, the fatigue limit maximum contact pressure can be employed as one of the test items about the material that is to be used for the bearing rings and/or rolling elements of the rolling bearing assembly used under the condition in which only the stress within the elastic limit acts. If only the material of a kind, in which the fatigue limit maximum contact pressure actually determined by means of the fatigue test is higher than the predetermined fatigue limit maximum contact pressure, is used as the bearing material, it contributes markedly to the increase of the reliability of the rolling bearing assembly. Although to use the fatigue limit maximum contact pressure as one of the test items about the material to be used, a substantial amount of years are hitherto required to conduct the test and there has been no idea because of overly departure from the actual condition and situation, the above described method makes it possible to place it in an actual application and the use thereof can make a contribution to the increase of the reliability of the bearing assembly.

Example 2

The fatigue limit maximum contact pressure $P_{max\ lim}$, of a metallic material, which will be used as a material for bearing rings and/or rolling elements of a rolling bearing assembly for use in aircrafts, is estimated. This rolling bearing assembly is used as a bearing for supporting a main shaft of a turbine of an aircraft engine. The term "aircraft" referred to above and hereinafter has, however, to be understood as encompassing space vehicles.

As the metallic material referred to above, M50, M50NiL and others, for example, can be enumerated. In the practice of this Example 2, using a test piece, which is made of a M50 raw material and has been heat treated, and a test piece, which is made of a M50NiL raw material and has been heat treated, the shear fatigue property of each of those test piece is determined and from this shear fatigue property so determined, the respective fatigue limit maximum contact pressure is estimated. For each of the test pieces, the test piece shown in and described with reference to FIG. 7 was used.

Alloying components of each of the M50 raw material and the M50NiL raw material used for the respective test pieces are shown in Table 7 below.

TABLE 7

Alloying Components (wt %) of M50 and M50NiL Raw Materials Used for Test Pieces

| Steel Type | C | Si | Mn | P | S | Ni | Cr | Mo | Co | V | W | Cu |
|---|---|---|---|---|---|---|---|---|---|---|---|---|
| M50 | 0.81 | 0.20 | 0.27 | 0.009 | 0.003 | 0.08 | 4.15 | 4.26 | 0.02 | 0.96 | 0.07 | 0.01 |
| M50NiL | 0.14 | 0.18 | 0.27 | 0.004 | 0.001 | 3.42 | 4.20 | 4.37 | 0.01 | 1.21 | 0.02 | 0.02 |

Using the M50 raw material of the composition shown in Table 7 above, the test piece was made through a sequential process of Turning→Heat treatment→Grinding and Finishing. The heat treatment in this case was a through hardening, in which the M50 raw material in its entirety is quenched, a sub-zero treatment, tempering (Heating: 850° C.×80 min+1,090° C.×20 min vacuum→Oil quenching→Sub-zero treatment: −60° C.×90 min→Tempering: 450° C.×60 min.+550° C.×180 min.).

Also, the M50NiL raw material of the composition shown in Table 7 was subjected to a sequential process of Turning→Heat treatment→Grinding and Finishing to form the test piece. The heat treatment in this case was a carburizing and quenching, intermediate annealing, quenching, sub-zero process, and tempering (Carburizing: 960° C.×15 hr., RX gas atmosphere, Carbon potential maintained at 1.2→Diffusion: 960° C.×74 hr., RX gas atmosphere→Intermediate annealing: 650° C.×6 hr→Heating: 850° C.×40 min+1,090° C.×25 min. Vacuum→Oil quenching→Sub-zero process: −80° C.×180 min.→Tempering: 450° C.×60 min.+550° C.×180 min.).

Figure 27:
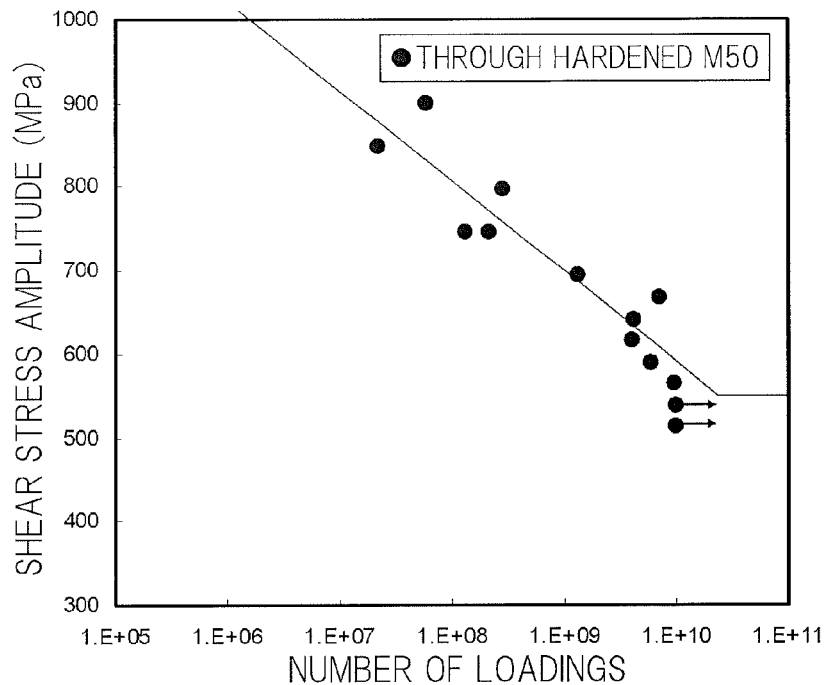
FIG. 27 is a chart showing the shear fatigue property of a test piece of through hardened M50.

FIG. 27 illustrates a chart showing the shear fatigue property of the test piece made of the through hardened M50 material. The solid line in the chart of FIG. 24 is an S-N diagram by applying to the fatigue limit type line model of the metallic material fatigue reliability evaluating standards JSMS-SD-6-02 stipulated by the Society of Materials Science, Japan (JSMS), and the shear fatigue strength $\tau_{w0}$ was found to be 551 MPa. To this shear fatigue strength $\tau_{w0}$, the fracture probability correction (Fracture probability: 10%), the dimensional effect correction and the excessive evaluation correction were applied to thereby determine the fatigue limit maximum contact pressure $P_{max\ lim}$ under the line contact condition. Results of estimation of this fatigue limit maximum contact pressure $P_{max\ lim}$ are shown in Table 8 below.

TABLE 8

Result of Estimation of Fatigue Limit Maximum Contact Pressure of Through Hardened M50

| | Shear Fatigue Strength (MPa) | Fatigue Limit Maximum Contact Pressure 1) $P_{max\ lim}$ (MPa) | |
|---|---|---|---|
| (1) | $\tau_{w0}$ | 551 | 2205 | Shear fatigue strength determined from the S-N diagram |
| (2) | 10% $\tau_{w0}$ | 495 | 1980 | Fracture probability correction applied to (1) (Fracture probability: 10%) |
| (3) | 10% $\tau_{w0}$ × 0.8 | 396 | 1584 | Dimensional effect correction applied to (2) |
| (4) | 10% $\tau_{w0}$ × 0.8 × 0.85 | 337 | 1347 | Excessive evaluation correction applied to (3) |

1) Line contact condition: $P_{max\ lim}$ = 4 × (Shear fatigue strength)

Figure 28:
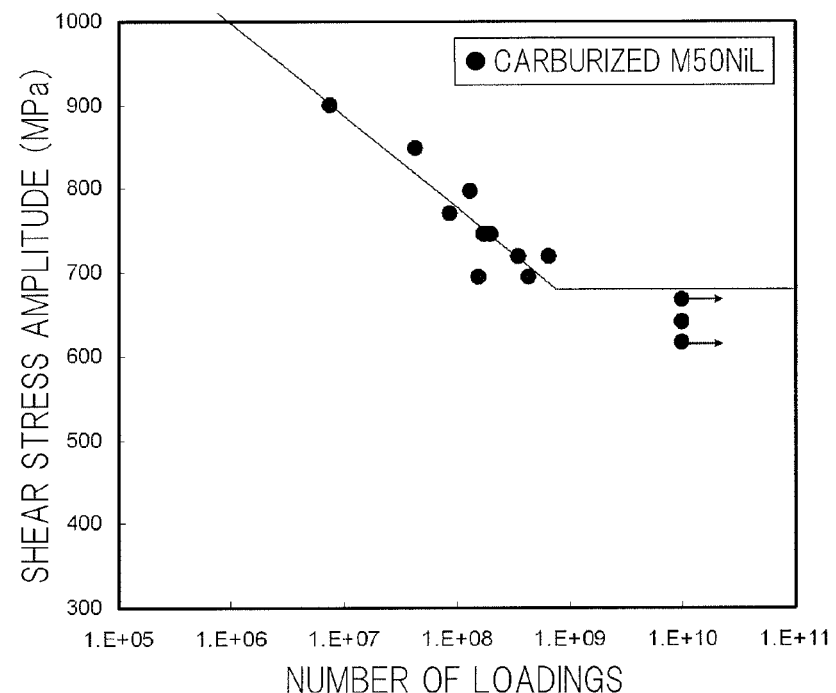
FIG. 28 is a chart showing the shear fatigue property of a test piece of carburized M50NiL.

FIG. 28 illustrates a chart showing the shear fatigue property of the test piece made of the carburized M50NiL material. The solid line in the chart of FIG. 28 is an S-N diagram by applying to the fatigue limit type line model of the metallic material fatigue reliability evaluating standards JSMS-SD-6-02 stipulated by the Society of Materials Science, Japan, and the shear fatigue strength $\tau_{w0}$ was found to be 678 MPa. To this shear fatigue strength $\tau_{w0}$, the fracture probability correction (Fracture probability: 10%), the dimensional effect correction and the excessive evaluation correction were applied to thereby determine the fatigue limit maximum contact pressure $P_{max\ lim}$ under the line contact condition. Results of estimation of this fatigue limit maximum contact pressure $P_{max\ lim}$ are shown in Table 9 below.

TABLE 9

Result of Estimation of Fatigue Limit Maximum Contact Pressure of Carburized M50NiL

| | Shear Fatigue Strength (MPa) | Fatigue Limit Maximum Contact Pressure 1) $P_{max\ lim}$ (MPa) | |
|---|---|---|---|
| (1) | $\tau_{w0}$ | 680 | 2720 | Shear fatigue strength determined from the S-N diagram |
| (2) | 10% $\tau_{w0}$ | 639 | 2555 | Fracture probability correction applied to (1) (Fracture probability: 10%) |
| (3) | 10% $\tau_{w0}$ × 0.8 | 511 | 2044 | Dimensional effect correction applied to (2) |
| (4) | 10% $\tau_{w0}$ × 0.8 × 0.85 | 434 | 1738 | Excessive evaluation correction applied to (3) |

1) Line contact condition: $P_{max\ lim}$ = 4 × (Shear fatigue strength)

Mechanical component parts for use in aircrafts including space vehicles require a higher level of reliability than that required by mechanical component parts for use in general industrial machines and equipments. According to Example 2 discussed hereinabove, when the fatigue test is carried out on metallic materials, which will become the bearing rings and/or rolling elements of the rolling bearing assemblies for use in the aircrafts, by means of the ultrasonic torsional fatigue test, an extremely high speed loading is possible and the relation between the number of loadings and the shear stress amplitude of each of those metallic materials can be determined in a brief period of time (for example, half a day to 1 week). From this relation, the fatigue limit maximum contact pressure $P_{max\ lim}$ can be accurately estimated. For this reason, the fatigue limit maximum contact pressure can be employed as one of the test items about the material that is to be used for the bearing rings and/or rolling elements of the rolling bearing assembly for use in the aircrafts. If only the material of a kind, in which the fatigue limit maximum contact pressure actually determined by means of the fatigue test is higher than the predetermined fatigue limit maximum contact pressure, is used as the bearing material, it contributes markedly to the increase of the reliability of the rolling bearing assembly for use in the aircrafts. Although to use the fatigue limit maximum contact pressure as one of the test items about the material to be used, a substantial amount of years are hitherto required to conduct the test and there has been no idea because of overly departure from the actual condition and situation, the above described method makes it possible to place it in an actual application and the use thereof can make a contribution to the increase of the reliability of the bearing assembly.

Example 3

The fatigue limit maximum contact pressure $P_{max\ lim}$ of the metallic material, which will be used to form bearing rings and/or rolling elements of a rolling bearing assembly for use in railroad vehicles. This rolling bearing assembly for use in the railroad vehicles is a bearing used to support, for example, wheel axles of a railroad vehicle.

As the metallic material referred to above, SNCM420, SUJ2, SUJ3, SCr420 and others can be enumerated. In the practice of this Example 3, using a test piece, which is made of a SNCM420 raw material and has been heat treated, and a test piece, which is made of a SUJ3 raw material and has been heat treated, the shear fatigue property of each of those test piece is determined and from this shear fatigue property so determined, the respective fatigue limit maximum contact pressure is estimated. For each of the test pieces, the test piece shown in and described with reference to FIG. 7 was used.

Alloying components of each of the SNCM420 raw material and the SUJ3 raw material used for the respective test pieces are shown in Table 10 below.

TABLE 10

Alloying Components of SNCM420 and SUJ3 Raw Materials Used for Test Pieces (expressed by wt %, except for O expressed by ppm)

| Steel Type | C | Si | Mn | P | S | Ni | Cr | Cu | Mo | O |
|---|---|---|---|---|---|---|---|---|---|---|
| SNCM420 | 0.21 | 0.26 | 0.61 | 0.017 | 0.013 | 1.63 | 0.5 | 0.11 | 0.20 | 9 |
| SUJ3 | 0.98 | 0.47 | 1.06 | 0.017 | 0.006 | 0.07 | 1.06 | 0.11 | 0.10 | 7 |

Using the SNCM420 raw material of the composition shown in Table 10 above, the test piece was made through a sequential process of Turning→Heat treatment→Grinding and Finishing. The heat treatment in this case was a carburizing and quenching, a secondary quenching, and tempering (Carburizing: 920° C.×4 hr., RX gas atmosphere, Carbon potential maintained at 1.2→Diffusion: 920° C.×3 hr., RX gas atmosphere→Heating: 800° C.×70 min.→Oil quenching→Tempering: 180° C.×120 min.)

Also, the SUJ3 raw material of the composition shown in Table 10 was subjected to a sequential process of Turning→Heat treatment→Grinding and Finishing to form the test piece. The heat treatment in this case was a through hardening, in which the SUJ3 raw material in its entirety was quenched, and tempering (Heating: 810° C.×80 min.→Oil quenching→Tempering: 180° C.×180 min.).

Figure 29:
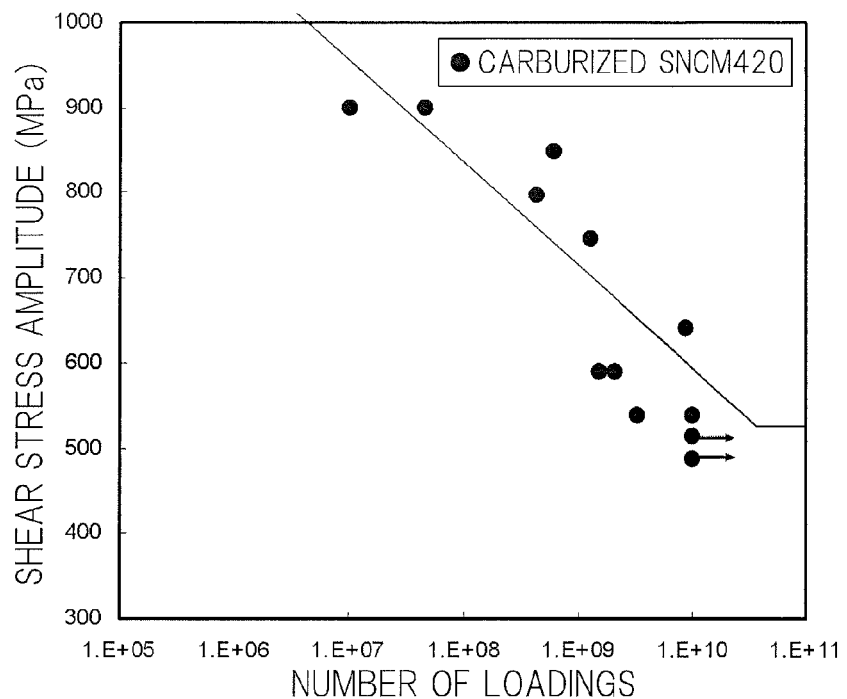
FIG. 29 is a chart showing the shear fatigue property of a test piece of carburized SNCM420.

FIG. 29 illustrates a chart showing the shear fatigue property of the test piece made of the carburized SNCM420 material. The solid line in the chart of FIG. 29 is an S-N diagram by applying to the fatigue limit type line model of the metallic material fatigue reliability evaluating standards JSMS-SD-6-02 stipulated by the Society of Materials Science, Japan (JSMS), and the shear fatigue strength $\tau_{w0}$ was found to be 526 MPa. To this shear fatigue strength $\tau_{w0}$, the fracture probability correction (Fracture probability: 10%), the dimensional effect correction and the excessive evaluation correction were applied to thereby determine the fatigue limit maximum contact pressure $P_{max\ lim}$ under the line contact condition. Results of estimation of this fatigue limit maximum contact pressure $P_{max\ lim}$ are shown in Table 11 below.

TABLE 11

Result of Estimation of Fatigue Limit Maximum Contact Pressure of Carburized SNCM420

| | Shear Fatigue Strength (MPa) | Fatigue Limit Maximum Contact Pressure 1) $P_{max\ lim}$ (MPa) | |
|---|---|---|---|
| (1) $\tau_{w0}$ | 526 | 2103 | Shear fatigue strength determined from the S-N diagram |
| (2) 10% $\tau_{w0}$ | 410 | 1640 | Fracture probability correction applied to (1) (Fracture probability: 10%) |
| (3) 10% $\tau_{w0}$ × 0.8 | 328 | 1312 | Dimensional effect correction applied to (2) |
| (4) 10% $\tau_{w0}$ × 0.8 × 0.85 | 279 | 1115 | Excessive evaluation correction applied to (3) |

1) Line contact condition: $P_{max\ lim}$ = 4 × (Shear fatigue strength)

Figure 30:
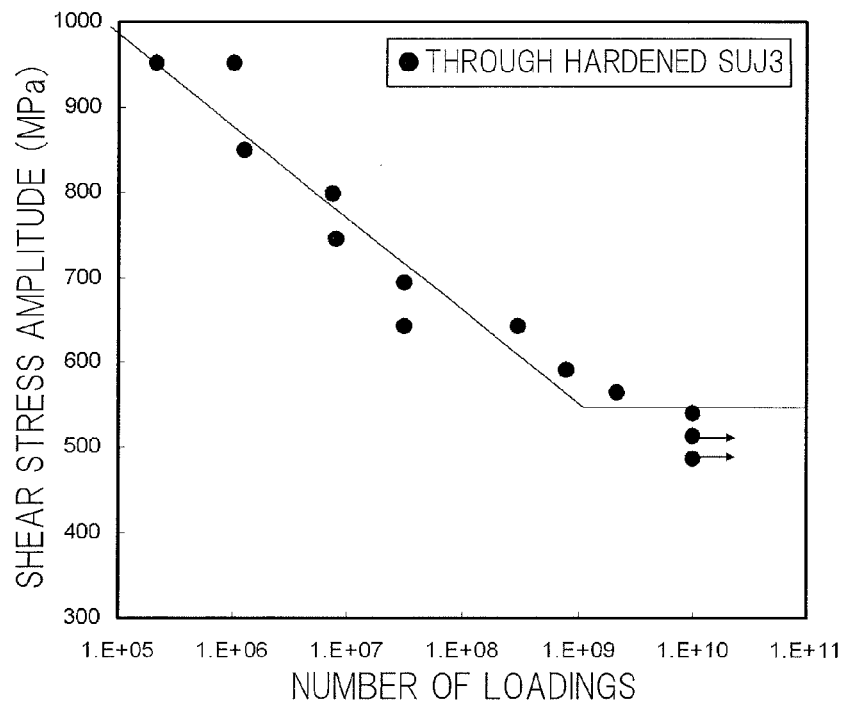
FIG. 30 is a chart showing the shear fatigue property of a test piece of through hardened SUJ3.

FIG. 30 illustrates a chart showing the shear fatigue property of the test piece made of the through hardened SUJ3 material. The solid line in the chart of FIG. 30 is an S-N diagram by applying to the fatigue limit type line model of the metallic material fatigue reliability evaluating standards JSMS-SD-6-02 stipulated by the Society of Materials Science, Japan (JSMS), and the shear fatigue strength $\tau_{w0}$ was found to be 547 MPa. To this shear fatigue strength $\tau_{w0}$, the fracture probability correction (Fracture probability: 10%), the dimensional effect correction and the excessive evaluation correction were applied to thereby determine the fatigue limit maximum contact pressure $P_{max\ lim}$ under the line contact condition. Results of estimation of this fatigue limit maximum contact pressure $P_{max\ lim}$ are shown in Table 12 below.

TABLE 12

Result of Estimation of Fatigue Limit Maximum Contact Pressure of Through Hardened SUJ3

| | Shear Fatigue Strength (MPa) | Fatigue Limit Maximum Contact Pressure 1) $P_{max\ lim}$ (MPa) | |
|---|---|---|---|
| (1) $\tau_{w0}$ | 547 | 2189 | Shear fatigue strength determined from the S-N diagram |
| (2) 10% $\tau_{w0}$ | 488 | 1951 | Fracture probability correction applied to (1) (Fracture probability: 10%) |
| (3) 10% $\tau_{w0}$ × 0.8 | 390 | 1561 | Dimensional effect correction applied to (2) |

TABLE 12-continued

Result of Estimation of Fatigue Limit Maximum
Contact Pressure of Through Hardened SUJ3

| | Shear Fatigue Strength (MPa) | | Fatigue Limit Maximum Contact Pressure 1) $P_{max\ lim}$ (MPa) | |
|---|---|---|---|---|
| (4) | 10% $\tau_{w0}$ × 0.8 × 0.85 | 332 | 1327 | Excessive evaluation correction applied to (3) |

1) Line contact condition: $P_{max\ lim}$ = 4 × (Shear fatigue strength)

The rolling bearing assembly for use in railroad vehicles requires a high level of reliability because it is used with a number of passengers loaded on the railroad vehicle. According to this Example 3 discussed hereinabove, when the fatigue test is carried out even on the metallic materials, which will become the bearing rings and/or rolling elements of the rolling bearing assemblies for use in the railroad vehicles, by means of the ultrasonic torsional fatigue test, an extremely high speed loading is possible and the relation between the number of loadings and the shear stress amplitude of each of those metallic materials can be determined in a brief period of time (for example, half a day to 1 week). From this relation, the fatigue limit maximum contact pressure $P_{max\ lim}$ can be accurately estimated. For this reason, the fatigue limit maximum contact pressure can be employed as one of the test items about the material that is to be used for the bearing rings and/or rolling elements of the rolling bearing assembly for use in the railroad vehicles. If only the material of a kind, in which the fatigue limit maximum contact pressure actually determined by means of the fatigue test is higher than the predetermined fatigue limit maximum contact pressure, is used as the bearing material, it contributes markedly to the increase of the reliability of the rolling bearing assembly for use in the railroad vehicle. Although to use the fatigue limit maximum contact pressure as one of the test items about the material to be used, a substantial amount of years are hitherto required to conduct the test and there has been no idea because of overly departure from the actual condition and situation, the above described method makes it possible to place it in an actual application and the use thereof can make a contribution to the increase of the reliability of the bearing assembly.

Example 4

The fatigue limit maximum contact pressure $P_{max\ lim}$ of the metallic material used to form bearing rings and/or rolling elements of a rolling bearing assembly, which is a wheel support bearing assembly for use in automotive vehicles.

In the wheel support bearing assembly of the first generation type, a bearing steel of a kind, in which a heat treatment of quenching and tempering has been applied, such as, for example, a SUJ2 raw material is generally utilized. On the other hand, in the wheel support bearing assembly of the second generation type, a steel material such as a S53C raw material having been subjected to the induction hardening is employed for an outer ring (hub ring) of the rolling bearing assembly and another steel material such as a SUJ2 raw material having been subjected to quenching and tempering is employed for an inner ring and rolling elements of such rolling bearing assembly. Yet, in the wheel support bearing assembly of the third generation type, a steel material such as a S53C raw material having been subjected to induction hardening is employed for an outboard raceway of an inner ring (hub ring) and an outer ring adapted to be secured to a knuckle whereas a steel material such as SUJ2 raw material subjected to the heat treatment of quenching and tempering is employed for an inboard raceway of the inner ring and rolling elements. In view of this, in the practice of this Example 4, the shear fatigue property of test pieces made of the S53C raw material, to which the heat treatment had been effected, was determined and, then, from this shear fatigue property so determined, the fatigue limit maximum contact pressure was estimated. For those test pieces, the test pieces each shown in and described with particular reference to FIG. 7 were employed.

Alloying components of the S53C raw material used for the test piece are shown in Table 13 below:

TABLE 13

Alloying Components of S53C Raw Material used as Test Piece
(expressed by wt %, except for O expressed by ppm)

| Steel Type | C | Si | Mn | P | S | Cr | Ni | Cu | O |
|---|---|---|---|---|---|---|---|---|---|
| S53C | 0.54 | 0.18 | 0.86 | 0.022 | 0.016 | 0.17 | 0.06 | 0.14 | 8 |

Figure 31A:
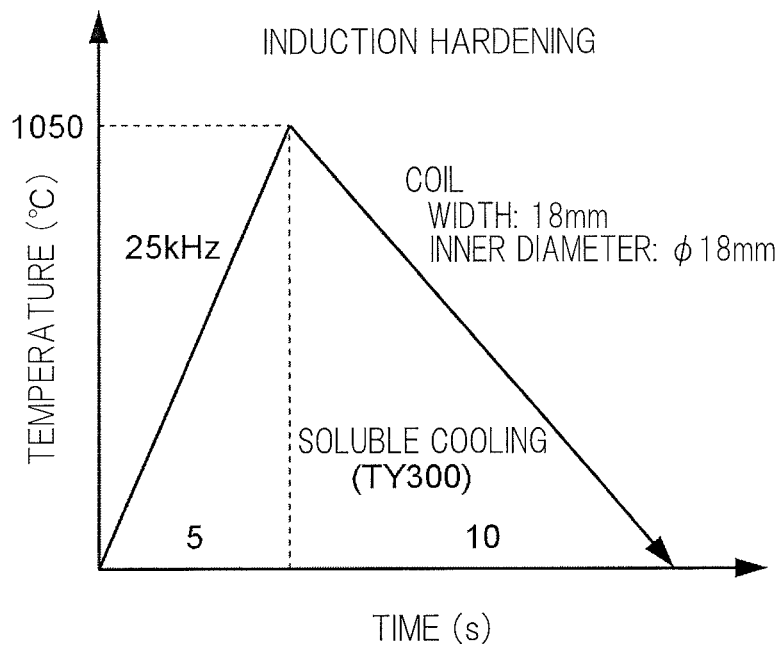
FIG. 31A is a chart showing the heat pattern during the induction hardening of a S53C material.
Figure 31B:
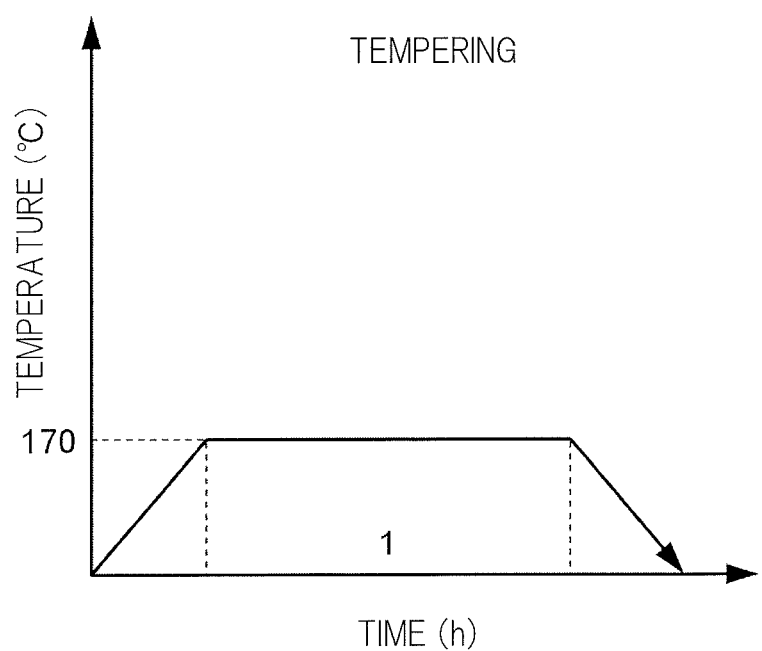
FIG. 31B is a chart showing the heat pattern during the tempering of such material.
Figure 32A:
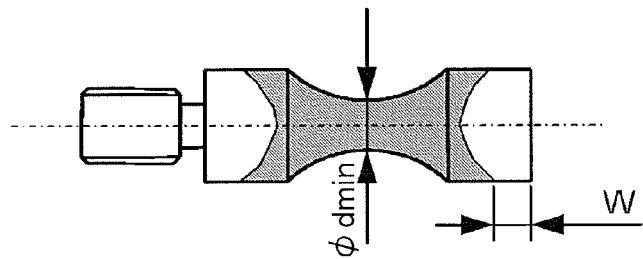
FIG. 32A is a front elevational view of the test piece, schematically illustrating the induction hardening pattern.
Figure 32B:
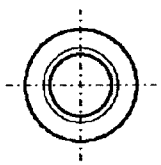
FIG. 32B is a side view of the test piece shown in FIG. 32A.

The S53C raw material of the composition shown in Table 13 above was subjected to a sequential process of Turning→Heat treatment→Grinding and Finishing to provide the test piece. The heat treatment performed in this case is induction hardening and tempering. FIG. 31A illustrates a chart showing the heat pattern of the induction hardening performed on the S53C raw material and FIG. 31B illustrates a chart showing the heat pattern of the tempering performed on the S53C raw material. FIG. 32A illustrates a front elevational view of the test piece, schematically showing the pattern of induction hardening and FIG. 32B illustrates a side view showing the test piece. The hatched area in FIG. 32A represents the schematic pattern of induction hardening. As shown in FIG. 32A, a minimum diameter portion φ dmin (φ dmin is chosen to be 4 mm) is totally hardened. A non-hardened width W (four corners) is chosen to be equal to or smaller than 3 mm Hardening may be effected thoroughly to an end face. The prior austenite γ grain size of the minimum diameter portion φ dmin is chosen to be about #8.

Figure 33:
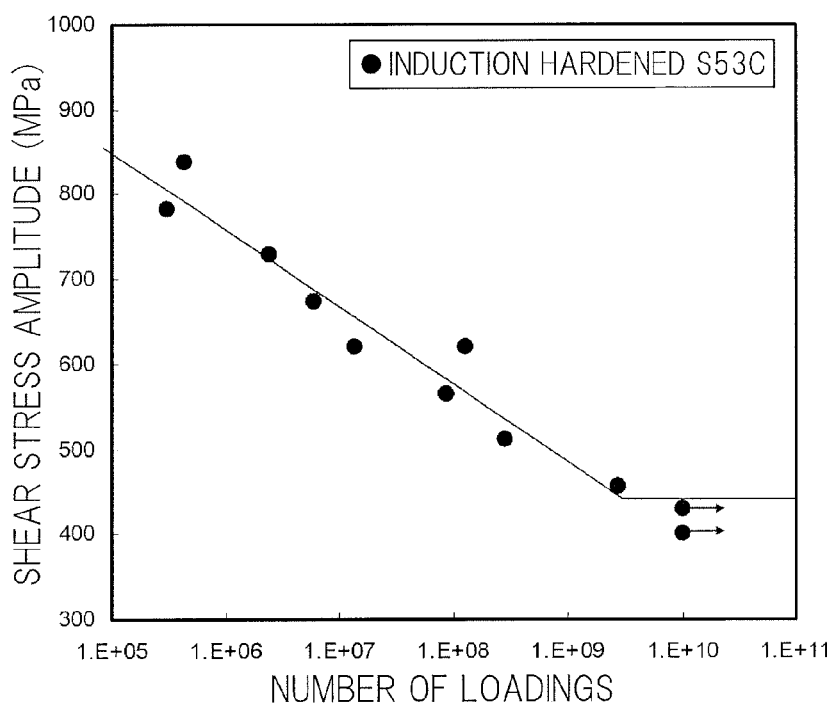
FIG. 33 is a chart showing the shear fatigue property of the test piece of induction hardened S53C.

FIG. 33 illustrates a chart showing the shear fatigue property of the test piece made of the induction hardened S53C material. The solid line in the chart of FIG. 33 is an S-N diagram by applying to the fatigue limit type line model of the metallic material fatigue reliability evaluating standards JSMS-SD-6-02 stipulated by the Society of Materials Science, Japan (JSMS), and the shear fatigue strength $\tau_{w0}$ was found to be 442 MPa. To this shear fatigue strength $\tau_{w0}$, the fracture probability correction (Fracture probability: 10%), the dimensional effect correction and the excessive evaluation correction were applied to thereby determine the fatigue limit maximum contact pressure $P_{max\ lim}$ under the line contact condition. Results of estimation of this fatigue limit maximum contact pressure $P_{max\ lim}$ are shown in Table 14 below.

TABLE 14

Result of Estimation of Fatigue Limit Maximum
Contact Pressure of Induction Hardened S53C

| | Shear Fatigue Strength (MPa) | Fatigue Limit Maximum Contact Pressure 1) $P_{max\ lim}$ (MPa) | |
|---|---|---|---|
| (1) $\tau_{w0}$ | 442 | 1770 | Shear fatigue strength determined from the S-N diagram |
| (2) 10% $\tau_{w0}$ | 396 | 1584 | Fracture probability correction applied to (1) (Fracture probability: 10%) |
| (3) 10% $\tau_{w0}$ × 0.8 | 317 | 1267 | Dimensional effect correction applied to (2) |
| (4) 10% $\tau_{w0}$ × 0.8 × 0.85 | 269 | 1077 | Excessive evaluation correction applied to (3) |

1) Line contact condition: $P_{max\ lim}$ = 4 × (Shear fatigue strength)

The rolling bearing assembly for use in automotive vehicles is required to have a lightweight feature and a compact feature partly because of it being used under severe conditions for a substantial period of time and partly because of the increase of mileage and is therefore required to have the increased reliability. According to Example 4 discussed hereinabove, when the fatigue test is carried out on metallic materials, which will become the bearing rings and/or rolling elements of the rolling bearing assemblies for use in the automotive vehicles, by means of the ultrasonic torsional fatigue test, an extremely high speed loading is possible and the relation between the number of loadings and the shear stress amplitude of each of those metallic materials can be determined in a brief period of time (for example, half a day to 1 week). From this relation, the fatigue limit maximum contact pressure $P_{max\ lim}$ can be accurately estimated. For this reason, the fatigue limit maximum contact pressure can be employed as one of the test items about the material that is to be used for the bearing rings and/or rolling elements of the rolling bearing assembly for use in the automotive vehicle. If only the material of a kind, in which the fatigue limit maximum contact pressure actually determined by means of the fatigue test is higher than the predetermined fatigue limit maximum contact pressure, is used as the bearing material, it contributes markedly to the increase of the reliability of the rolling bearing assembly for use in the automotive vehicle. Although to use the fatigue limit maximum contact pressure as one of the test items about the material to be used, a substantial amount of years are hitherto required to conduct the test and there has been no idea because of overly departure from the actual condition and situation, the above described method makes it possible to place it in an actual application and the use thereof can make a contribution to the increase of the reliability of the bearing assembly.

Figure 34:
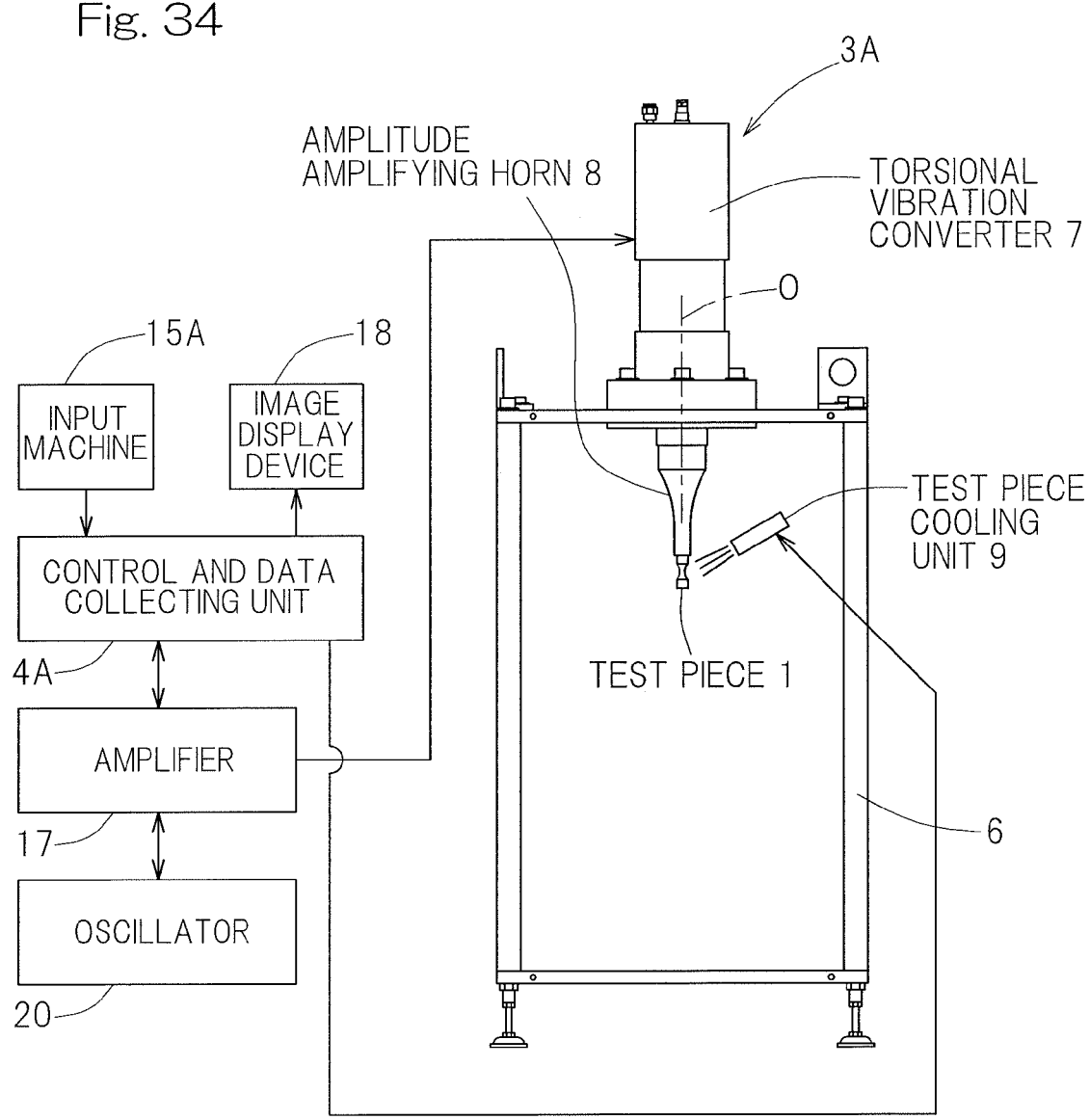
FIG. 34 illustrates a front elevational view of a testing machine main body used in the shear fatigue assessing apparatus capable of executing the shear fatigue property assessing method according to a second preferred embodiment of the present invention, in combination of a block diagram showing the control system thereof.

A second preferred embodiment of the present invention will now be described in detail with particular reference to FIGS. 34 and 35. This second embodiment shows one example of a shear fatigue property estimating apparatus that is used in the practice of the shear fatigue property assessing method of the metallic material that undergoes a rolling contact. Also, in describing this second embodiment, only differences appearing therein from the previously described first embodiment will be described, while component parts thereof similar to those in the previously described first embodiment are shown by like reference numerals and the details thereof are not reiterated for the sake of brevity. The shear fatigue property estimating apparatus according to this second embodiment includes a testing machine main body 3A having a torsional vibration converter 7 and an amplitude amplifying horn 8, an oscillator 20, an amplifier 17, and a control and data collecting unit 4A. The control and data collecting unit 4A corresponds to the testing machine control device 4 shown and employed in connection with the previously described first embodiment.

The testing machine main body 3A referred to above is of a structure, in which the amplitude amplifying horn 8 that projects downwardly is fitted to the torsional vibration converter 7 mounted atop a frame structure 6, the test piece 1 is removably fitted to a tip of the amplitude amplifying horn 8 and ultrasonic vibrations generated by the torsional vibration converter 7 are applied to the test piece 1 after having been amplified as vibrations acting in positive and reversed rotational directions about the axis O of the amplitude amplifying horn 8. This testing machine main body 3A has a test piece air cooling unit 9 for forcedly cooling the test piece 1. The test piece air cooling unit 9 is employed in the form of, for example, a nozzle or the like that is fluid connected with a compressed air generating source (not shown) such as, for example, a blower through a piping for applying an air to the test piece 1, and is capable of being switched between an air blow mode and an air blow halt mode in dependence on whether an electromagnetic valve (not shown) or the compressed air generating source is turned on or whether it is turned off.

The torsional vibration converter 7 referred to above is operable to generate torsional vibrations, which will become positive and reversed rotation about the center axis O of rotation at a frequency equal to that of a two phase alternating power when the latter is applied thereto. The alternating power to be applied to the torsional vibration converter 7 is rendered to be an alternating power having positive and negative polarities that are symmetrical relative to each other, such as, for example, a sine wave or the like and the torsional vibrations generated are rendered to be completely reversed vibrations, in which a positive rotational direction and a reversed rotational direction that are symmetrical relative to each other.

The amplitude amplifying horn 8 referred to above has a tip end portion provided with a mounting portion in the form of a female screw hole formed to a tapering shape, to which the test piece is coaxially fitted, and a base end to which the torsional vibration converter is fixed. This amplitude amplifying horn 8 enlarges the amplitude of the torsional vibration of the vibration converter 7, applied to the base end, to generate such an enlarged amplitude at the tip end portion. A raw material for the amplitude amplifying horn 8 is, for example, a titanium alloy.

The oscillator 20 referred to above is comprised of an electronic appliance operable to generate a voltage signal of a frequency within the ultrasonic wave region, which will become a frequency required to oscillate the amplitude amplifying horn 8. This oscillator 20 has an oscillating frequency that is fixed to a frequency, for example, within the range of ±500 Hz, or has a capability of adjusting the frequency.

The amplifier 17 referred to above is an electronic appliance for amplifying an output of the oscillator 20 and then applying an alternating power of a frequency within the ultrasonic wave region to the torsional vibration converter 7. This amplifier 17 is of a type, in which the magnitude of an output of the alternating power and the ON or OFF state can be controllable in response to an input from the outside. The maximum output of this amplifier 17 is rendered to be 300 W in the embodiment now under discussion.

The control and data collecting unit 4A referred to above is operable to apply an input for control of, for example, the magnitude of the previously described output and/or ON or OFF control to the amplifier 17 and then to collect from the amplifier 17 an oscillating data such as the frequency under test, the state of an output or the like of the amplifier 17 and the number of loadings. This control and data collecting unit 4A is provided with a function of controlling the test piece air cooling unit 9, in addition to the above functions. The control and data collecting unit 4A is comprised of a computer such as, for example, a personal computer or the like and a program (not shown) executable thereby. The control and data collecting unit 4A is connected with an input device 15A such as, for example, a keyboard and/or a mouse, and a screen display device 18 such as, for example, a liquid crystal display device for displaying images on a screen or is provided with them as respective parts of the computer referred to above.

Figure 35:
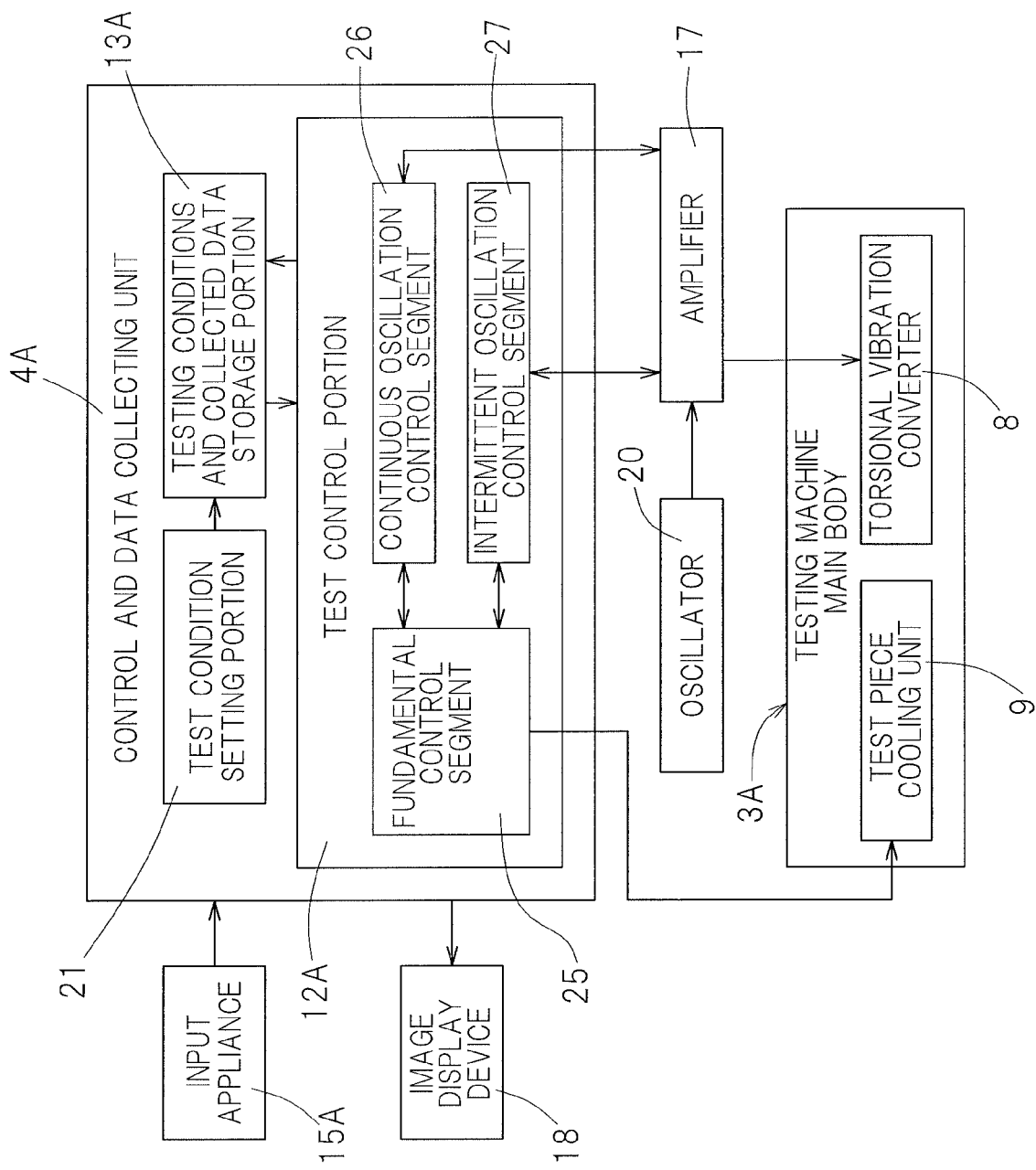
FIG. 35 is a block diagram showing a conceptual construction of the shear fatigue property assessing apparatus.

The control and data collecting unit 4A is constituted by the computer and the program, and includes various portions as shown in FIG. 35. In other words, the control and data collecting unit 4A includes a testing condition setting portion 21, a testing condition and collected data storage portion 13A and a test control portion 12A. The testing condition and collected data storage portion 13A and the test control portion 12A correspond respectively to the storage unit 13 and the central processing device 12, both employed in the practice of the previously described first embodiment. The testing condition setting portion 21 is operable to store a condition for driving the torsional vibration converter 8 and a testing condition including conditions for collecting data, which conditions are input from the input appliance 15A, in the testing condition and collected data storage portion 13A, that is, to set such conditions as a condition for the control. The testing condition setting portion 21 referred to above is, more specifically, operable to cause the input screen image, shown in FIG. 19, to be displayed by the image display device 18 and performing the process shown in the flowchart of FIG. 37.

The test control portion 12A referred to above is operable to drive the torsional vibration converter 8 and then to collect the above described data in accordance with the testing conditions set by the testing condition setting portion 21. This test control portion 12A is made up of a fundamental control segment 25, a continuous oscillation control segment 26 and an intermittent oscillation control segment 27. The test control portion 12A is operable to perform the process shown in the flowchart of FIG. 20. The continuous oscillation control segment 26 is operable to perform sequential process steps R8 to R13 of FIG. 20, the intermittent oscillation control segment 27 is operable to perform sequential process steps R14 to R24 of FIG. 20, and the basic control segment 25 is operable to perform the remaining sequential process steps.

The shear fatigue property assessing method according to this second embodiment will now be described in detail. This assessing method is a method for testing and evaluating the shear fatigue property of the metallic material, which undergoes a rolling contact, with the use of a shear fatigue property estimating apparatus of a structure shown in FIG. 34 and also with the use of a test piece 1 made of such metallic material. This assessing method further performs a test, in which the shape and the dimension of the test piece 1 are rendered to be the shape and the dimension that resonate with the vibration of the amplitude amplifying horn 8 driven by the torsional vibration converter 7, the vibration converter 7 is driven at a frequency within an ultrasonic wave region (for example, within the range of 20,000±500 Hz in the instance as shown), and the test piece 1 is caused to resonate with the vibration of the amplitude amplifying horn 8 to undergo a shear fatigue fracture. The lowermost limit value of the frequency range, at which the torsional vibration converter 7 is driven, may be set to $(20{,}000 - 500 + \alpha)$ Hz. It is, however, to be noted that the parameter $\alpha$ represents a spare value for change in character during the test of the test piece and may be 200 Hz or lower. During this test, various data are collected and, using the obtained relation between the shear stress amplitude and the number of loadings, the shear fatigue property of the metallic material that undergoes a rolling contact is assessed. This metallic material, where it is used as a high strength metallic material for a rolling bearing assembly, is a bearing steel such as, for example, a high carbon chromium bearing steel (JIS-SUJ2).

According to the above described shear fatigue property assessing method, since the extremely high speed ultrasonic torsional fatigue testing machine, in which the oscillation frequency is within the ultrasonic wave region, is carried out, in assessing the shear fatigue property of the metallic material that undergoes the rolling contact, the required number of loadings is attained in a brief time and, hence, the shear fatigue property can be assessed quickly. By way of example, if continuously oscillated at a frequency of 20,000 Hz, the number of loadings attains $10^9$ times only in half a day. Also, since the test is performed, in which the shear fatigue fracture occurs actually, the shear fatigue property can be determined accurately as compared with a conventional method, in which the maximum size of a non-metallic inclusion is used as a quality index of the steel. Since the test piece is caused to resonate, investment of a slight amount of energies is effective to cause the shear fatigue fracture efficiently.

Hereinafter, specific contents of the shear fatigue property assessing method and the estimating apparatus will be described in detail. Since the torsional vibration converter 7, to the extent as examined in the commercial market, is available in only one type that is sold in the market and can control amplification, there is no way other than to use it. Accordingly, the shape of the amplitude amplifying horn 8 as well as the test piece 1 is designed and optimized so that the shear fatigue can be induced in the high strength metallic material.

Designing of the amplitude amplifying horn 8 will be first described. The standard amplitude amplifying horn (of an exponential type) sold together with the commercially available torsional vibration converter 7 is of a size, in which the diameter of the large diameter end face, which is fixed to the torsional vibration converter 7, is 38 mm and the diameter of the reduced diameter end face, to which the test piece 1 is fixed, is 15 mm. This amplitude amplifying horn is so designed and so adjusted to undergo a resonance at a frequency in the vicinity of 20,000 Hz. A center portion of the large diameter end face of the amplitude amplifying horn is provided with a male screw portion, which is a mounting portion to be fixed to the torsional vibration converter, so as to project and the reduced diameter end face is made vacant with a mounting portion in the form of a female screw for connection with the test piece. A raw material for the amplitude amplifying horn 8 is a titanium alloy. As a result of measurement of the Young's modulus E, the Poisson's ratio $\nu$, and the density $\rho$, it has been found that the Young's modulus E, the Poisson's ratio $\nu$, and the density $\rho$ were $1.16 \times 10^{11}$ Pa, 0.27, and 4,460 kg/m$^3$, respectively. Using the FEM analyzing software (Marc Mentat 2008 r1) (registered trademark) and, also, using the above described Young's modulus E, Poisson's ratio $\nu$ and density $\rho$ as respective physical property values, the eigen value analysis of the free torsional resonance was carried out. As a result thereof, the amplification factor (the ratio of the torsional angle on the small diameter side relative to the torsional angle on the large diameter side) was found to be 25.8 times.

The shape of the test piece 1 is the same as that shown in FIG. 6 in connection with the previously described first embodiment and, in this test piece 1, when the parameter L2 chosen to be 0.0070 m, the parameter R2 chosen to be 0.0060 m and the parameter R1 chosen to be 0.0030 m were inserted in the previously described equations (1) to (6) together with the above described specific values of the Young's modulus E, the Poisson's ratio ν, and the density ρ, it has been found that the parameter L1 was 0.01012 m. However, when the test piece 1 is made of the standard quenched and tempered bearing steel SUJ2 (the alloying components thereof being shown in Table 1 referred to previously) and has 0.01012 m of the parameter L1, no resonance occurred. In view of this, using the finite element method (FEM) analyzing software (Marc Mentat 2008 r1) (registered trademark) and, also, using the above described Young's modulus E, Poisson's ratio ν and density ρ as respective physical property values, the eigen analysis of the free torsional resonance was carried out. As a result thereof, the frequency f, at which the torsional resonance occurs when the parameter L1 was 0.01012 m, was 19,076 Hz, thus having departed from the oscillation frequency range of the torsional vibration converter 7 that is within 20,000±500 Hz. As a result of determination with the same analysis to find the L1 with which the torsional resonance occurs at the frequency of 20,000 Hz, the parameter L1 was 0.00915 m. When the test piece having the parameter L1 of 0.00915 m was prepared, resonance occurred at the frequency in the vicinity of 20,000 Hz. When evaluation is made by performing the intermittent run (Oscillating time: 110 msec., Break time: 1,100 msec.), in which oscillation and break are alternately repeated, at normal temperatures under atmosphere with the amplifier output of 100%, it has been found that breakdown took place in the order of 107 times in number of loadings (see FIG. 13.). Although the high strength metallic material can be caused to undergo the shear fatigue fracture, promotion of a further high efficiency is necessitated in order to induce the shear fatigue fracture at a low number of loadings regime.

In order to increase the torsional amplitude of the amplitude amplifying horn 8, the amplitude amplifying horn 8 having ϕ38 mm in diameter of the large diameter end face and ϕ13 mm in diameter of the reduced diameter end face was manufactured. The highly efficient amplitude amplifying horn (an exponential type) is so designed and so adjusted as to resonate at a frequency in proximate to 20,000 Hz. A raw material for the highly efficient amplitude amplifying horn is a titanium alloy. As a result of measurement of the Young's modulus E, the Poisson's ratio ν and the density ρ, it has been found that the Young's modulus E, the Poisson's ratio ν and the density ρ were $1.16 \times 10^{11}$ Pa, 0.27 and 4,460 kg/cm³, respectively. Using the FEM analyzing software (Marc Metat 2008 r1) (registered trademark) and, also, using the above described Young's modulus E, Poisson's ratio ν and density ρ as respective physical property values, the eigen value analysis of the free torsional resonance was carried out. As a result thereof, the amplification factor (the ratio of the torsional angle on the small diameter side relative to the torsional angle on the large diameter side) was found to be 43.1 times. Accordingly, it is clear that the amplification factor exhibited by the highly efficient amplitude amplifying horn has increased 67% relative to the standard amplitude amplifying horn. It has, however, found that when at 50% of the output of the amplifier 17 under normal temperatures and atmosphere, the test piece 1 of the above described dimensions made of SUJ2 was fitted and the evaluation was then initiated under the above described intermittent run condition, the phenomenon occurred that the resonance became unstable soon after the start of the evaluation.

In order to avoid the occurrence of the resonance instable phenomenon, the shape of the test piece 1 was reviewed. The theoretical solution of the maximum shear stress amplitude $\tau_{max}$, which acts on the surface of the test piece minimum diameter portion can be given by the following equation (10):

$$\tau_{max} = G\theta_{end} R_1 \beta \frac{\cos(kL_1)\cosh(\alpha L_2)}{\sinh(\beta L_2)} \tag{10}$$

The parameters $R_1$, $L_1$ and $L_2$ represent, respectively, the minimum radius of the test piece 1, the shoulder length and the half chord length (the units of them are expressed in terms of m). The parameters g, α, k and β are determined by the above described equations (1), (3), (4) and (5). The parameter $\theta_{end}$ represents the end face torsional angle of the test piece 1 (the unit is expressed in terms of rad). For the same end face torsional angle $\theta_{end}$, the maximum shear stress $\tau_{max}$, which acts on the test piece minimum diameter portion roughly increases with increase of the size of the test piece, but decrease with decrease of the size of the test piece. Hence, the following two plans have been contemplated as guidelines for effecting the shear fatigue fracture of the test piece 1 without being accompanied by the resonance instable phenomenon, by changing the test piece shape with the highly efficient amplitude amplifying horn 8 of a kind having the increased amplification factor (the ratio of the torsional angle on the reduced diameter side relative to the torsional angle on the large diameter side) of the torsional angle:

(1) To increase the size of the test piece and to cause the large maximum shear stress $\tau_{max}$ to act on the surface of the test piece minimum diameter portion even with a low amplifier output, and (2) As described above, the highly efficient amplitude amplifying horn has its amplification factor having increased 67% relative to that of the standard product. If the test piece is downscaled, the maximum shear stress $\tau_{max}$ that acts on the surface of the test piece minimum diameter portion decreases, but the test piece is downscaled.

In view of those two guidelines, test pieces identified respectively by A to E in Table 15 below were made using the bearing steel SUJ2 listed in Table 1 referred to previously. The test piece A is of the first or initial time shape as hereinbefore described and has a weight of 21.7 g except for the mounting projection comprised of the screw portion used for securement to the amplitude amplifying horn 8. The test pieces B and C were each increased in size in accordance with the guideline (1) above and, the $\tau_{max}$ ratio (relative to the test piece A) is large for the same end face torsional angle and the weight ratio (relative to the test piece A) as well increases. On the other hand, the test pieces D and E were each reduced in size in accordance with the guideline (2) above and, the $\tau_{max}$ ratio (relative to the test piece A) becomes small and the weight ratio (relative to the test piece A) as well decreases. The shoulder portion length L1 referred to in Table 15 is not the theoretical solution determined by the equation (6) referred to above, but is a value determined by the eigen value analysis of the free torsional resonance through the FEM referred to above so as to give rise to the torsional resonance at 20,000 Hz.

TABLE 15

Test Piece Dimensions, $\tau_{max}$ Ratios
(for the same torsional angle) and Weight Ratios

| Test Piece | Shoulder Portion Length $L_1$ (m) | Half Chord Length $L_2$ (m) | Shoulder Portion Radius $R_2$ (m) | Minimum Radius $R_1$ (m) | Arc Radius R (m) | $\tau_{max}$ Ratio (Relative to A) | Weight Ratio (Relative to A)*[1] | Remarks |
|---|---|---|---|---|---|---|---|---|
| A | 0.00915 | 0.00700 | 0.00600 | 0.00300 | 0.00967 | 1.00 | 1.00 | First shape |
| B | 0.01307 | 0.00500 | 0.00600 | 0.00300 | 0.00567 | 1.28 | 1.24 | Guidance (1) |
| C | 0.01464 | 0.00570 | 0.00750 | 0.00410 | 0.00648 | 1.35 | 2.20 | |
| D | 0.00915 | 0.00700 | 0.00500 | 0.00250 | 0.00567 | 0.83 | 0.70 | Guidance (2) |
| E | 0.00677 | 0.00650 | 0.00450 | 0.00200 | 0.00970 | 0.82 | 0.43 | |

*[1]Weight ratio except for the screw portion. The weight of the test piece A except for the screw portion is 21.7 g.

With each of the test pieces 1 fitted to the highly efficient amplitude amplifying horn B, evaluation was made under the above described intermittent run conditions under normal temperature and atmosphere. As a result thereof, the resonance instable phenomenon occurred in the test piece B, designed in accordance with the guideline (1) above, at 50% of the amplifier output. The resonance did not occur in the test piece C even at 10% of the amplifier output. On the other hand, the resonance instable phenomenon occurred in the test piece D, designed in accordance with the guideline (2) above, at 80% of the amplifier output. No resonance instable phenomenon occurred in the test piece E even at 90% of the amplifier output. At 90% of the amplifier output, the shear fatigue fracture occurred within a low cycle number of loadings regime in the order of 105 times in number of loadings. In view of the foregoing, it has been revealed that the test piece weight is closely related with the resonance instable phenomenon. It appears to have resulted because the maximum output of the torsional vibration converter 7 is too low of 300 W. It has been decided that the test piece E has to be employed as a test piece for evaluation.

As hereinabove described, the weight of the test piece A except for the screw portion for securement to the amplitude amplifying horn 8 is 21.7 g. In contrast thereto, the weight of the test piece E except for the screw portion is 9.36 g. It is to be noted that the free end (counter screw side) of the actual test piece need be provided with a center hole by means of a turning technique in order to increase the grinding process accuracy, and therefore, the weight excluding the mounting projection becomes somewhat lighter than 9.36 g. This test piece E is identical with the test piece 1 employed in the practice of the previously described first embodiment and the shape, dimensions and evaluation result of this test piece E are such as shown in FIGS. 7 to 16, reference to which have already been made in describing the first embodiment.

The control and data collecting unit 4A shown in FIGS. 34 and 35 will be described in proper order with reference to FIGS. 19 and 20 and also with reference to FIGS. 36 to 38. The testing condition setting portion 21 shown in FIG. 35 is operable to cause the input screen image of the testing conditions, which is similar to that employed in the practice of the previously described first embodiment, to be displayed by the image display device 18. This input screen image has a material input window for inputting the material for the test piece and a comment input window. The input screen image further has an amplifier output window for inputting the output of the amplifier, a selected run input window for selecting either one of the intermittent run or the continuous run, a time input window for inputting the oscillating time and the break time at one time where the intermittent run is selected, and a test terminating condition input window (the number of loading and the frequency fluctuation band, at which the test is terminated), all of which windows will become windows for inputting a condition for driving the torsional vibration converter 7. Additionally, The input screen image has an initial number of loadings input window, a terminating number of loadings input window, and a collecting interval input window for inputting the collecting interval, all of which windows will become windows for inputting a data collecting condition, and also has a file name input window for inputting the file name. The testing condition setting portion 21 stores information on the testing conditions, inputted through the input screen images best shown in FIG. 19, in the testing condition and collected data storage portion 13A as a single test file and applies an inputted file name thereto. The sequence of inputting is such as shown in, for example, the flowchart of FIG. 37.

Figure 36:
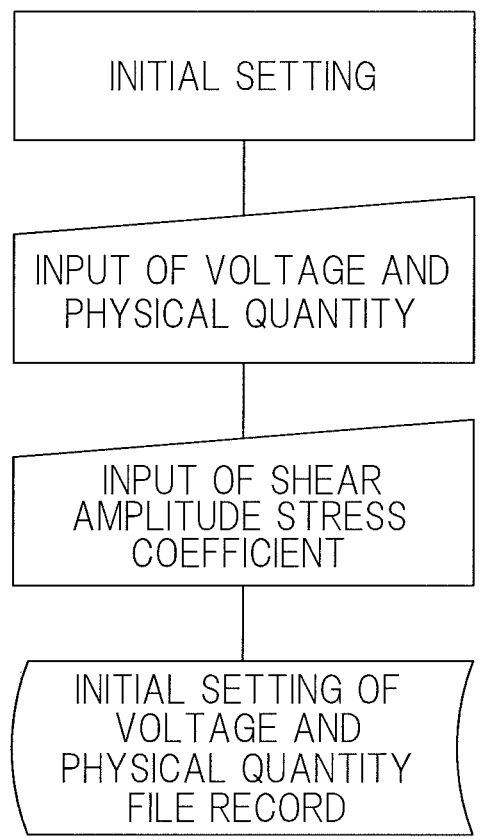
FIG. 36 is a flowchart showing the sequence of an initial setting process.
Figure 37:
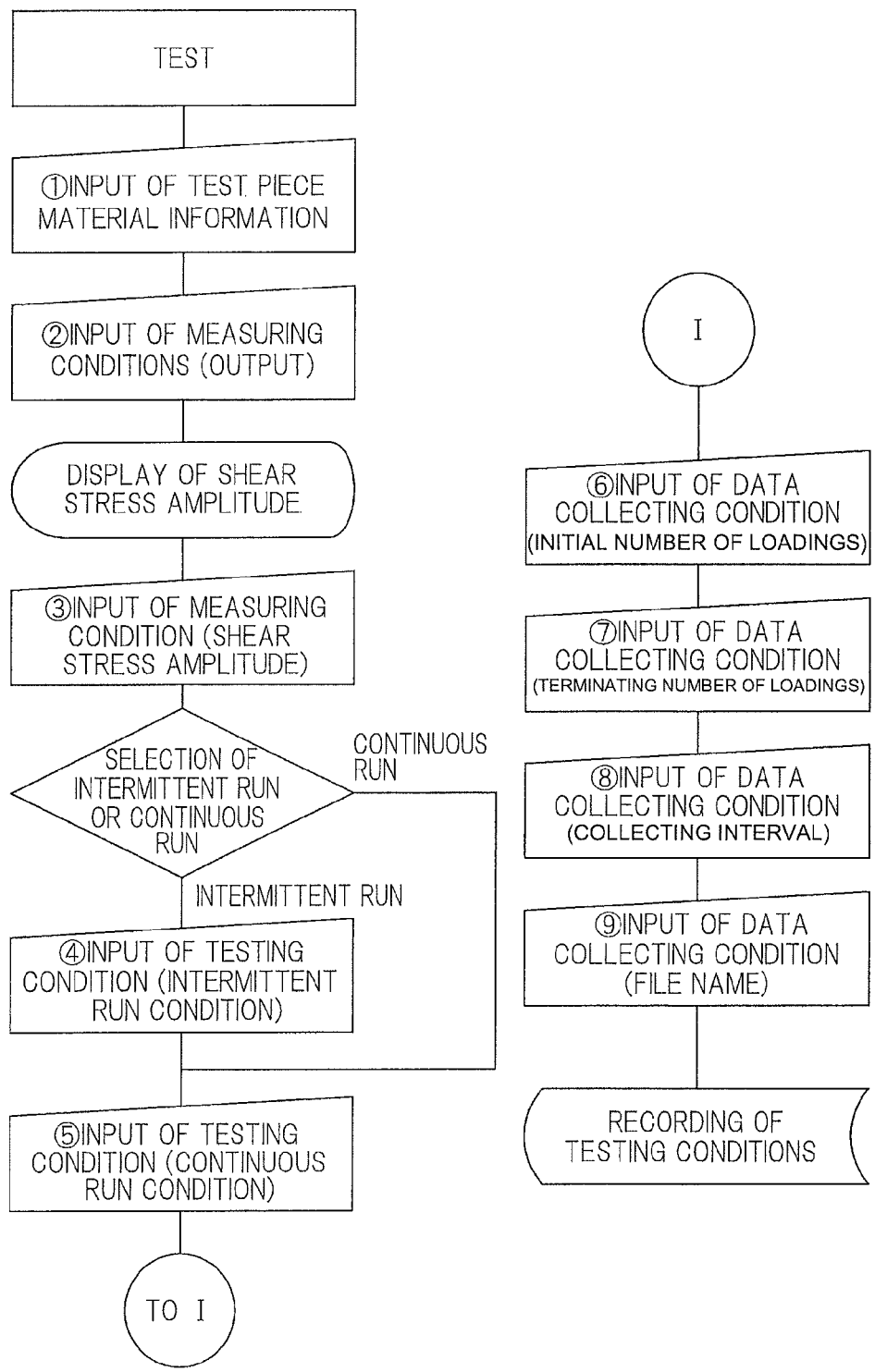
FIG. 37 is a flowchart showing the sequence of inputting testing conditions.

The testing condition setting portion 21 of FIG. 35 displays, other than the input screen image shown in FIG. 19, an input screen image about the initial setting on the image display device 18 and, prompts the input of the physical quantity and the voltage value outputted from the amplifier 17 and the input of the shear amplitude stress coefficient as shown in the flowchart in FIG. 36. Then, the testing condition setting portion 21 performs the initial setting of the physical quantity and the voltage at an inputted value, and store them on the test file referred to above. It is to be noted that the term "physical quantity" referred to above and hereinafter should be construed as meaning a specific value of amplitude IN, amplitude OUT, ultrasonic power, frequency, memory frequency and so on, which will be described below. It is also to be, noted that the term "controller (PC)" appearing in the description of each of the following items should be understood as meaning the control and data collecting unit 4A.

Amplitude IN: It means an amplifier output amplitude, and 0 to 100% is instructed by the controller (PC) at −10 to +10 volts.

Amplitude OUT: It means a voltage output proportional to the actual amplifier output amplitude, and 0 to 100% is instructed by the controller (PC) at −0 to +10 volts.

Ultrasonic power: It means a voltage output proportional to the output of the ultrasonic power, and 0 to 100% is instructed by the controller (PC) at 0 to +10 volts.

Frequency: It means a voltage output proportional to the output of the amplifier operating frequency, and 19.50 to 20.50 kHz is instructed by the controller (PC) at −10 to +10 volts.

Memory frequency: It means a voltage output proportional to the output of the relative frequency recorded in an amplifier memory, and 19.50 to 20.50 kHz is instructed by the controller (PC) at −10 to +10 volts.

Figure 38:
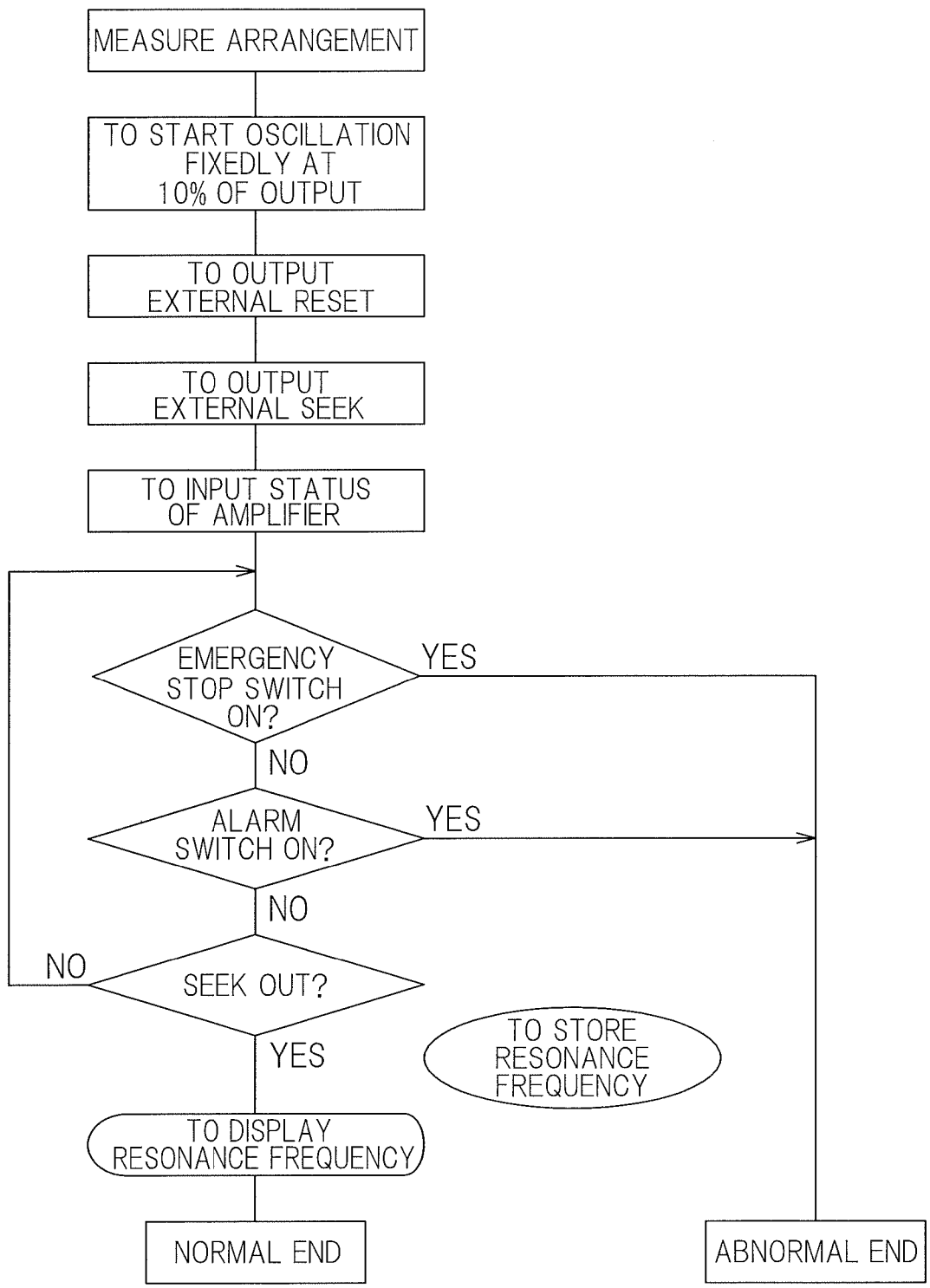
FIG. 38 is a flowchart showing the sequence of preparation for the test.

When a "Oscillation Start" button appearing in the input screen image shown in FIG. 19 is pressed, the resonance frequency is searched at 10% of the output (See FIG. 38.). Once the resonance is affirmed, a "Test Information" tab is to be moved on, followed by pressing of a "Test Start" button, a start command is applied and the test control portion 12A shown in FIG. 35 initiates the test.

The test control portion 12A shown in FIG. 35 performs the control of the amplifier 17 and the test piece cooling unit 9, and also collects data from the amplifier 17 in accordance with the test file and the testing conditions, which are inputted and stored, respectively. To describe in summary, as shown in FIG. 20 in connection with the previously described first embodiment, subsequent to the start of the test at step R1, the amplitude output is fixed at step R3, determination of the testing condition of whether the continuous run should be chosen or whether the intermittent run should be chosen is made at step R4, and process steps R5 to R13 are sequentially performed in the case of the continuous run, but process steps R14 to R24 are sequentially performed in the case of the intermittent run. In either case, the resonance frequency and the output status of the amplifier are collected at steps R6 and R18, respectively, and the test file is updated with the collected data at steps R12 and R22. Once a test terminating condition is satisfied, outputting of the ultrasonic wave is halted at step R26, with the test thus terminated.

The rolling bearing material selecting method according to the second embodiment is such that the metallic material of a kind, in which the shear fatigue property value assessed by the rolling bearing material property evaluating method of the construction described above is higher than the predetermined shear fatigue property value, is employed as a material for the bearing rings and/or rolling elements of the rolling bearing assembly. Accordingly, effects similar to those afforded by the previously described first embodiment can be obtained.

Figures 39A, 39B:
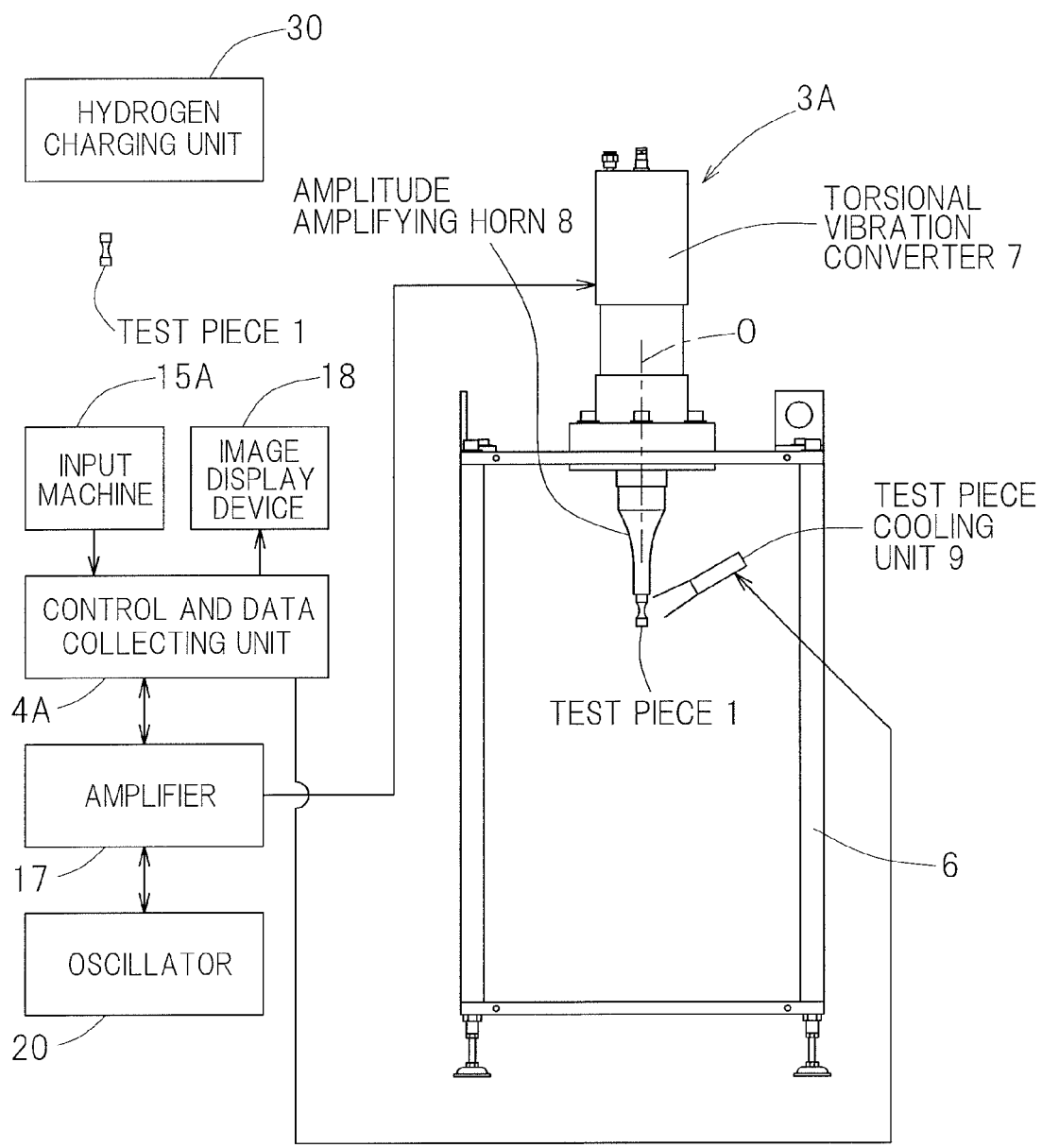
FIG. 39 is a front elevational view showing the apparatus used in the practice of the method of assessing the shear fatigue property of the rolling contact metal material under hydrogen penetration according to a third preferred embodiment of the present invention and an explanatory diagram including a block diagram showing the control system thereof and a block diagram showing a hydrogen charging unit.
Figure 40:
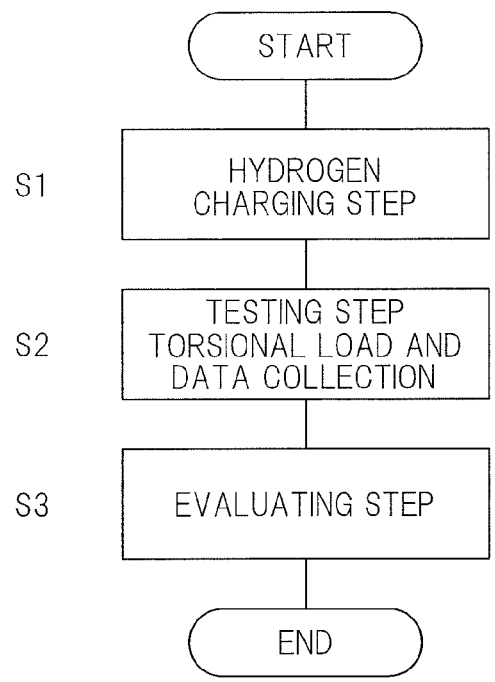
FIG. 40 is a schematic flowchart showing the sequence of the assessing method.

A third preferred embodiment of the present invention will be hereinafter described with particular reference to FIGS. 39A and 39B to 44. In describing this third embodiment, only differences appearing therein from the previously described second embodiment will be described, noting that component parts thereof similar to those in the previously described second embodiment are shown by like reference numerals and the details thereof are not reiterated for the sake of brevity. The shear fatigue property assessing method according to this third embodiment for the rolling contact and torsional load acting metallic material under hydrogen penetration differs from the previously described second embodiment in that as shown in FIG. 39A, prior to the ultrasonic torsional fatigue test conducted with a testing device of a structure shown in FIG. 39B, a hydrogen charging step S1 of charging the test piece 1 of the metallic material with hydrogen as shown in FIG. 40 is employed, but other structural features remain the same as those in the previously described second embodiment. At a test step S2 following the hydrogen charging step shown in FIG. 40, data or the like concerning the relation between the shear stress amplitude and the number of loading under the hydrogen charging condition are collected and, at an evaluating step S3, the shear fatigue property such as, for example, the shear fatigue strength is evaluated from the number of loadings and the shear stress amplitude so collected at the evaluating step S2.

Figure 44:
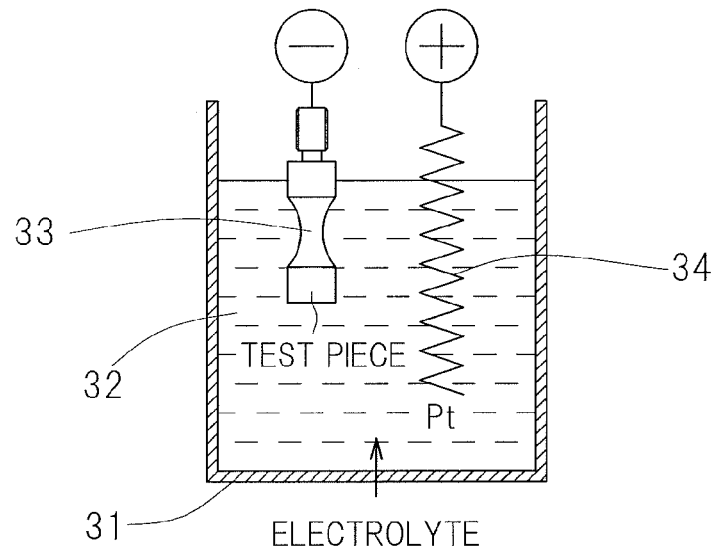
FIG. 44 is an explanatory diagram showing one example of a method of charging hydrogen by means of the catholyte.

A hydrogen charging unit 30 shown in FIG. 39A is operable to charge the test piece 1 with hydrogen according to either one of the following methods. By way of example, it is operable to charge the test piece with hydrogen by means of catholyte, or to charge the test piece 1 with hydrogen by immersing the test piece in an aqueous solution. The catholyte hydrogen charging is carried out by, for example, as shown in FIG. 44, immersing a platinum electrode 34 and a test piece 33 in an electrolytic solution 32 filled in a container 31 and applying a voltage with the test piece 33 and the electrode 34 set to minus and plus polarities, respectively. Regarding those hydrogen charging, the details thereof will be described later. Other structural features are identical with those shown and described in connection with the previously described second embodiment.

According to this testing method, since the ultrasonic torsional fatigue test is carried out, in which ultrasonic torsional vibrations of the oscillating frequency falling within the ultrasonic wave region are applied to the test piece, the torsional fatigue test, in which extremely high speed loads can be repeatedly applied, can be carried out. For this reason, before the charged hydrogen is scattered and lost, the shear fatigue is given to the test piece made of the metallic material that is subject to the evaluation and the shear fatigue property under the hydrogen penetration can be reasonably and quickly evaluated. By way of example, if continuously oscillated at 20,000 Hz, the number of loadings, which is $10^7$ times, can be attained only in 8.3 min. Since the test piece is resonated, it is possible to induce the shear fatigue fracture efficiently with the slight energy invested.

The test piece made of the standard quenched and tempered bearing steel SUJ2 under the normal temperatures and atmosphere and hydrogen penetration was evaluated by means of the intermittent run in which the oscillation and break are alternately repeated. A knurl portion of the test piece was applied an emery grinding (#500, #2000) and a diamond lapping (1 μm in particle size). Regardless of the magnitude of the maximum shear stress amplitude, the oscillating time and the break time were chosen to be thoroughly 110 msec. and 1100 msec., respectively. The test piece is of the same production lot as that used in the previously described end face torsional angle measurement. The test was aborted unless damages occur until $10^8$ times.

In the evaluation under the hydrogen penetration, prior to the test, the catholyte hydrogen charging is applied to the test piece for just 20 hours. The electrolyte is employed in the form of an aqueous solution of 0.05 mol/L of dilute sulfuric acid added with 1.4 g/L of thiourea. The electric current density was chosen to be 0.2 mA/cm². Under this hydrogen charging condition, about 3.5 mass-ppm of diffusive hydrogen penetrates. When the test piece is charged with hydrogen in the aqueous solution of dilute sulfuric acid, it is covered by a thin corrosive product, and therefore, the knurl portion of the test piece need be applied a diamond lapping (1 μm in particle size) again to remove the corrosive product and to improve the surface roughness. Upon completion of the hydrogen charging, just 10 minutes thereafter, the test was initiated under the normal temperature and atmosphere, and the diamond lapping was applied during the course thereof.

Figure 41:
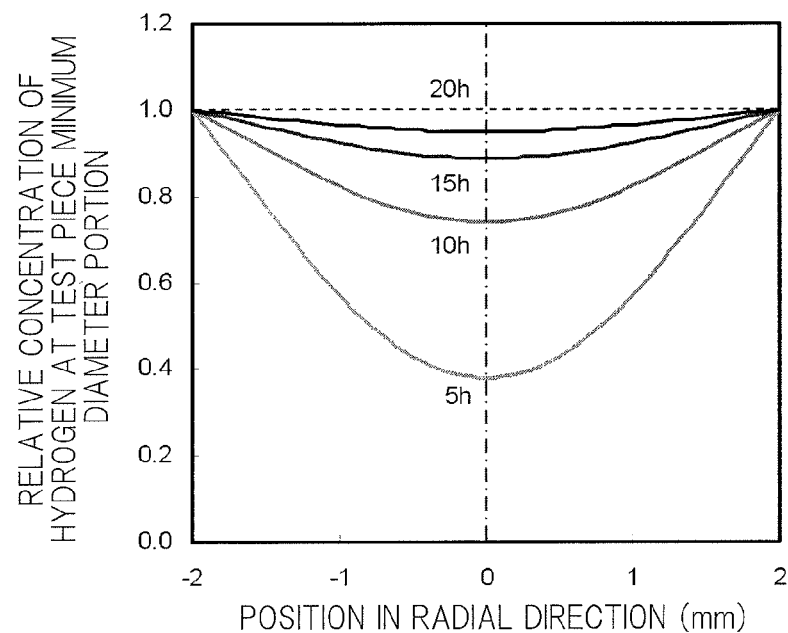
FIG. 41 is a chart showing a time based change of the relative hydrogen concentration of the smallest diameter portion of the test piece.

The diffusion coefficient of hydrogen in the standard quenched and tempered bearing steel SUJ2 under the normal temperatures and atmosphere, which was measured by means of an electrochemical hydrogen permeability test (See the non-patent document 7 referred to previously.) was $3.76 \times 10^{-11}$ m²/sec. The minimum diameter of the ultrasonic torsional fatigue test piece is 4 mm. The time dependent change of the relative hydrogen concentration of the test piece minimum diameter portion which was calculated using the above described diffusion coefficient is shown in FIG. 41. It shows the saturation taking place substantially to the core in 20 hours. This is the reason that the hydrogen charging time was chosen to be just 20 hours.

As another electrolytic solution for the catholyte hydrogen charging, an aqueous solution of sodium chloride, which is neutral and safe, is available, although a small amount of corrosive product may adhere to the test piece. In general, the concentration of the aqueous solution of sodium chloride is adjusted to about 3 mass %. It is, however, to be noted that the hydrogen charging efficiency is not so good as aqueous acids. As a catalyst poison effective to increase the hydrogen charging efficiency, which is the aqueous solution of sodium chloride, ammonium thiocyanate is available. Its potency is limited to 3 g/L. Where the corrosive product is uncalled for, an aqueous solution of sodium hydrate is available although it is alkaline and does therefore require a careful handling. In general, the concentration of aqueous solution of sodium hydrate is adjusted to about 1 mol/L. The hydrogen charging efficiency is not so good as the above described neutral aqueous solution. As a catalyst poison effective to further increase the hydrogen charging efficiency, which is the aqueous solution of sodium hydrate, sodium sulfide nonahydrate is available. Its potency is limited to 1 g/L.

In contrast to the catholyte hydrogen charging with the use of any of the above described various aqueous solutions, there is a immersive hydrogen charging, in which a test piece is merely immersed in the aqueous solution. An aqueous solution of ammonium thiocyanate is available for this purpose. Its potency is limited to the density of 20 mass %.

Figure 42:
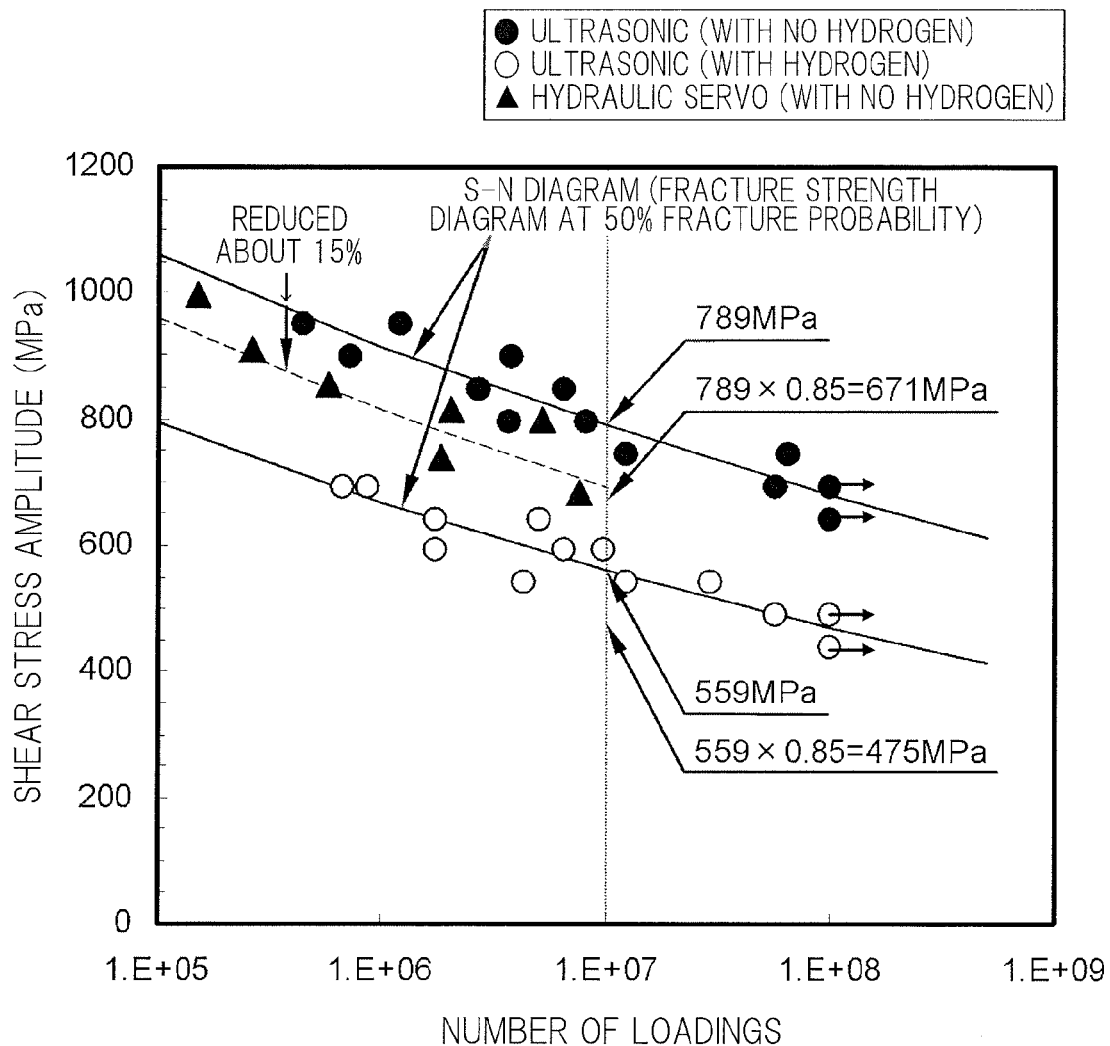
FIG. 42 is a chart showing the relation between the shear stress amplitude and the number of loadings, obtained as a result of the ultrasonic torsional fatigue test conducted under the atmosphere of normal temperatures and the hydrogen penetration, and the S-N diagram (solid line)

FIG. 42 illustrates the relation between the shear stress amplitude and the number of loadings under the presence or absence of the hydrogen charging obtained as a result of the ultrasonic torsional fatigue test. The solid lined curve in the chart of FIG. 42 represents the S-N diagram (the diagram representative of the fatigue strength at the fracture probability of 50%) determined by applying to the continuously-decreasing-type line chart of the metallic material fatigue reliability evaluating standards JSMS-SD-6-02 stipulated by the Society of Materials Science, Japan (JSMS). The shear fatigue strength at $10^7$ times was found to be 789 MPa with no hydrogen charging, but 559 MPa with hydrogen charging, and it is clear that the shear fatigue strength decreased under the hydrogen penetration.

Using the bearing steel SUJ2, shown in Table 1 referred to previously, as a raw material, in a manner similar to that practiced in the previously described first embodiment, the torsional fatigue test piece (standard quenched and tempered) such as shown in FIG. 14 was made and the torsional fatigue test was carried out in a manner similar to that in the previously described first embodiment. As a result thereof, blackened triangular plots shown in the chart of FIG. 42 were obtained, and the fatigue strength at finite life obtained as a result of the hydraulic servo torsional fatigue test was about 15% reduced as compared with that exhibited in the ultrasonic torsional fatigue test result. The ultrasonic torsional fatigue test tends to evaluate the shear fatigue strength so higher than the conventional torsional fatigue test. Accordingly, it is recommended that respective values of 671 MPa and 475 MPa, which are 85% of the shear fatigue strengths of 789 MPa and 559 MPa with hydrogen charging and without hydrogen charging at $10^7$ times, are to be used as measures during the discussion over the absolute value.

Also, by the same reason as in the previously described first embodiment, applying the standards for the tension and compression fatigue test as it stands, respective values of 631 MPa and 447 MPa, which are 80% of the shear fatigue strengths of 789 MPa and 559 MPa with hydrogen charging and without hydrogen charging at $10^7$ times, can be used as measures during the discussion over the absolute value.

Figure 43:
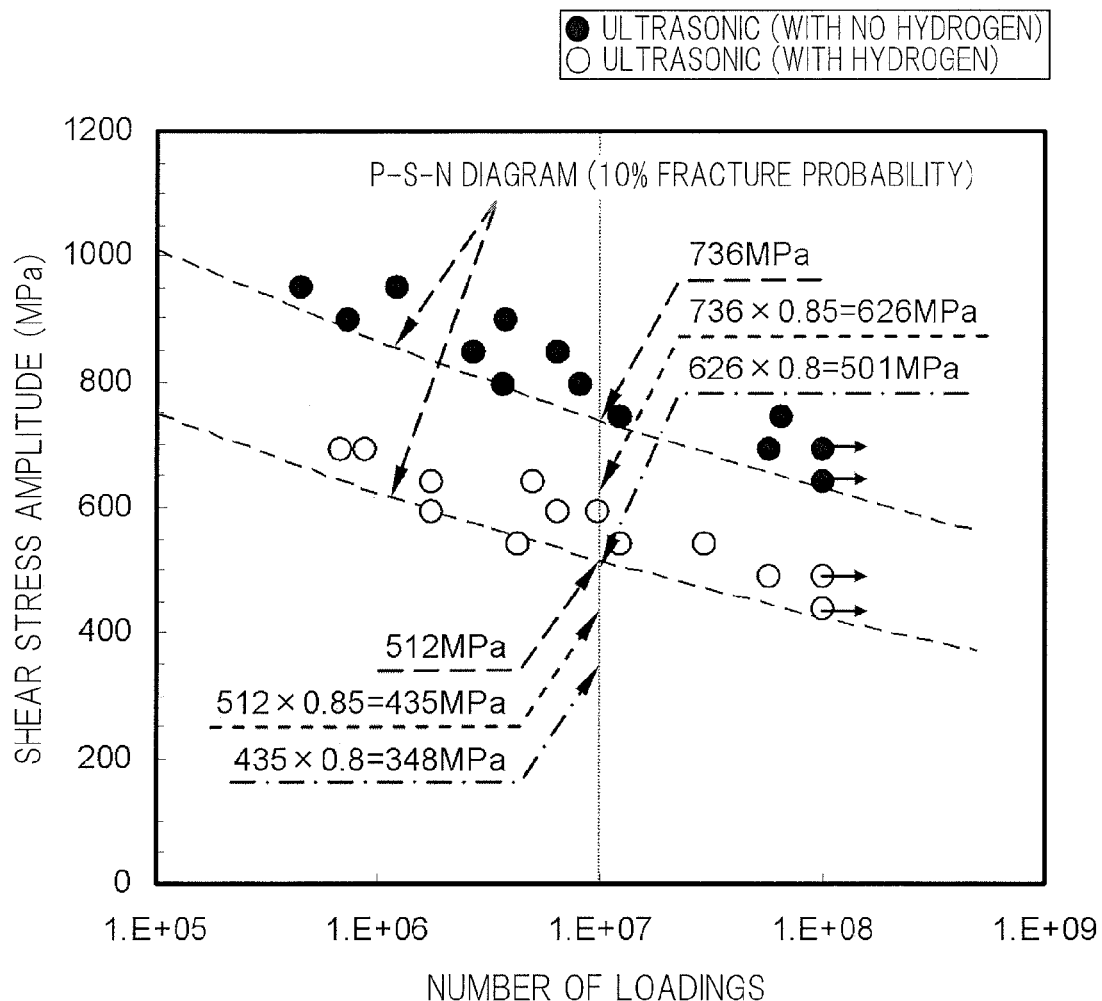
FIG. 43 is a chart showing the P-S-N diagram of the 10% fracture probability obtained from the relation shown in FIG. 42.

In this third embodiment, the metallic material fatigue reliability evaluating standards JSMS-SD-6-02, stipulated by the Society of Materials Science, Japan (JSMS), was employed in determining the shear fatigue strength at $10^7$ times in the chart of FIG. 42. It has a function of acquiring the P-S-N diagram with a small amount of data. FIG. 43 illustrates the P-S-N diagram (broken line) at the fracture probability of 10% obtained thereby, and the 10% shear fatigue strengths with hydrogen charging and without hydrogen charging, respectively, at $10^7$ times were 736 MPa and 512 MPa. They may be used as measures during the discussion over the absolute value.

If the discussion over the absolute is desired most safely, the above three are to be combined together. In other words, in consideration of the fracture probability, is corrected the higher evaluation of the shear fatigue strength of the ultrasonic torsional fatigue test than that of the conventional torsional fatigue test and additionally, applies the standards of the tension and compression fatigue test. With no hydrogen charge, it is recommended that the value of 501 MPa, which is 80% of the value of 626 MPa that is in turn 85% of the value of 736 MPa of the 10% shear fatigue strength at $10^7$ times, is to be used as a measure during the discussion. With hydrogen charge, it is recommended that the value of 348 MPa, which is 80% of the value of 435 Mpa that is in turn 85% of the value of 512 MPa of the 10% shear fatigue strength at $10^7$ times, is to be used as a measure during the discussion.

In describing any one of the first to third embodiments the evaluating methods of evaluating the shear fatigue property and of the fatigue limit maximum contact pressure of the rolling contact metallic material have been shown and described, but those evaluating method can be equally applied to any metallic material other than the rolling contact metallic material. An example of application of the present invention will be hereinafter described. In this example of application, in place of the rolling contact metallic material, a high strength metallic material for use in a power transmitting shaft is utilized, and structural features other than it are identical with those shown and described in connection of the previously described second embodiment.

As a testing machine of assessing the shear fatigue property, there is a hydraulic servo type torsional fatigue testing machine and a Schenk's torsional fatigue testing machine, but the load frequency is about 10 Hz at most in the case of the former and about 30 Hz in the case of the latter and a substantial amount of time is required to accomplish the evaluation of the shear fatigue property up until a high number of loadings. The currently most used high strength metallic material for use in the power transmitting shaft is what the amount of manganese Mn, which is a hardenability improving agent, is increased with the carbon steel JIS-S40C and, also, what boron B is added to it, and is subjected to the induction hardening so as to render the prior austenite grain size of a subsurface, as defined by HS, to be within the range from #8 to #10 and tempered at a relatively low temperature (about 150° C.) to have the hardness of about 650 HV.

As hereinabove described, since the conventional torsional fatigue testing machine has a low load frequency, the shear fatigue property of the power transmitting shaft has evaluated when the number of loadings attained at $10^6$ times. However, the number of loadings, which the power transmitting shaft is exposed during the use thereof for a long period of time, is not $10^6$ times and the evaluation of the shear fatigue property is needed until a high number of loadings. By way of example, however, about four months has been required until the number of loadings attains $10^8$ times with the hydraulic servo type torsional fatigue testing machine having 10 Hz in load frequency.

According to the method of this example of application, since an extremely high speed ultrasonic torsional fatigue testing machine, the oscillating frequency of which falls within the ultrasonic wave region, is carried out, in evaluating the shear fatigue property of the high strength metallic material for use in the power transmitting shaft the required number of loadings is attained in a matter of hours and the shear fatigue property can be quickly evaluated. For example, if continuously oscillated at 20,000 Hz, the number of loadings, which is $10^9$ times, attains only in about half a day. Since the test piece is caused to resonate, the investment of the slight energy is effective to induce the shear fatigue fracture.

Exemplar Application 1

As the power transmitting shaft, intermediate shaft steels used in constant velocity universal joints ("CVJ" as abbreviated) is enumerated. Of those intermediate shaft steels, an X steel, in which the amount of Mn is increased, is used for a small diameter component and Y steel, in which the boron B is added to S40C, the mount of Mn is increased and the amount of Si is reduced, is used for a large diameter component. In the instance now under discussion, the heat treating conditions and the shear fatigue property of test pieces X and Y of those two steels are shown.

In Table 16 below, alloying components of the respective steels used in the test pieces X and Y are shown.

TABLE 16

Alloying Components of X Steel and Y Steel
Used in Respective Test Pieces
(wt %. Ti, N, B and O are shown by ppm)

|   | C | Si | Mn | P | S | Ni | Cr | Cu | Al | Ti | N | B | O |
|---|---|---|---|---|---|---|---|---|---|---|---|---|---|
| X | 0.40 | 0.26 | 1.02 | 0.012 | 0.023 | 0.02 | 0.15 | 0.02 | 0.032 | — | 68 | — | 8 |
| Y | 0.40 | 0.05 | 0.99 | 0.013 | 0.016 | 0.02 | 0.13 | 0.01 | — | 420 | 50 | 19 | — |

Respective test pieces were made by subjecting raw materials, used in the test piece X and Y shown in Table 16 above, to a sequential process of Turning→Heat treatment→Grinding and Finishing. The heat treatment used in this case is induction hardening and tempering. The heat pattern of the induction hardening of the raw material used in each of the test pieces and the induction hardening pattern are identical with those shown in FIGS. 31A and 31B and FIGS. 32A and 32B in connection with the previously described first embodiment.

Figure 45:
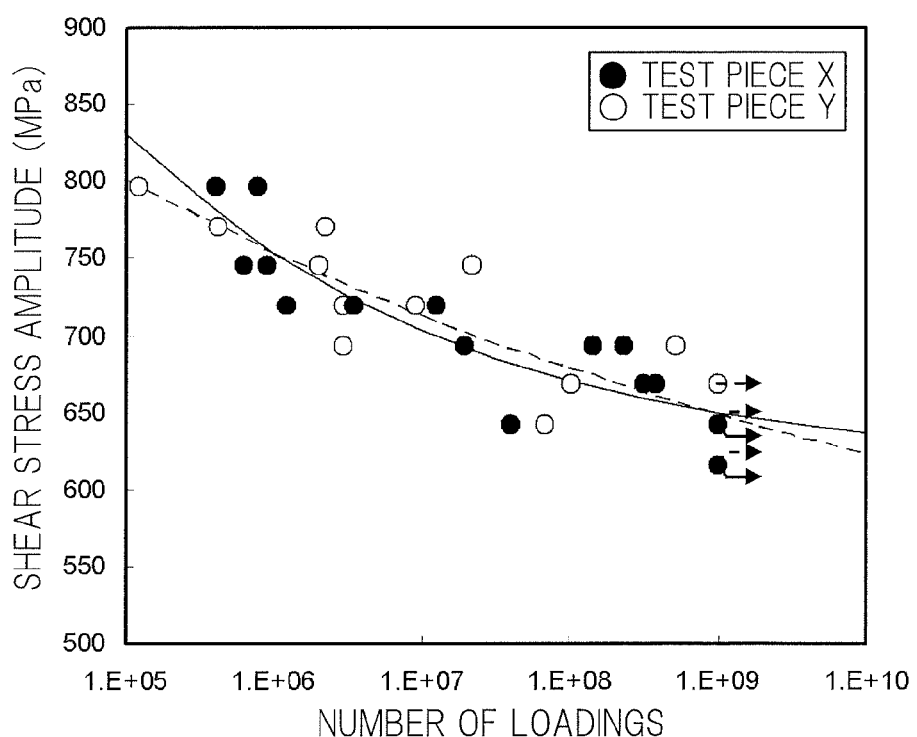
FIG. 45 is a chart showing the shear fatigue property of the test piece.

FIG. 45 illustrates the shear fatigue property exhibited by the test pieces X and Y. The solid and broken lines in the chart of FIG. 45 are S-N diagrams determined by applying to the continuously-decreasing-type line model of the metallic material fatigue reliability evaluating standards JSMS-SD-6-02 stipulated by the Society of Materials Science, Japan, and the respective shear fatigue strengths $\tau_{w0}$ of those test pieces were found to be substantially equal to each other. According to Exemplar Application 1 above, when in evaluating the shear fatigue property of the high strength metallic material for use in the power transmitting shaft the extremely high speed ultrasonic torsional fatigue testing machine, of which oscillating frequency will become within the ultrasonic wave region, is carried out, the required number of loadings is attained in a matter of hours and the shear fatigue property can be quickly evaluated. For example, if continuously oscillated at 20,000 Hz, the number of loadings, which is $10^9$ times, is attained in about half a day.

The summary of the Exemplar Application discussed hereinabove is such as follows:

The shear fatigue property estimating method for estimating the high strength metallic material for use in the power transmitting shaft, which forms a basic construction for each of the following applied modes of the above described Exemplar Application, is a method of evaluating the shear fatigue property of the high strength metallic material for use in the power transmitting shaft by utilizing a test piece made of the metallic material, which comprises:

using;
  a torsional vibration converter for generating torsional vibrations, which will become positive and reversed rotations about the axis of rotation when an electric alternating power is applied,
  an amplitude amplifying horn having a tip end, provided with a mounting portion to which the test piece is fitted coaxially and also having a base end that is fixed to the torsional vibration converter, and operable to amplify the amplitude of the torsional vibration of the vibration converter applied to the base end,
  an oscillator,
  an amplifier for amplifying an output of the oscillator and then applying it to the torsional vibration converter, and
  a control unit for applying an input of the control to the amplifier,
  choosing the shape and the dimensions of the amplitude amplifying horn to be the shape and the dimensions enough to resonate with the torsional vibrations resulting from the drive of the torsional vibration converter;
  choosing the shape and the dimensions of the test piece are chosen to be the shape and the dimensions enough to resonate with the torsional vibrations of the amplitude amplifying horn;
  driving the vibration converter at a frequency region within the ultrasonic wave region so that the amplitude amplifying horn and the test pieces are caused to resonate;
  conducting a test to cause a shear fatigue fracture in the test piece; and
  evaluating the shear fatigue property of the metallic material with the use of the relation between the number of loadings and the shear stress amplitude obtained from the test.

Applied Mode 1:

In the basic construction described above, the torsional vibrations generated by the torsional vibration converter are preferably completely reversed, in which the direction of the positive rotation and the direction of the reversed rotation are symmetrical to each other.

Applied Mode 2:

In the basic construction described above, the lowermost limit of the frequency used to drive the torsional vibration converter is preferably $(20,000-500+\alpha)$ Hz and the uppermost limit thereof is preferably (20,000+500) Hz, it being to be noted that α represents a spare value relative to change in property of the test piece during the test and is equal to or lower than 200 Hz.

Applied Mode 3:

In the basic construction described above, a material for the amplitude amplifying horn is preferably a titanium alloy.

Applied Mode 4:

In the Applied Mode 3 described above, the amplitude amplifying horn is preferably such that regarding an amplitude amplifying horn shaped model excluding a female screw portion at the tip end of the amplitude amplifying horn, to which the test piece is fitted, and a mounting portion formed at a base end of the amplitude amplifying horn so as to protrude from a center portion of an end face thereof and adapted to be fitted to the torsional vibration converter, assuming that physical values are chosen to be $E=1.16 \times 10^{11}$ Pa, $\nu=0.27$ and $\rho=4,460$ kg/m³, the amplification factor, which is the ratio of the torsional angle at a small diameter end face relative to the torsional angle at a large diameter end face, is equal to or greater than 43 times, and, assuming that the torsional angle at the tip end is 0.018 rad, the maximum shear stress acting on the test piece smallest diameter portion surface is equal to or lower than 180 MPa.

Applied Mode 5:

In the basic construction described above, the test piece is preferably of a dumbbell shape including cylindrical shoulder portions at opposite ends thereof and a narrowed intermediate portion continued from the shoulder portions at the opposite end thereof and having an axial sectional shape depicted by an arcuate curve; assuming that the length of each of the shoulder portions is expressed by $L_1$ (m in unit), the half chord length, which is half the length of the narrowed intermediate portion, is expressed by $L_2$ (m in unit), the radius of each of the shoulder portions is expressed by $R_2$ (m in unit), the minimum radius of the narrowed intermediate portion is expressed by $R_1$ (m in unit), the radius of the arcuate curve is expressed by R (m in unit and determined from $L_2$, $R_1$ and $R_2$), the resonance frequency is expressed by f (Hz in unit), the Young modulus is expressed by E (Pa in unit), the Poisson's ratio is expressed by $\nu$ (dimensionless), the density is expressed by $\rho$ (kg/m³ in unit), the parameters $L_2$, $R_1$ and $R_2$ are arbitrarily chosen values, and the frequency f is an arbitrarily chosen value within the frequency range of 20,000±500 Hz at which the torsional vibration converter can be driven, the shoulder portion length $L_1$, for which the test piece resonates at the resonance frequency f, is determined from the following equations (1) to (6) as a theoretical solution; a plurality of test piece shaped models, in which the parameters $L_2$, $R_1$, $R_2$ and R and the shoulder portion length $L_1$ determined as the theoretical solution are slightly shortened, are prepared; an analytic solution $L_{1N}$, in which the torsional resonance occurs at the resonance frequency f, is determined by means of an eigen value analysis of a free torsional resonance by means of a finite element analysis, with use of, for each of those shaped model, an actually measured physical value of a metallic material having the parameters E, $\nu$ and $\rho$ as a respective test piece; and test pieces having the dimensions of $L_2$, $R_1$, $R_2$, R and $L_{1N}$ are prepared and used in a test.

$$E = \frac{G}{2(1+\nu)} \quad (1)$$

$$\omega = 2\pi f \quad (2)$$

-continued $$\alpha = \frac{1}{L_2} \operatorname{Arccosh}\left(\frac{R_2^2}{R_1^2}\right) \quad (3)$$

$$k = \omega \sqrt{\frac{\rho}{G}} \quad (4)$$

$$\beta = \sqrt{\alpha^2 - k^2} \quad (5)$$

$$L_1 = \frac{1}{k} \operatorname{Arctan}\left[\frac{1}{k}\{\beta \coth(\beta L_2) - \alpha \tanh(\alpha L_2)\}\right] \quad (6)$$

Applied Mode 6:

In the basic construction described above, in order to suppress heat emission from the test piece, the test piece is preferably forcibly cooled with air.

Applied Mode 7:

In the basic construction described above, in order to suppress the increase of the temperature of the test piece, loading and break of the torsional vibration applied by the torsional vibration converter to the test piece is preferably alternately repeated.

The estimating apparatus for assessing the shear fatigue property of the high strength metallic material for use in the power transmission shaft in the above described Exemplar Application is an apparatus for testing and assessing the shear fatigue property of the high strength metallic material for use in the power transmitting shaft with the use of a test piece made of the high strength metallic material, which apparatus includes:

a torsional vibration converter for generating torsional vibrations, which will become positive and reversed rotations about the axis of rotation when an electric alternating power is applied;

an amplitude amplifying horn having a tip end, provided with a mounting portion to which the test piece is fitted coaxially, and also having a base end that is fixed to the torsional vibration converter, and operable to amplify the amplitude of the torsional vibration of the vibration converter applied to the base end;

an oscillator;

an amplifier for amplifying an output of the oscillator and then applying it to the torsional vibration converter; and a control and data collecting unit for applying an input of the control to the amplifier and collecting data including the oscillating frequency, the status of the amplifier and the number of loadings, and in which the shape and the dimensions of the amplitude amplifying horn are chosen to be the shape and the dimensions enough to resonate with the torsional vibrations resulting from the drive of the torsional vibration converter, the shape and the dimensions of the test piece are chosen to be the shape and the dimensions enough to resonate with the torsional vibrations of the amplitude amplifying horn, and the vibration converter is driven at a frequency region within the ultrasonic wave region so that the amplitude amplifying horn and the test pieces are caused to resonate to fracture the test piece upon shear fatigue.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

REFERENCE NUMERALS

1 . . . Test piece
1a . . . Shoulder portion
1b . . . Narrowed intermediate portion
2 Ultrasonic torsional fatigue testing machine
3, 3A . . . Ultrasonic torsional fatigue testing machine main body
4 . . . Testing machine control device
4A . . . Control and data collecting unit
5 . . . Fatigue limit maximum contact pressure estimating device
6 Frame
7 Torsional vibration converter
8 . . . Amplitude amplifying horn
9 . . . Test piece cooling unit
10 . . . Computer
11 . . . Testing machine control program
17 . . . Amplifier
19 . . . Fatigue limit maximum contact pressure estimating program
20 . . . Oscillator
21 . . . Testing condition setting portion
22 . . . Input unit
23 . . . Shear fatigue strength determining unit
24 . . . Fatigue limit maximum contact pressure calculating unit
27 . . . Intermittent oscillation control portion
30 . . . Hydrogen charging unit
M1 . . . Object manufactured by the metallic material
M2 . . . Contacting object

What is claimed is:

1. A method of assessing a shear fatigue property of a metallic material that undergoes a rolling contact using a torsional vibration converter for generating torsional vibrations, which will become positive and reversed rotations about the axis of rotation when an electric alternating power is applied, an amplitude amplifying horn having a tip end, provided with a mounting portion to which a metallic material is fitted coaxially and also having a base end that is fixed to the torsional vibration converter, and operable to amplify the amplitude of the torsional vibration of the vibration converter applied to the base end, an oscillator, an amplifier for amplifying an output of the oscillator and then applying the output to the torsional vibration converter, and a control unit for applying an input of the control to the amplifier, which method comprises:
  a testing step of determining a relation between a shear stress amplitude of the metallic material and the number of loadings by means of an ultrasonic torsional fatigue test; and
  a shear fatigue strength determining step of determining a shear fatigue strength $\tau_{lim}$ within an ultra long life regime from the determined relation between the shear stress amplitude and the number of loadings in accordance with a predetermined standard.

2. The method of assessing the shear fatigue property of the rolling contact metallic material as claimed in claim 1, in which the ultrasonic torsional fatigue test is chosen to be a completely reversed torsional fatigue test, in which torsions in respective directions of positive and reversed rotations relative to the test piece are symmetrical to each other.

3. The method of assessing the shear fatigue property of the rolling contact metallic material as claimed in claim 1, in which the metallic material is a rolling contact metallic material, which is a rolling bearing steel and which becomes a bearing ring and/or a rolling element of a rolling bearing assembly.

4. The method of assessing the shear fatigue property of the rolling contact metallic material as claimed in claim 1, in which the predetermined standards used during the shear fatigue strength determining step for determining the shear fatigue strength $\tau_{lim}$ within the ultra long life regime is a treatment of determining a curve, in which the relation between the shear stress amplitude and the number of loadings, as a test result, is applied to a fatigue limit line model descriptive of the shear fatigue strength, and then determining the shear fatigue strength from such curve.

5. The method of assessing the shear fatigue property of the rolling contact metallic material as claimed in claim 1, in which the predetermined standards used during the shear fatigue strength determining step for determining the shear fatigue strength $\tau_{lim}$ within the ultra long life regime is a treatment of determining a curve, in which the relation between the shear stress amplitude and the number of loadings, as a test result, is applied to a continuously decreasing type curve model descriptive of the shear fatigue strength, and then determining the shear fatigue strength from such curve.

6. The method of assessing the shear fatigue property of the rolling contact metallic material as claimed in claim 1, in which during the test step, a plurality of the ultrasonic torsional fatigue tests are carried out to determine a plurality of relations between the shear stress amplitude of the metallic material and the number of loadings and, during the shear fatigue strength determining step, a P-S-N diagram of an arbitrarily chosen fracture probability is determined from the relation between the shear stress amplitude and the number of loadings, determined during the plurality of the test steps, and from this P-S-N diagram the shear fatigue strength $\tau_{lim}$ within the ultra long life regime is determined.

7. The method of assessing the shear fatigue property of the rolling contact metallic material as claimed in claim 1, in which a value determined by combining two or more of the following corrections (a), (b) and (c) is rendered to be the shear fatigue strength $\tau_{lim}$ within the ultra long life regime for use in evaluating the shear fatigue property:
  (a) a fracture probability correction to obtain an arbitrary chosen P-S-N diagram descriptive of an arbitrary fracture probability, which diagram is determined from the relation between the shear stress amplitude and the number of loadings, obtained through the test, and to render the shear fatigue strength within the ultra long life regime to be the shear fatigue strength $\tau_{lim}$ within the ultra long life regime for use in evaluating the shear fatigue strength;
  (b) an excessive evaluation correction to render the value of 85% relative to the shear fatigue strength within the ultra long life regime, that is determined from the relation between the shear stress amplitude and the number of loadings, obtained through the test, to be the shear fatigue strength $\tau_{lim}$ within the ultra long life regime for use in evaluating the shear fatigue strength;
  (c) a dimensional effect correction to render the value of 80% relative to the shear fatigue strength within the ultra long life regime, that is determined from the relation between the shear stress amplitude and the number of loadings, obtained through the test, to be the shear fatigue strength $\tau_{lim}$ within the ultra long life regime for use in evaluating the shear fatigue strength.

8. The method of assessing the shear fatigue property of the rolling contact metallic material as claimed in claim 1,
wherein the shape and the dimensions of the amplitude amplifying horn are chosen to be the shape and the dimensions enough to resonate with the torsional vibrations resulting from the drive of the torsional vibration converter;
the shape and the dimensions of the test piece are chosen to be the shape and the dimensions enough to resonate with the torsional vibrations of the amplitude amplifying horn;
a test is conducted to cause a shear fatigue fracture in the test piece by driving the vibration converter at a frequency region within the ultrasonic wave region and causing the amplitude amplifying horn and the test pieces to resonate; and
using the relation between the number of loadings and the shear stress amplitude, obtained from the test, the shear fatigue property of the metallic material is evaluated.

9. The method of assessing the shear fatigue property of the rolling contact metallic material as claimed in claim 8, in which the amplifier is such that the magnitude of an output thereof and the ON or OFF state thereof are controllable in response to an input from the outside.

10. The method of assessing the shear fatigue property of the rolling contact metallic material as claimed in claim 8, in which the lowermost limit value of the frequency, at which the torsional vibration converter is driven, is chosen to be (20,000−500+α) Hz and the uppermost limit value thereof is (20,000+500+α) Hz, where α represents a spare value relative to a change in property of the test piece during the test and α is not higher than 200 Hz.

11. The method of assessing the shear fatigue property of the rolling contact metallic material as claimed in claim 8, in which the amplitude amplifying horn has a transverse sectional shape which is round and the longitudinal sectional shape except for a base end portion is of a tapered shape.

12. The method of assessing the shear fatigue property of the rolling contact metallic material as claimed in claim 8, in which the test piece is of a dumbbell shape including cylindrical shoulder portions at opposite ends thereof and a narrowed intermediate portion continued from the shoulder portions at the opposite end thereof and having an axial sectional shape depicted by an arcuate curve; and
when the length of each of the shoulder portions is expressed by $L_1$ (m in unit), the half chord length, which is half the length of the narrowed intermediate portion, is expressed by $L_2$ (m in unit), the radius of each of the shoulder portions is expressed by $R_2$ (m in unit), the minimum radius of the narrowed intermediate portion is expressed by $R_1$ (m in unit), the radius of the arcuate curve is expressed by R (m in unit and determined from $R_1$, $R_2$ and $L_2$), the resonance frequency is expressed by f (Hz in unit), the Young modulus is expressed by E (Pa in unit), the Poisson's ratio is expressed by ν (dimensionless), the density is expressed by ρ (kg/m³ in unit);
the parameters $L_2$, $R_1$ and $R_2$ are arbitrarily chosen values, and the frequency f is an arbitrarily chosen value within the frequency range of 20,000±500 Hz at which the torsional vibration converter can be driven, the shoulder portion length $L_1$, for which the test piece resonates at the resonance frequency f, is determined from the following equations (1) to (6) as a theoretical solution;
a plurality of test piece shaped models having different values of the parameters $L_2$, $R_1$, $R_2$ and R as well as the shoulder portion length slightly shortened than $L_1$ determined as the theoretical solution are prepared; and
an analytic solution $L_{1N}$, in which the torsional resonance occurs at the resonance frequency f, is determined by an eigen value analysis of a free torsional resonance by means of a finite element analysis, using, for each of those shaped models, an actually measured physical value of a metallic material with the Young modulus E, the Poisson's ratio ν and the density ρ taken as respective physical values, and test pieces having the dimensions of $L_2$, $R_1$, $R_2$, R and $L_{1N}$ are prepared and used in a test:

$$E = \frac{G}{2(1+v)} \quad (1)$$

$$\omega = 2\pi f \quad (2)$$

$$\alpha = \frac{1}{L_2}\text{Arccosh}\left(\frac{R_2^2}{R_1^2}\right) \quad (3)$$

$$k = \omega\sqrt{\frac{\rho}{G}} \quad (4)$$

$$\beta = \sqrt{\alpha^2 - k^2} \quad (5)$$

$$L_1 = \frac{1}{k}\text{Arctan}\left[\frac{1}{k}\{\beta\coth(\beta L_2) - \alpha\tanh(\alpha L_2)\}\right]. \quad (6)$$

13. The method of assessing the shear fatigue property of the rolling contact metallic material as claimed in claim 12, in which the torsional vibration converter has a rated output of 300 W and the capacity of the test piece, excluding a male screw portion of the test piece through which the latter is fitted to an amplitude amplifying horn tip end and a center hole portion at a counter mounting portion end face required for processing the test piece, is chosen to be $1.2\times10^{-6}$ m³ or smaller;
where the end face torsional angle of the test piece is 0.01 rad, with respect to the test piece shaped model excluding the male screw portion, through which it is fitted to a tip end of the amplitude amplifying horn, and the center hole portion at the counter mounting portion end face required for processing it, when the physical value is chosen that $E=2.04\times10^{11}$ Pa, $v=0.29$ and $\rho=7{,}800$ kg/m³, the maximum shear stress, which acts on a surface of a test piece minimum diameter portion and which is determined by the eigen value analysis of the free torsional resonance by means of the finite element analysis is 520 MPa or higher.

14. The method of assessing the shear fatigue property of the rolling contact metallic material as claimed in claim 1, in which after a hydrogen charge is effected to the test piece, the shear fatigue property of the metallic material under penetrated hydrogen is evaluated by means of the ultrasonic torsional fatigue test conducted on this test piece.

15. The method of assessing the shear fatigue property of the rolling contact metallic material as claimed in claim 14, in which hydrogen is charged through a catholyte.

16. The method of assessing the shear fatigue property of the rolling contact metallic material as claimed in claim 14, in which a test piece is immersed in an aqueous solution and then hydrogen is charged.

17. An apparatus for assessing a shear fatigue property of a metallic material that undergoes a rolling contact, which comprises:
a torsional vibration converter for generating torsional vibrations, which will become positive and reversed rotations about the axis of rotation when an electric alternating power is applied;

an amplitude amplifying horn having a tip end, provided with a mounting portion to which the metallic material is fitted coaxially and also having a base end that is fixed to the torsional vibration converter, and operable to amplify the amplitude of the torsional vibration of the vibration converter applied to the base end;

an oscillator;

an amplifier for amplifying an output of the oscillator and then applying the output to the torsional vibration converter;

a control and data collecting unit for applying an input of the control to the amplifier and collecting data including an excitation frequency, state of the amplifier and the number of loadings;

an input unit for storing a relation between the shear stress amplitude of the metallic material and the number of loadings in a predetermined storage area, the relation being determined by means of an ultrasonic torsional fatigue test; and a shear fatigue strength determining unit for determining the shear fatigue strength $\tau_{lim}$ within the ultra long life regime from the stored relation between the shear stress amplitude and the number of loadings in accordance with a predetermined standard.

18. The apparatus for assessing the shear fatigue property of the rolling contact metallic material as claimed in claim 17, in which the metallic material is a rolling bearing steel that becomes a bearing ring and/or a rolling element of a rolling bearing assembly.

19. The apparatus for assessing the shear fatigue property of the rolling contact metallic material as claimed in claim 17, in which:

the shape and the dimensions of the amplitude amplifying horn are chosen to be the shape and the dimensions enough to resonate with the torsional vibrations resulting from the drive of the torsional vibration converter;

the shape and the dimensions of the test piece are chosen to be the shape and the dimensions enough to resonate with the torsional vibrations of the amplitude amplifying horn; and a test is conducted to cause a shear fatigue fracture in the test piece by driving the vibration converter at a frequency region within the ultrasonic wave region and causing the amplitude amplifying horn and the test pieces to resonate.

20. The apparatus for assessing the shear fatigue property of the rolling contact metallic material as claimed in claim 19, in which the lowermost limit value of the frequency, at which the torsional vibration converter is driven, is chosen to be $(20,000-500+\alpha)$ Hz and the uppermost limit value thereof is $(20,000+500+\alpha)$ Hz, where $\alpha$ represents a spare value relative to a change in property of the test piece during the test and $\alpha$ is not higher than 200 Hz.

21. The apparatus for assessing the shear fatigue property of the rolling contact metallic material as claimed in claim 19, in which the torsional vibrations generated by the torsional vibration converter are completely reversed, in which the direction of the positive rotation and the direction of the reversed rotation are symmetrical to each other.

22. A method of estimating the fatigue limit maximum contact pressure with the use of the assessing method of claim 1, further comprising:

a fatigue limit maximum contact pressure calculating step of obtaining the maximum orthogonal shear stress amplitude $\tau_o$, which acts within a subsurface of an object of the previously described metallic material and which is determined by the shape and the dimensions of contact surfaces of the object made of the metallic material and of another object rollingly contacting the object and a load for applying a contact pressure, and then determining the maximum contact pressure $P_{max}$, at which said load equal to the shear fatigue strength $\tau_{lim}$ acts, according to a predetermined equation, to render this maximum contact pressure $P_{max}$ to be an estimated value of the fatigue limit maximum contact pressure $P_{max\ lim}$.

23. A method of assessing the shear fatigue property of the rolling contact metallic material as claimed in claim 22, in which the predetermined equation used during the fatigue limit maximum contact pressure calculating step is expressed as follows:

(Fatigue limit maximum contact pressure $P_{max\ lim}$)= 4×(Shear fatigue strength $\tau_{lim}$).

24. An apparatus for estimating a fatigue limit maximum contact pressure of the rolling contact metallic material by using the apparatus as claimed in claim 17, further comprising:

a fatigue limit maximum contact pressure calculating unit for obtaining the maximum orthogonal shear stress amplitude $\tau_o$, which acts within a subsurface of an object of the metallic material and which is determined by the shape and the dimensions of contact surfaces of the object made of the metallic material and of another object rollingly contacting the object and a load for applying a contact pressure, and then determining the maximum contact pressure $P_{max}$, at which said load equal to the shear fatigue strength $\tau_{lim}$ acts, according to a predetermined equation, to render this maximum contact pressure $P_{max}$ to be an estimated value of the fatigue limit maximum contact pressure $P_{max\ lim}$.

25. The apparatus for estimating the fatigue limit maximum contact pressure of the rolling contact metallic material as claimed in claim 24, in which the predetermined equation used by the fatigue limit maximum contact pressure calculating unit is expressed as follows:

(Fatigue limit maximum contact pressure $P_{max\ lim}$)= 4×(Shear fatigue strength $\tau_{lim}$).

* * * * *

UNITED STATES PATENT AND TRADEMARK OFFICE
CERTIFICATE OF CORRECTION

| | | |
|---|---|---|
| PATENT NO. | : 9,234,826 B2 | Page 1 of 1 |
| APPLICATION NO. | : 13/634412 | |
| DATED | : January 12, 2016 | |
| INVENTOR(S) | : Yukio Matsubara et al. | |

It is certified that error appears in the above-identified patent and that said Letters Patent is hereby corrected as shown below:

On the title page item 56 (Other Publications), Line 1
    Delete "Bahavior" and insert -- Behaviour --, therefor.

Signed and Sealed this
Seventeenth Day of May, 2016

Michelle K. Lee
*Director of the United States Patent and Trademark Office*